(12) United States Patent
Presta et al.

(10) Patent No.: US 8,212,008 B2
(45) Date of Patent: Jul. 3, 2012

(54) ANTIBODIES TO CD200R

(75) Inventors: Leonard G. Presta, San Francisco, CA (US); Holly M. Cherwinski, Boulder Creek, CA (US); Joseph H. Phillips, San Francisco, CA (US)

(73) Assignee: Schering Corporation, Kenilworth, NJ (US)

( * ) Notice: Subject to any disclaimer, the term of this patent is extended or adjusted under 35 U.S.C. 154(b) by 19 days.

(21) Appl. No.: 12/520,033

(22) PCT Filed: Dec. 20, 2007

(86) PCT No.: PCT/US2007/026202
§ 371 (c)(1),
(2), (4) Date: Mar. 15, 2010

(87) PCT Pub. No.: WO2008/079352
PCT Pub. Date: Jul. 3, 2008

(65) Prior Publication Data
US 2010/0178296 A1    Jul. 15, 2010

Related U.S. Application Data

(60) Provisional application No. 60/876,618, filed on Dec. 22, 2006.

(51) Int. Cl.
*C07K 16/00*    (2006.01)
*A61K 39/395*    (2006.01)

(52) U.S. Cl. .................. 530/387.1; 424/130.1

(58) Field of Classification Search ................ None
See application file for complete search history.

(56) References Cited

U.S. PATENT DOCUMENTS

| 6,632,927 B2 * | 10/2003 | Adair et al. ............... 530/387.3 |
| 7,323,553 B2 * | 1/2008 | Fahrner et al. ............... 530/412 |
| 2003/0223991 A1 * | 12/2003 | Cherwinski et al. ....... 424/141.1 |

FOREIGN PATENT DOCUMENTS

| WO | WO00/70045 | 11/2000 |
| WO | WO03/077947 | 9/2003 |
| WO | WO2005/047326 | 5/2005 |

OTHER PUBLICATIONS

Rudikoff et al. 1982, Proc. Natl. Acad. Sci. USA, , 79: 1979-1983.*
Panka et al., 1988, Proc. Natl. Acad. Sci. USA, 85: 3080-3084.*
Cherwinski, Holly M., et al., "The CD200 Receptor is a Novel and Potent Regulator of Murine and Human Mast Cell Function", *The Journal of Immunology* 174(3):1348-1356 (2005).
Gorczynski, Reginald M., et al.; "Anti-CD200R Ameliorates Collagen-Induced Arthritis in Mice"; *Clinical Immunology*; 104(3):256-264 (2002).
Gorczynski, Reginald M.; "CD200 and its receptors as targets for immunoregulation"; *Current Opinion in Investiagional Drugs*; 6(5):483-488 (2005).
International Search Report for International Application No. PCT/US2007/26202 dated Jan. 14, 2009.
Jenmalm, Maria C., et al.; "Regulation of Myeloid Cell Function through the CD200 Receptor"; *The Journal of Immunology*; 176(1):191-199 (2006).
Wright, Gavin J., et al.; "Characterization of the CD200 Receptor Family in Mice and Humans and Their Interactions with CD200"; *The Journal of immunology*; 171:3034-3041 (2003).
Written Opinion of the International Searching Authority for International Application No. PCT/US2007/26202 dated Jun. 24, 2009.

* cited by examiner

*Primary Examiner* — Ilia Ouspenski

(57) ABSTRACT

The present invention relates to binding compounds specific for the human inhibitory CD200R and uses thereof. More specifically, the invention relates to antibodies that recognize the human inhibitory CD200R and modulates its activity in inflammatory and autoimmune disorders.

15 Claims, 18 Drawing Sheets

```
                              ---CDRL1---
              1         10          20           30             40
DX182    EVQMTQSPSTLTASPGESVSINC   KASKNIRSYLA    WYQQKPGKPNKLLIY
DX185    DVQMTQSPSYLAASPGESVSISC   KAGKNINTNLA    WYQAKPGKTNKVLIH
DX178    DVRMTQSPSNLAASPGESVSINC   KASKNISKYLA    WYQQKPGKANRLLIC
DX184    DIVMTQSPTFMSISVGDRVTMSC   KASQNVGSNVD    WYQQKTGQSPKLLIY
DX248    DVQMIQSPSSLSASLGDIVTMC    QASQGTSINLN    WFQQKPGKAPKLLIY
huDX182  DIQMTQSPSSLSASVGDRVTITC   KASKNIRSYLA    WYQQKPGKAPKLLIY

-CDRL2-                                  --CDRL3--
            50        60         70         80           90
DX182    SGSTLHS   GTPSRFSGSGFGTDFTLTIRNLEPEDFGLYYC    QQHHEYPLT
DX185    SGSTLQS   GTPSRFSGSGFGTDFTLTIRSLEPEDFAVYYC    QQHNEFPLT
DX178    SGSTLQS   GTPSRFSGSGFGTDFTLTIRNLEPEDFGLYYC    QQHNEFPLT
DX184    KASNRYT   GVPDRFTGSGSGTGFTFTITNLQAEDLAVYYC    MQSLSFPYT
DX248    SANNLED   GVPSRFSGSGFGTDFTLTISSLEDEDMATYFC    LQITYLPWT
huDX182  SGSTLHS   GVPSRFSGSGSGTDFTLTISSLQPEDFATYYC    QQHHEYPLT

100
DX182    FGSGTKLEIKR      (SEQ ID No.:37)
DX185    FGSGTKLEIKR      (SEQ ID No.:38)
DX178    FGSGTKLEIKR      (SEQ ID No.:39)
DX184    SGAGT            (SEQ ID No.:40)
DX248    FGGGTKLEI        (SEQ ID No.:41)
huDX182  FGQGTKVEIKRT     (SEQ ID No.:42)
```

FIG. 1

```
                                      ---CDRH1---
             1         10        20        30            40
DX182    EIQLQESGPGLVKPSQSLSLTCSVT GYTITSGYDWS WIRKFPGNKMEWMG
DX185    EIQLQESGPGLVKPSQSFSLTCSVT GYTITSGYDWS WIRKFPGNRMEWMG
DX178    EIQLQESGPGLVKPSQSLSLTCSVT GFTITSGYDWS WIRKFPGNKMEWMG
DX184    QVQLKESGPGLVQPSQTLSLTCTVS GFSLTN-NGVS WVRQPPGKGLEWIA
DX248    QVQLQQPGSELVRPGVSVKLSCKAS GYTFTS-YWMH WVKQRHGQGLEWIG
huDX182  QVQLQESGPGLVKPSETLSLTCTVS GYTITSGYDWS WIRQPPGKGLEWIG

------CDRH2------
            50   a    60        70        80  abc     90
DX182     YIN-YGGSTNYKPSLGS RISITRDTSKNQFFLQLNSVSPEDTATYYCAK
DX185     YIN-YSGSTVYNPSLRS RFSITRDTSKNQFFLQLNSVASEDTATYYCAK
DX178     YIG-FSGSTVYNPSLNS RISITRDTAKNQFFLQLNSVTTEDTATYHCAK
DX184     AIS-SGGGTFYNSALKS RLSISRDTSKSQVFLKMNSLQTEDTAIYFCAR
DX248     NIYPGSGSTNYDEKFKS KGTLTVDTSSSTAYMHLSSLTSEDSAVYYCTT
huDX182   YIN-YGGSTN YKPSLGS RVTI SVDTSKNQFSLKLSSVTAADTAVYYCAR -----CDRH3-----
                     103     110
DX182    YNEYKSYIYDWYFDF WGPGTMVTVSS  (SEQ ID No.: 43)
DX185    FEASNTYLYDWYFDF WGPGTMVTVSS  (SEQ ID No.: 44)
DX178    SFVQNTFIYDWFFDF WGPGTMVTVSS  (SEQ ID No.: 45)
DX184    DGD-----WDWYFDF WGPGTMVTVSS  (SEQ ID No.: 46)
DX248    GTG----------AY WGQGTLVTVSA  (SEQ ID No.: 47)
huDX182  YNEYKSYIYDWYFDF WGQGTLVTVSS  (SEQ ID No.: 48)
```

FIG. 2

Humanized DX182 Light Chain

Variable domain
DIQMTQSPSSLSASVGDRVTITCKASKNIRSYLAWYQQKPGKAPKLLIYSGSTLHS
GVPSRFSGSGSGTDFTLTISSLQPEDFATYYCQQHHEYPLTFGQGTKVEIKR Constant light domain (CL)
TVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC (SEQ ID No.: 49)

FIG. 3

Humanized DX182 Heavy Chain variable domain
QVQLQESGPGLVKPSETLSLTCTVSGYTITSGYDWSWIRQPPGKGLEWIG**YINYGG
STNYKPSLGSRVTISVDTSKNQFSLKLSSVTAADTAVYYCARYNEYKSYIYDWYFD**
FWGQGTLVTVSS CH1 domain
ASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSC Hinge-CH2-CH3 domain
DKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQKSLSLS
PGK
(SEQ ID No.: 50)

FIG. 4

Humanized DX182 Light Chain

12G8 signal peptide
```
 M   A   P   V   Q   L   L   G   L   L   V   L   F   L   P
ATG GCT CCA GTG CAG CTG CTG GGG CTG CTG GTG CTG TTC CTG CCA

A   M   R   C
GCC ATG AGA TGT
```

Heavy Chain
```
 D   I   Q   M   T   Q   S   P   S   S   L   S   A   S   V
GAT ATC CAG ATG ACC CAG TCT CCA TCC TCC CTG TCT GCC TCT GTG G   D   R   V   T   I   T   C   K   A   S   K   N   I   R
GGC GAC AGA GTG ACC ATC ACC TGC AAG GCC AGC AAG AAC ATC CGG S   Y   L   A   W   Y   Q   Q   K   P   G   K   A   P   K
AGC TAC CTG GCC TGG TAT CAG CAG AAG CCA GGG AAG GCC CCT AAG L   L   I   Y   S   G   S   T   L   H   S   G   V   P   S
CTG CTG ATC TAT TCT GGC TCC ACC CTG CAC TCT GGG GTG CCA TCC R   F   S   G   S   G   S   G   T   D   F   T   L   T   I
AGG TTC AGC GGC AGC GGC TCT GGG ACA GAC TTC ACC CTG ACC ATC S   S   L   Q   P   E   D   F   A   T   Y   Y   C   Q   Q
AGC AGC CTG CAG CCT GAG GAC TTC GCC ACC TAC TAC TGT CAG CAG H   H   E   Y   P   L   T   F   G   Q   G   T   K   V   E
CAC CAC GAG TAT CCA CTG ACC TTC GGC CAG GGC ACC AAG GTG GAG I   K   R   T   V   A   A   P   S   V   F   I   F   P   P
ATC AAG CGT ACG GTG GCT GCA CCA TCT GTG TTC ATC TTC CCT CCA S   D   E   Q   L   K   S   G   T   A   S   V   V   C   L
TCT GAT GAG CAG CTG AAG TCT GGA ACT GCC TCC GTG GTG TGC CTG L   N   N   F   Y   P   R   E   A   K   V   Q   W   K   V
CTG AAT AAC TTC TAT CCC AGA GAG GCC AAG GTG CAG TGG AAG GTG D   N   A   L   Q   S   G   N   S   Q   E   S   V   T   E
GAT AAC GCC CTC CAG AGC GGC AAC TCC CAG GAG AGC GTG ACA GAG
```

FIG. 5A

```
Q   D   S   K   D   S   T   Y   S   L   S   S   T   L   T
CAG GAC AGC AAG GAC AGC ACC TAC AGC CTG AGC AGC ACC CTG ACC

L   S   K   A   D   Y   E   K   H   K   V   Y   A   C   E
CTG AGC AAA GCA GAC TAC GAG AAA CAC AAG GTG TAC GCC TGC GAG

V   T   H   Q   G   L   S   S   P   V   T   K   S   F   N
GTG ACC CAT CAG GGC CTG AGC AGC CCC GTG ACA AAG AGC TTC AAC

R   G   E   C   *        (SEQ ID NO.: 51)
AGG GGA GAG TGT TAA      (SEQ ID NO.: 52)
```

FIG. 5B

Humanized DX182 Heavy Chain

12G8 sigpep
```
 M   A   V   L   G   L   L   F   C   L   V   T   F   P
ATG GCT GTG CTG GGG CTG CTG TTC TGC CTG GTG ACA TTC CCA

S   C   V   L   S
AGC TGT GTG CTG TCC
```

Heavy chain
```
 Q   V   Q   L   Q   E   S   G   P   G   L   V   K   P
CAG GTG CAG CTG CAG GAA TCT GGA CCC GGA CTG GTG AAG CCT S   E   T   L   S   L   T   C   T   V   S   G   Y   T
TCC GAA ACA CTG AGC CTG ACA TGT ACA GTG TCT GGC TAC ACA I   T   S   G   Y   D   W   S   W   I   R   Q   P   P
ATC ACC AGC GGC TAC GAC TGG AGC TGG ATC AGA CAG CCA CCT G   K   G   L   E   W   I   G   Y   I   N   Y   G   G
GGC AAG GGG CTG GAG TGG ATC GGC TAT ATC AAC TAC GGC GGA S   T   N   Y   K   P   S   L   G   S   R   V   T   I
TCC ACC AAC TAC AAG CCT TCC CTG GGC AGC AGA GTC ACC ATC S   V   D   T   S   K   N   Q   F   S   L   K   L   S
TCC GTG GAC ACA TCC AAG AAC CAG TTT AGC CTG AAG CTG AGC S   V   T   A   A   D   T   A   V   Y   Y   C   A   R
AGC GTG ACA GCC GCT GAC ACC GCC GTG TAT TAC TGT GCC AGA Y   N   E   Y   K   S   Y   I   Y   D   W   Y   F   D
TAC AAC GAG TAC AAG AGC TAC ATC TAC GAC TGG TAC TTC GAC F   W   G   Q   G   T   L   V   T   V   S   S   A   S
TTC TGG GGC CAG GGC ACC CTG GTG ACC GTG TCC AGC GCT AGC T   K   G   P   S   V   F   P   L   A   P   S   S   K
ACC AAG GGC CCA TCG GTC TTC CCC CTG GCA CCC TCC TCC AAG
```

FIG. 6A

```
  S    T    S    G    G    T    A    A    L    G    C    L    V    K
AGC  ACC  TCT  GGG  GGC  ACA  GCG  GCC  CTG  GGC  TGC  CTG  GTC  AAG

D    Y    F    P    E    P    V    T    V    S    W    N    S    G
GAC  TAC  TTC  CCC  GAA  CCG  GTG  ACG  GTG  TCG  TGG  AAC  TCA  GGC

A    L    T    S    G    V    H    T    F    P    A    V    L    Q
GCC  CTG  ACC  AGC  GGC  GTG  CAC  ACC  TTC  CCG  GCT  GTC  CTA  CAG

S    S    G    L    Y    S    L    S    S    V    V    T    V    P
TCC  TCA  GGA  CTC  TAC  TCC  CTC  AGC  AGC  GTG  GTG  ACC  GTG  CCC

S    S    S    L    G    T    Q    T    Y    I    C    N    V    N
TCC  AGC  AGC  TTG  GGC  ACC  CAG  ACC  TAC  ATC  TGC  AAC  GTG  AAT

H    K    P    S    N    T    K    V    D    K    K    V    E    P
CAC  AAG  CCC  AGC  AAC  ACC  AAG  GTG  GAC  AAG  AAA  GTT  GAG  CCC

K    S    C    D    K    T    H    T    C    P    P    C    P    A
AAA  TCT  TGT  GAC  AAA  ACT  CAC  ACA  TGC  CCA  CCG  TGC  CCA  GCA

P    E    L    L    G    G    P    S    V    F    L    F    P    P
CCT  GAA  CTC  CTG  GGG  GGA  CCG  TCA  GTC  TTC  CTC  TTC  CCC  CCA

K    P    K    D    T    L    M    I    S    R    T    P    E    V
AAA  CCC  AAG  GAC  ACC  CTC  ATG  ATC  TCC  CGG  ACC  CCT  GAG  GTC

T    C    V    V    V    D    V    S    H    E    D    P    E    V
ACA  TGC  GTG  GTG  GTG  GAC  GTG  AGC  CAC  GAA  GAC  CCT  GAG  GTC

K    F    N    W    Y    V    D    G    V    E    V    H    N    A
AAG  TTC  AAC  TGG  TAC  GTG  GAC  GGC  GTG  GAG  GTG  CAT  AAT  GCC

K    T    K    P    R    E    E    Q    Y    N    S    T    Y    R
AAG  ACA  AAG  CCG  CGG  GAG  GAG  CAG  TAC  AAC  AGC  ACG  TAC  CGT

V    V    S    V    L    T    V    L    H    Q    D    W    L    N
GTG  GTC  AGC  GTC  CTC  ACC  GTC  CTG  CAC  CAG  GAC  TGG  CTG  AAT
```

FIG. 6B

```
G   K   E   Y   K   C   K   V   S   N   K   A   L   P
GGC AAG GAG TAC AAG TGC AAG GTC TCC AAC AAA GCC CTC CCA

A   P   I   E   K   T   I   S   K   A   K   G   Q   P
GCC CCC ATC GAG AAA ACC ATC TCC AAA GCC AAA GGG CAG CCC

R   E   P   Q   V   Y   T   L   P   P   S   R   D   E
CGA GAA CCA CAG GTG TAC ACC CTG CCC CCA TCC CGG GAT GAG

L   T   K   N   Q   V   S   L   T   C   L   V   K   G
CTG ACC AAG AAC CAG GTC AGC CTG ACC TGC CTG GTC AAA GGC

F   Y   P   S   D   I   A   V   E   W   E   S   N   G
TTC TAT CCC AGC GAC ATC GCC GTG GAG TGG GAG AGC AAT GGG

Q   P   E   N   N   Y   K   T   T   P   P   V   L   D
CAG CCG GAG AAC AAC TAC AAG ACC ACG CCT CCC GTG CTG GAC

S   D   G   S   F   F   L   Y   S   K   L   T   V   D
TCC GAC GGC TCC TTC TTC CTC TAC AGC AAG CTC ACC GTG GAC

K   S   R   W   Q   Q   G   N   V   F   S   C   S   V
AAG AGC AGG TGG CAG CAG GGG AAC GTC TTC TCA TGC TCC GTG

M   H   E   A   L   H   N   H   Y   T   Q   K   S   L
ATG CAT GAG GCT CTG CAC AAC CAC TAC ACG CAG AAG AGC CTC

S   L   S   P   G   K   *              (SEQ ID NO.: 53)
TCC CTG TCT CCG GGT AAA TGA            (SEQ ID NO.: 54)
```

FIG. 6C

HEAVY VARIABLE DOMAIN

DX248  QVQLQQPGSELVRPGVSVKLSCKAS GYTFTSYWMH WVKQRHGQGLEWIG NIYPGSGSTNYDEKFKS KGTLTVDTSSSTAYMHLSSLTSEDSAVYYCTT
GTGAY WGQGTLVTVSA huDX248 QVQLVQSGAEVKKPGASVKVSCKAS GYTFTSYWMH WVRQAPGQGLEWMG NIYPGSGSTNYDEKFKS RVTMTDTSTSTAYMELRSLRSDDTAVYYCAR (SEQ ID NO.: 57)
GTGAY WGQGTLVTVSS

LIGHT VARIABLE DOMAIN

DX248  DVQMIQSPSSLSASLGDIVTMTC QASQGTSINLN WFQQKPGKAPKLLIY SANNLED GVPSRFSGSGFGTDFTLTISSLEDEDMATYFC LQITYLPWT
FGGGTKLEI huDX248 DIQMTQSPSSLSASVGDRVTITC QASQGTSINLN WYQQKPGKAPKLLIY SANNLED GVPSRFSGSGSGTDFTLTISSLQPEDFATYYC LQITYLPWT (SEQ ID NO.: 56)
FGQGTKVEIKRT

FIG. 9

INHIBITION OF DEGRANULATION:

FLOW CYTOMETRY:

|  |  | 1 | V domain | 50 |
|---|---|---|---|---|
| hu RLa | (1) | -------MSAPRLLISIIIMVSASSSS | CMGGKQMTQNYSTIFAEGNISQP | |
| chimp RLa | (1) | -------MSAPRLLISIIIMVPASSSS | CMGGKQMTQNYSTIFAEGNISQP | |
| rhesus RLa | (1) | -------MSASRLLISIIIMVSASSSS | CMDGKQMTQNYSKMSAEGNISQP | |
| cyno RLa | (1) | -------MSASRLLISIIIMVSASSSS | CMDGKQMTQNYSKMSAEGNISQP | |
| cyno CD200R | (1) | MLCPWRTANLGLLLILAVFLVAASNSL | CMDEKQITQNHSKVLAEVNISWP | |
| hu CD200R | (1) | MLCPWRTANLGLLLILTIFLVAASSSL | CMDEKQITQNYSKVLAEVNTSWP | |

|  |  | 51 | | 100 |
|---|---|---|---|---|
| hu RLa | (44) | VLMDINAVLCCPPIALRNLIIITWEIIL | RGQPSCTKAYKKETNETKETNC | |
| chimp RLa | (44) | VLMDTNAVLCCTPIALRNLIIITWEIIL | RGQPSCTKAYKKETNETKETNC | |
| rhesus RLa | (44) | VLMDTNAMLCCPPIEFRNLILIVWEIII | RGQPSCTKAYRKETNETKETNC | |
| cyno RLa | (44) | VLMDTNAMLCCPPIEFRNLIVIVWEIII | RGQPSCTKAYRKETNETKETNC | |
| cyno CD200R | (51) | VQMARNAVLCCPPIEFRNLIVITWEIIL | RGQPSCTKTYRKDTNETKETNC | |
| hu CD200R | (51) | VKMATNAVLCCPPIALRNLIIITWEIIL | RGQPSCTKAYRKETNETKETNC | |

|  |  | 101 | | 150 |
|---|---|---|---|---|
| hu RLa | (94) | TVERITWVSRPDQNSDLQILPVDTTHDGYYRGIVVTPDGNFHRGYHLQVL | | |
| chimp RLa | (94) | TAERITWVSRPDQNSDLQIRPVDTTHDGYYRGIVVTPDGNFHRGYHLQVL | | |
| rhesus RLa | (94) | TDKRITWVSTPDQNSDLQIHPVAITHDGYYRCIMATPDGNFHHGYHLQVL | | |
| cyno RLa | (94) | TDKRITWVSTPDQNSDLQIHPVAITHDGYYRCIMATPDGNFHRGYHLQVL | | |
| cyno CD200R | (101) | TDERITWVSTPDQNSDLQIHPVAITHDGYYRCIMATPDGNFHRGYHLQVL | | |
| hu CD200R | (101) | TDERITWVSRPDQNSDLQIRPVAITHDGYYRCIMVTPDGNFHRGYHLQVL | | |

|  |  | 151 |  ◇  | 200 |
|---|---|---|---|---|
| hu RLa | (144) | VTPEVNLFQSRNITAVCKAVTGKPAAQISWIPEGSILATKQEYWGNGTVT | | |
| chimp RLa | (144) | VTPEVTLFQSWNRTAVCKAVTGKPAAQISWIPEGSILATKQEYWGNGTVT | | |
| rhesus RLa | (144) | VTPEVTLFQSRNRTAVCKAVAGKPAAQISWIPAGNCAPTEHEYWGNGTVT | | |
| cyno RLa | (144) | VTPEVTLFQSRNRTAVCKAVAGKPAAQISWIPAGDCAPTEHEYWGNGTVT | | |
| cyno CD200R | (151) | VTPEVTLFESRNRTAVCKAVAGKPAAQISWIPAGDCAPTEQEYWGNGTVT | | |
| hu CD200R | (151) | VTPEVTLFQNRNRTAVCKAVAGKPAAQISWIPEGDCA-TKQEYWSNGTVT | | |

|  |  | 201 |  ◇  | 250 |
|---|---|---|---|---|
| hu RLa | (194) | VKSTCPWEGH-KSTVTCHVSHLTGNKSLSVKLNSGLRTSGSPALSLLIIL | | |
| chimp RLa | (194) | VKSTCPWEGH-KSTVTCHVSHLTGNKSLSVKVNSGLRTSGSPALSLLIIL | | |
| rhesus RLa | (194) | VESMCHWGDHNASTVTCHVSHLTGNKSLYIKLNSGLRTSGSPALDLLIIL | | |
| cyno RLa | (194) | VESMCHWGDHNASTVTCHVSHLTGNKSLYIKLNSGLRTSGSPALDLLIIL | | |
| cyno CD200R | (201) | VKSTCHWEGHNVSTVTCHVSHLTGNKSLYIELLP--VP-GAKKS--AKLY | | |
| hu CD200R | (200) | VKSTCHWEVHNVSTVTCHVSHLTGNKSLYIELLP--VP-GAKKS--AKLY | | |

|  |  | 251 | | 300 |
|---|---|---|---|---|
| hu RLa | (243) | YVKLSLFVVILVTTGFVFFQRINHVRKVL-------------------- | | |
| chimp RLa | (243) | YVKLSLFVVILVTTGFVFFQRINHVRKVL-------------------- | | |
| rhesus RLa | (244) | YVKLSLFVVILVTTGFVFFQRINYVRKSL-------------------- | | |
| cyno RLa | (244) | YVKLSLFVVILVTTGFVFFQRINYVRKSL-------------------- | | |
| cyno CD200R | (246) | MPYVILTIIILTIVGFIWLLKISGCRKYNLNKTESTSVVEEDEMQPYASY | | |
| hu CD200R | (245) | IPYIILTIIILTIVGFIWLLKVNGCRKYKLNKTESTPVVEEDEMQPYASY | | |

|  |  | 301 | 332 |
|---|---|---|---|
| hu RLa | (272) | -------------------------------- | |
| chimp RLa | (272) | -------------------------------- | |
| rhesus RLa | (273) | -------------------------------- | |
| cyno RLa | (273) | -------------------------------- | |
| cyno CD200R | (296) | TEKNNPLYDTTNKVKASQALQSEVGTDLHTL- | |
| hu CD200R | (295) | TEKNNPLYDTTNKVKASEALQSEVDTDLHTL- | |

◇ CYSTEINES CRITICAL FOR CELL SURFACE EXPRESSION

FIG. 13

DX182 binds to Cynomolgus CD200RLa
Mouse mast cells and Baf/3-Dap12 were transfected with Cynomolgus CD200RLa
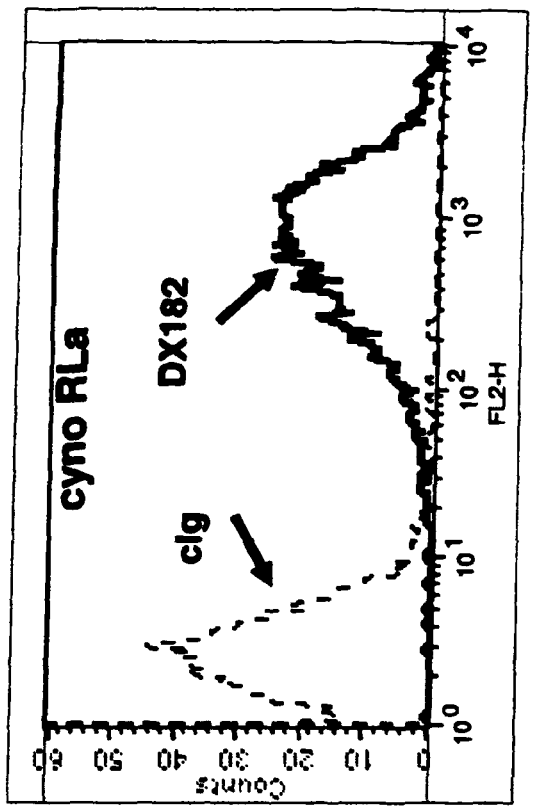
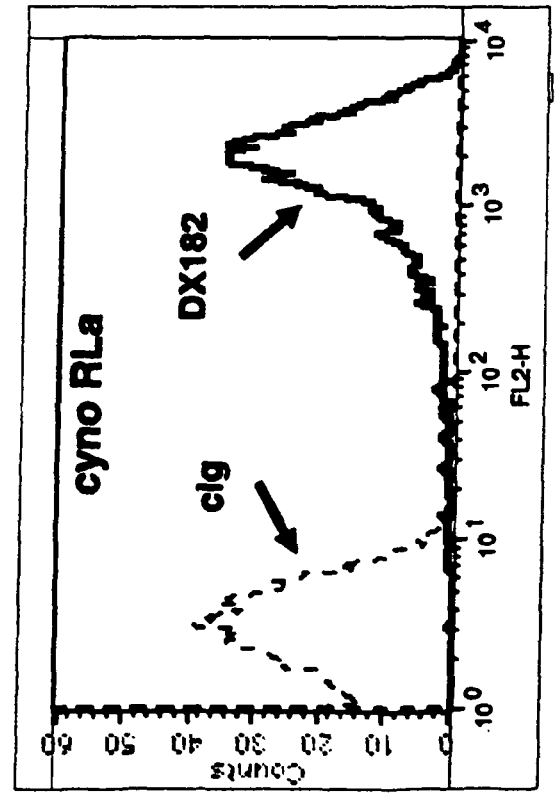
Fig. 14

ANTIBODIES TO CD200R

REFERENCE TO CROSS RELATED APPLICATIONS

This application is the national stage application under 35 U.S.C. 371 of International Patent Application No.: PCT/US2007/026202 filed Dec. 20, 2007, which claims the benefit of priority under 35 USC 119(e) of provisional patent application U.S. Ser. No.: 60/876,618 filed Dec. 22, 2006, the disclosure of which is hereby incorporated by reference in its entirety.

FIELD OF THE INVENTION

The present invention relates generally to binding compounds specific for the human inhibitory CD200R and uses thereof. More specifically, the invention relates to antibodies that recognize the human inhibitory CD200R(CD200 receptor) and modulate its activity, particularly in inflammatory and autoimmune disorders.

BACKGROUND OF THE INVENTION

The immune system functions to protect individuals from infective agents, e.g., bacteria, multi-cellular organisms, and viruses, as well as from cancers. This system includes several types of lymphoid and myeloid cells such as monocytes, macrophages, dendritic cells (DCs), eosinophils, T cells, B cells, and neutrophils. These lymphoid and myeloid cells often produce signaling proteins known as cytokines. The immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration. Immune response can produce pathological consequences, e.g., when it involves excessive inflammation, as in the autoimmune disorders (see, e.g., Abbas et al. (eds.) (2000) *Cellular and Molecular Immunology*, W.B. Saunders Co., Philadelphia, Pa.; Oppenheim and Feldmann (eds.) (2001) *Cytokine Reference*, Academic Press, San Diego, Calif.; von Andrian and Mackay (2000) *New Engl. J. Med.* 343:1020-1034; Davidson and Diamond (2001) *New Engl. J. Med.* 345:340-350).

Myeloid cells (i.e., macrophages, dendritic cells (DC), neutrophils, mast cells, and eosinophils) play important roles in maintaining chronic inflammation (Kinne, R. W., et al (2000) *Arthritis Res.* 2:189-202; Kiefer, R. B. et al (2001) *Progr. Neurobiol.* 64:109-127; O'Shea, J. J. et al (2002) *Nat. Rev. Immunol.* 2:37-45; Hamid, Q. et al (2003) *J. Allergy Clin. Immunol.* 111: S5-S12; Liu, H. et al (2004) *Rheum Dis. Clin. North Am.* 30:19-39). They can be regulated through cell-cell interactions that trigger matched sets of activating in inhibitory receptors, in addition to being regulated by secreted factors (Barclay, A. N. et al (2002) *Trends in Immunol.* 23: 285-290). The regulation of myeloid cell activity by direct cell-cell contact allows a more localized control than that mediated by cytokines. The CD200-CD200R interaction also provides a cell-cell contact regulatory interaction for myeloid cells. The widely expressed glycoprotein CD200 is closely related structurally to the T cell costimulatory molecules CD80 and CD86 and is genetically linked to them on human chromosome 3 and mouse chromosome 16 (McCaughan, G. W. (1987) *Immunogenetics* 25:133-135; Borriello, F. et al (1998) *Mamm. Genome* 9:114-118). Structurally, CD200 contains two Ig superfamily (IgSF) domains in a typical V/C2 arrangement (Clark, M. J. et al (1985) *EMBO J* 4:113-118).

The CD200R is expressed at the surface of human and mouse myeloid cells, such as macrophages, DCs, neutrophils, and mast cells, and also on T cells (Wright, G. J. et al (2000) *Immunity* 12:233-242; Wright, G. J. et al (2003) *J. Immunol.* 171:3034-3046). CD200R is structurally related to CD200, located on the same chromosome, the genes probably evolved by gene duplication (Wright, G. J. et al (2003) *J. Immunol.* 171:3034-3046). However, CD200R is distinct from CD200 and displays a longer cytoplasmic tail containing three conserved tyrosine residues, one of which is contained with an NPXY motif (Wright, G. J. et al (2000) *Immunity* 12:233-242; Wright, G. J. et al (2003) *J. Immunol.* 171:3034-3046). Upon ligand or agonist antibody binding, CD200R is phosphorylated on the tyrosine of the NPXY motif and subsequently binds adapter proteins Dok1 and Dok2. Phosphorylation of these adapter proteins recruits SHIP and RasGAP, which subsequently inhibits the Ras/MAPK activation pathways (Zhang, S. et al. 2004, J. Immunol. 173:6786-6793).

The CD200 receptor (CD200R) has now been cloned from a variety of species including rats, mice, humans and several non-human primates. CD200R is located on human chromosome 3q12-13 and on mouse chromosome 16 and both human and mouse CD200R show high degrees of similarities in sequence and structure (Wright, G. J. et al (2003) *J. Immunol.* 171:3034-3046). In addition to CD200R, four related genes have been identified in the mouse (Wright, G. J. et al (2003) *J. Immunol.* 171:3034-3046). These genes were termed CD200RL (CD200R-like), and have been shown to associate with the activating adaptor protein, DAP12 (Lanier, L. L. (1998) *Nature* 39:703). DAP12 is required for cell surface expression of these receptors and for signal transduction. Dap12 is a potent activating adaptor protein that contains a classic immune tyrosine-based activation motif (ITAM), and thus the mouse CD200RL genes are myeloid activating genes. Mouse mast cells express these activating CD200RL receptors and they can be triggered using receptor specific antibodies to generate potent degranulation responses similar in magnitude to that observed with FcξRI activation. Although these additional CD200R family member genes have been termed CD200R-like based on sequence homology to the extracellular domain of CD200R, they do not bind CD200 and at present the ligand(s) for these additional receptors remains unknown (Hatherly D. et al (2005) *J Immunol* 175(4):2469-74). In addition some outbreed strains of mice express CD200RLe, a CD200R family member with homology to CD200R (Hatherly D. et al (2005) Journal of Immunology 175: 2469-2474). In contrast to the mouse CD200R family, the human genome showed only two CD200R family members: CD200R and CD200RLa (Wright, G. J. et al (2003) *J. Immunol.* 171:3034-3046)

The need exists for agonists of the human inhibitory CD200R, such as anti-human inhibitory CD200R monoclonal antibodies, for use in treatment of human disorders, such as inflammatory or autoimmune disorders. Such agonists will preferably exhibit low immunogenicity in human subjects, allowing for repeated administration without adverse immune responses.

SUMMARY OF THE INVENTION

The present invention generally provides binding compounds specific for the human inhibitory CD200R and uses thereof. More specifically, the invention provides antibodies that specifically recognize the human inhibitory CD200R and having one or more desirable properties, including agonist activities, high binding affinities, good pharmacokinetics and low antigenicity in human subjects. The invention also provides methods of use of the antibodies of the present invention in the treatment of disease.

Accordingly, in one embodiment the present invention provides a binding compound, for example an antibody molecule or binding fragment thereof, that specifically binds the human inhibitory CD200R receptor and activates the human inhibitory CD200R. In some embodiments, the binding compound comprises at least one antibody light chain variable ($V_L$) domain and at least one antibody heavy chain variable ($V_H$) domain, or binding fragments of these domains, wherein the $V_L$ domain comprises at least a specified number of complementarity determining regions (CDRs) having a sequence selected from SEQ ID NOs: 1-18, and the $V_H$ domain comprises at least at least a specified number of CDRs having a sequence selected from SEQ ID NOs: 19-36, wherein the specified number is one, two or three. The specified number of CDRs may be the same or different for the light and heavy chain variable domains in any given binding compound. In another embodiment, the $V_L$ domain CDRs are selected from SEQ ID NOs: 1, 2 and 3. In yet another embodiment, the $V_H$ domain CDRs are selected from SEQ ID NOs: 19, 20 and 21. In another embodiment the $V_L$ domain CDRs are selected from RASKNIRSYLA (SEQ ID No.: 55), SEQ ID NO: 2 and SEQ ID NO: 3 and the $V_H$ domain CDRs are selected from SEQ ID NOs: 19, 20 and 21. In another embodiment the $V_L$ domain CDRs are selected from SEQ ID NOs: 16, 17 and 18 and the $V_H$ domain CDRs are selected from SEQ ID NOs: 34, 35 and 36. In a further embodiment, the sequences of the $V_L$ and $V_H$ domains are the sequences of SEQ ID NOs: 42 and 48, respectively. In yet another further embodiment the sequences of the $V_L$ and $V_H$ domains are the sequences of SEQ ID NOs: 56 and 57 respectively (see FIG. 9). In a preferred embodiment, the CD200R binding compound activates the inhibitory activity of the human inhibitory CD200R receptor.

In other embodiments, the binding compound comprises at least one $V_L$ domain and at least one $V_H$ domain, or binding fragments of these domains, wherein the $V_L$ domain comprises one, two or three CDRs having a sequence selected from SEQ ID NOs: 1-18, and the $V_H$ domain comprises one, two or three CDRs having a sequence selected from SEQ ID NOs: 19-36. In another embodiment, the sequence of the $V_L$ and $V_H$ domains are the sequences of SEQ ID NOs: 42 and 48, respectively. In yet another further embodiment the sequences of the $V_L$ and $V_H$ domains are the sequences of SEQ ID NOs: 56 and 57 respectively. In another embodiment, the binding compound has the same CDRs as the antibody encoded by the expression vector deposited with the American Tissue Culture Collection (ATCC) (Manassas, Va. USA) on Dec. 6, 2006 and having ATCC Accession No. PTA-8067. In another embodiment, the binding compound has the same CDRs as the antibody produced from the hybridoma having ATCC Accession No. PTA-8838, deposited as strain HC809.14F12.6.DX248.3 on Dec. 13, 2007.

In a further embodiment, the binding compound comprises at least one $V_L$ domain and at least one $V_H$ domain, or binding fragments of these domains, wherein the $V_L$ domain comprises one, two or three CDRs having a sequence selected from SEQ ID NOs: 37-42, and the $V_H$ domain comprises one, two or three CDRs having a sequence selected from SEQ ID NOs: 43-48.

In various other embodiments, the present invention provides a binding compound that binds to human inhibitory CD200R that has $V_L$ and $V_H$ domains with at least 95%, 90%. 85%, 80%, 75% or 50% sequence homology with the sequences of SEQ ID NOs: 42 and 48, respectively. In other embodiments, the present invention provides a binding compound that binds to human inhibitory CD200R that has $V_L$ and $V_H$ domains with at least 95%, 90%. 85%, 80%, 75% or 50% sequence homology with the sequences of SEQ ID NOs: 56 and 57, respectively. In other embodiments the binding compound of the present invention comprises $V_L$ and $V_H$ domains having up to 0, 1, 2, 3, 4, 5, 6, 7, 8, 9, 10 or more conservative amino acid substitutions with reference to the sequences of SEQ ID NOs: 42 and 48, respectively. In another embodiment, the binding compound of the present invention is an antibody having a light chain and a heavy chain with up to 0, 1, 2, 3, 4, 5, 6, 7, 8, 9, 10 or more conservative amino acid substitutions with reference to the sequences of SEQ ID NOs: 49' and 50, respectively. In another embodiment, the binding compound of the present invention is an antibody having a light chain and a heavy chain with up to 0, 1, 2, 3, 4, 5, 6, 7, 8, 9, 10 or more conservative amino acid substitutions with reference to the sequences of SEQ ID NOs: 56 and 57, respectively.

In one embodiment, the binding compound is an antibody or binding fragment thereof, e.g. an antibody fragment selected from the group consisting of Fab, Fab', Fab'-SH, Fv, scFv, F(ab')$_2$, and a diabody. In one embodiment, the binding compound of the present invention is antibody huDX182 comprising a light chain having the sequence of SEQ ID NO.: 49 and a heavy chain having the sequence of SEQ ID NO.: 50. In another embodiment, the binding compound is the mature antibody produced from the expression vector having ATCC Accession No. PTA-8067 (huDX182 with signal sequence in pACD200RV1 plasmid) deposited Dec. 6, 2006 with the ATCC (Manassas, Va. USA). In another embodiment, the binding compound has the same CDRs as the antibody produced from the hybridoma having ATCC Accession No. PTA-8838, deposited as strain HC809.14F12.6.DX248.3 on Dec. 13, 2007.

In one embodiment, the binding compound of the present invention comprises a heavy chain constant region, for example a human constant region, such as γ1, γ2, γ3, or γ4 human heavy chain constant region or a variant thereof. In another embodiment, the binding compound comprises a light chain constant region, for example a human light chain constant region, such as lambda or kappa human light chain region or variant thereof.

In another embodiment, the invention relates to an isolated nucleic acid, for example DNA, encoding a binding compound of the present invention, for example an antibody (or binding fragment thereof) that binds to human inhibitory CD200R. In one embodiment, the isolated nucleic acid encodes a binding compound comprising at least one antibody light chain variable ($V_L$) domain and at least one antibody heavy chain variable ($V_H$) domain, or binding fragments of these domains, wherein the $V_L$ domain comprises at least a specified number of complementarity determining regions (CDRs) having a sequence selected from SEQ ID NOs: 1-18, and the $V_H$ domain comprises at least at least a specified number of CDRs having a sequence selected from SEQ ID NOs: 19-36 wherein the specified number is one, two or three.

In another embodiment, the isolated nucleic acid encodes the light and heavy chain variable region sequences of SEQ ID NOs: 42 and 48, respectively. In yet another embodiment, the isolated nucleic acid encodes antibody huDX182 comprising a light chain having the sequence of SEQ ID NO.: 49 and a heavy chain having the sequence of SEQ ID NO.: 50. In another embodiment, the isolated nucleic acid encodes the light and heavy chain variable region sequences of SEQ ID NOs: 41 and 47, respectively. In yet another embodiment, the isolated nucleic acid encodes antibody a huDX248 comprising a light chain having the sequence of SEQ ID NO.: 56 and a heavy chain having the sequence of SEQ ID NO.: 57. In some embodiments the isolated nucleic acid encodes both a light chain and a heavy chain on a single nucleic acid molecule, and in other embodiments the light and heavy chains are encoded on two or more separate nucleic acid molecules. In another embodiment the nucleic acids further encodes a signal sequence. In one embodiment the nucleic acids are SEQ ID NOS. 52 and 54.

In further embodiments, the present invention relates to expression vectors comprising the isolated nucleic acids of the invention, wherein the nucleic acid is operably linked to control sequences that are recognized by a host cell when the host cell is transfected with the vector. In one embodiment, the expression vector has ATCC Accession No. PTA-8067 (huDX182 in plasmid with signal sequence in pACD200RV1 plasmid) deposited on Dec. 6, 2006 with the ATCC (Manassas, Va. USA). In another embodiment, the binding compound has the same CDRs as the antibody produced from the hybridoma having ATCC Accession No. PTA-8838, deposited as strain HC809.14F12.6.DX248.3 on Dec. 13, 2007.

In another embodiment, the invention relates to a host cell comprising an expression vector of the present invention. The invention further relates to methods of producing a binding compound of the present invention comprising culturing a host cell harboring an expression vector encoding the binding compound in culture medium, and isolating the binding compound from the host cell or culture medium.

The invention also relates to binding compounds, such as antibodies or binding fragments thereof, that bind to the same epitope on human inhibitory CD200R receptor as antibodies huDX182, DX182, DX185, DX 178, DX184 or DX248, for example antibodies that are able to cross-block binding of any of these antibodies of the present invention.

The invention relates to binding compounds, such as antibodies or binding fragments thereof, that are specific for the human inhibitory CD200R and able to activate the inhibitory activities of the human inhibitory CD200R and have equilibrium dissociation constants ($K_d$) of 1000, 500, 100, 50, 20, 10, 5, 2 pM or less (i.e. higher affinity). This invention also relates to binding compounds, such as antibodies or binding fragments thereof, that are specific for the human inhibitory CD200R and that inhibit mast cell degranulation with an $IC_{50}$ of 5000, 2000, 1000, 500 pM in a mast cell degranulation assay.

The invention also relates to methods of treating subjects, including human subjects, in need of treatment with the human inhibitory CD200R binding compounds of the present invention. Such subjects may have an inflammatory or autoimmune disorder, such as rheumatoid arthritis (RA), osteoarthritis, rheumatoid arthritis, osteoporosis, inflammatory fibrosis (e.g., scleroderma, lung fibrosis, and cirrhosis), inflammatory bowel disorders (e.g., Crohn's disease, ulcerative colitis and inflammatory bowel disease), asthma (including allergic asthma), allergies, COPD, multiple sclerosis, psoriasis, uveitis and cancer. Such methods of treatment may further comprise administering one or more additional therapeutic agents, such as immunosuppressive or anti-inflammatory agents. By way of example, and not limitation, RA, psoriasis, asthma, and allergy and uveitis are treated by the methods described herein. In a particularly preferred embodiment asthma and allergy are treated by the methods described herein.

In a further embodiment, the invention provides methods of treatment comprising administration of a therapeutically effective amount of an anti-human inhibitory CD200R antibody or binding fragment in combination with one or more other therapeutic agents. By way of example, and not limitation, the one or more therapeutic agents include IL-23, IL-1β, IL-6 and TGF-β (See, e.g., Veldhoen (2006) Immunity 24:179-189; Dong (2006) Nat. Rev. Immunol. 6(4):329-333) or a combination. In various embodiments the one or more other therapeutic agents is administered before, concurrently with, or after the anti-human inhibitory CD200R antibody or fragment.

The invention also relates to compositions and formulations of the binding compounds of the present invention, comprising the binding compound and a pharmaceutically acceptable carrier or diluent, and optionally one or more immunosuppressive or anti-inflammatory agents.

BRIEF DESCRIPTION OF THE DRAWINGS

FIG. 1 shows alignments of the light chain variable domains for the rat anti-human CD200R antibodies DX182 (SEQ ID NO: 37), DX185 (SEQ ID NO: 38), DX178 (SEQ ID NO: 39), DX184 (SEQ ID NO: 40), and the humanized rat anti-human CD200R antibody (SEQ ID NO: 42). DX248 is a mouse anti-cyno inhibitory CD200R (SEQ ID NO: 41). CDRs are indicated. Numbering is according to Kabat et al. (1991) "Sequences of Proteins of Immunological Interest", U.S. Department of Health and Human Services, NIH Pub. 91-3242, 5th Ed., referred to herein as "Kabat et al. (1991)".

FIG. 2 shows alignments of the heavy chain variable domains for the rat anti-human CD200R antibodies DX182 (SEQ ID NO: 43), DX185 (SEQ ID NO: 44), DX178 (SEQ ID NO: 45), DX184 (SEQ ID NO: 46), and the humanized rat anti-human CD200R antibody (SEQ ID NO: 48). DX248 is a mouse anti-cyno inhibitory CD200R (SEQ ID NO: 47). CDRs are indicated. Numbering is according to Kabat et al. (1991).

FIG. 3 shows the amino acid sequence (SEQ ID NO: 49) of the light chain of the humanized anti-human inhibitory CD200R antibody (huDX182).

FIG. 4 shows the amino acid sequence (SEQ ID NO: 50) of the heavy chain of the humanized anti-human inhibitory CD200R antibody (huDX182).

FIGS. 5A and 5B show a nucleic acid sequence (SEQ ID NO: 52) encoding a signal peptide and the light chain of the humanized anti-human inhibitory CD200R antibody (huDX182).

FIGS. 6A, 6B and 6C show a nucleic acid sequence (SEQ ID NO: 54) encoding a signal peptide and the light chain of the humanized anti-human inhibitory CD200R antibody (huDX182).

FIG. 9 illustrates sequences for a heavy (SEQ ID NO: 57) and light (SEQ ID NO: 56) variable domain for a humanized DX248

FIG. 13 shows the amino acid sequence alignment of human and non-human primate CD200R and CD200RLa genes. Diamonds indicate position of cysteine residues in extracellular domain which are important for cell surface expression of the receptors.

FIG. 14 shows DX182 binds to cynomolgus CD200RLa. Cynomolgus CD200RLa was cloned and transfected into mouse mast cells or mouse Baf/3 cells containing human Dap12. These transfectants were then stained with isotype control antibody or DX182 (anti-huCD200R). Both transfectants showed strong staining with the DX182 antibody indicating the DX182 was capable of recognizing cynomolgus CD200RLa.

DETAILED DESCRIPTION

I. Definitions

Figure 7:
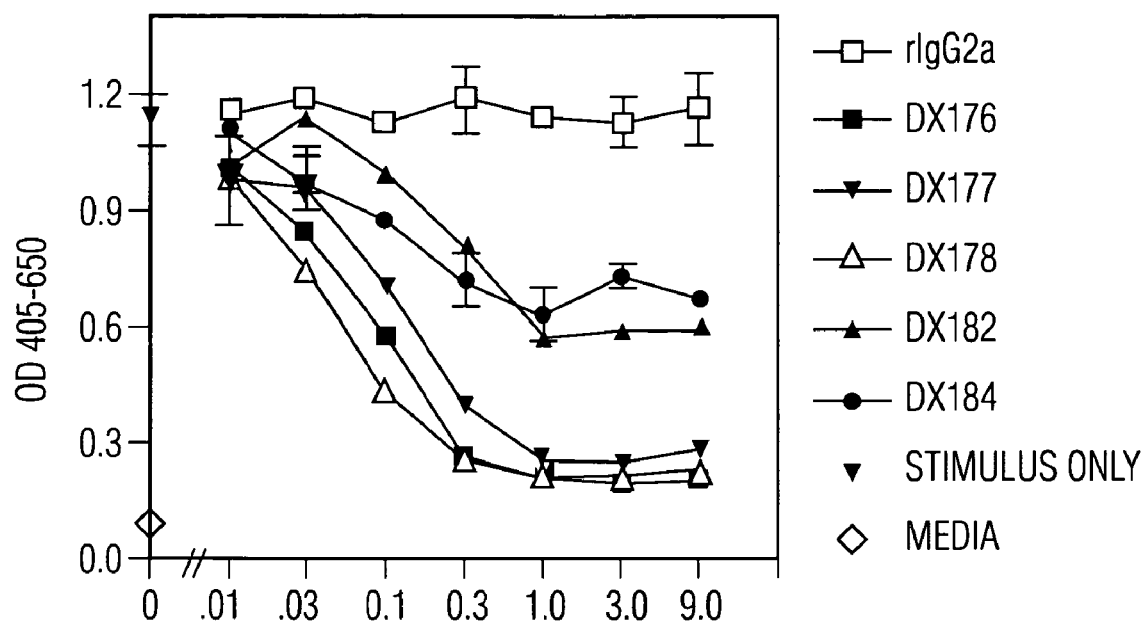
FIG. 7 shows the effects of anti-human CD200R antibodies DX176, DX177, DX178, DX182 and DX184 in a mast cell degranulation assay.

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems. "Proliferative activity" encompasses an activity that promotes, that is necessary for, or that is specifically associated with, e.g., normal cell division, as well as cancer, tumors, dysplasia, cell transformation, metastasis, and angiogenesis.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of a human inhibitory CD200R agonist a human or animal subject, a cell, tissue, physiological compartment, or physiological fluid. "Treatment of a cell" also encompasses situations where the human inhibitory CD200R agonist contacts human inhibitory CD200R receptor, e.g., in the fluid phase or colloidal phase, but also situations where the agonist does not contact the cell or the receptor.

"Treat" or "treating" means to administer a therapeutic agent, such as a composition containing any of the binding compounds of the present invention, internally or externally to a patient having one or more disease symptoms for which the agent has known therapeutic activity. Typically, the agent is administered in an amount effective to alleviate one or more disease symptoms in the treated patient or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient, and the ability of the drug to elicit a desired response in the patient. Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every patient, it should alleviate the target disease symptom(s) in a statistically significant number of patients as determined by any statistical test known in the art such as the Student's t-test, the chi²-test, the U-test according to Mann and Whitney, the Kruskal-Wallis test (H-test), Jonckheere-Terpstra-test and the Wilcoxon-test.

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies). As used herein, the terms "anti human inhibitory CD200R binding fragment or "binding fragment" of an antibody (the "parental antibody") encompass a fragment or a derivative of an antibody, typically including at least a portion of the antigen binding or variable regions (e.g. one or more CDRs) of the parental antibody, that retains at least some of the binding specificity of the parental antibody. Examples of antibody binding fragments include, but are not limited to, Fab, Fab', F(ab')$_2$, and Fv fragments; diabodies; linear antibodies; single-chain antibody molecules, e.g., sc-Fv; and multispecific antibodies formed from antibody fragments. Typically, a binding fragment or derivative retains at least 10% of its human inhibitory CD200R binding activity when that activity is expressed on a molar basis. Preferably, a binding fragment or derivative retains at least 20%, 50%, 70%, 80%, 90%, 95% or 100% or more of the human inhibitory CD200R binding affinity as the parental antibody. It is also intended that a human inhibitory CD200R binding fragment can include conservative amino acid substitutions (referred to as "conservative variants" of the antibody) that do not substantially alter its biologic activity. The term "binding compound" refers to both antibodies and binding fragments thereof.

A "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H2$ and $C_H3$ domains of an antibody. The two heavy chain fragments are held together by two or more disulfide bonds and by hydrophobic interactions of the CH3 domains.

A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H^2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

As used herein, unless otherwise indicated, an "anti-human inhibitory CD200R" antibody refers to an antibody that is raised against the human inhibitory CD200R or variant thereof, or any antigenic fragment thereof. In a preferred embodiment the "anti-human inhibitory CD200R antibody is an agonist antibody that activates the inhibitory activity of the human inhibitory CD200R. Examples of the inhibitory activity of the human inhibitory CD200R include, but are not limited to, inhibition of mast cell degranulation and cytokine secretion, inhibition of macrophage and dendritic cell antigen presentation and cytokine secretion. Anti-human inhibitory CD200R antibodies also refers to antibodies raised against the cyno-inhibitory CD200R (e.g., see FIG. 13) or variant thereof, or antigenic fragment thereof and which also bind the human inhibitory CD200R. In a preferred embodiment the anti-human inhibitory CD200R antibody raised against the cyno inhibitory CD200R is an agonist antibody that activates the inhibitory activity of the human inhibitory CD200R. Examples of the inhibitory activity of the human inhibitory CD200R include, but are not limited to, inhibition of mast cell degranulation and cytokine secretion, inhibition of macrophage and dendritic cell antigen presentation and cytokine The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., (1984) *Proc. Natl. Acad. Sci. USA* 81: 6851-6855).

As used herein, a "chimeric antibody" is an antibody having the variable domain from a first antibody and constant domain from a second antibody, where the first and second antibodies are from different species. Typically the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental rodent antibody.

The monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079, which are hereby incorporated by reference in their entireties). In one embodiment; the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, the term "humanized antibody" refers to forms of antibodies that contain sequences from both human and non-human (e.g., murine, rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

The antibodies of the present invention also include antibodies with modified (or blocked) Fc regions to provide altered effector functions. See, e.g., U.S. Pat. No. 5,624,821; WO2003/086310; WO2005/120571; WO2006/0057702. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, enabling less frequent dosing and thus increased convenience and decreased use of material. See Presta (2005) *J. Allergy Clin. Immunol.* 116:731 at 734-35.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only.

As used herein, the term "hypervariable region" refers to the amino acid residues of an antibody which are responsible for antigen-binding. The hypervariable region comprises amino acid residues from a "complementarity determining region" or "CDR" (i.e. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (CDRL1), 50-52 (CDRL2) and 91-96 (CDRL3) in the light chain variable domain and 26-32 (CDRH1), 53-55 (CDRH2) and 96-101 (CDRH3) in the heavy chain variable domain; Chothia and Lesk (1987) *J. Mol. Biol.* 196: 901-917). As used herein, the term "framework" or "FR" residues refers to those variable domain residues other than the hypervariable region residues defined herein as CDR residues.

"Binding substance" refers to a molecule, small molecule, macromolecule, antibody, a fragment or analogue thereof, or soluble receptor, capable of binding to a target. "Binding substance" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, that is capable of binding to a target. "Binding substance" may also refer to a molecule capable of binding to a target in combination with a stabilizer, excipient, salt, buffer, solvent, or additive. "Binding" may be defined as an association of the binding substance with a target where the association results in reduction in the normal Brownian motion of the binding substance, in cases where the binding substance can be dissolved or suspended in solution.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Various embodiments of the binding compounds of the present invention comprise polypeptide chains with sequences that include up to 0 (no changes), 1, 2, 3, 4, 5, 6, 7, 8, 9, 10, 12, 15, 20 or more conservative amino acid substitutions when compared with the specific amino acid sequences disclosed herein, e.g. SEQ ID NOs: 2, 4, 5, or 6. As used herein, the phrase "up to X" conservative amino acid substitutions includes 0 substitutions and any number of substitutions up to and including X substitutions. Such exemplary substitutions are preferably made in accordance with those set forth in Table 2 as follows:

TABLE 1

Exemplary Conservative Amino Acid Substitutions

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

The terms "consists essentially of," or variations such as "consist essentially of or "consisting essentially of," as used throughout the specification and claims, indicate the inclusion of any recited elements or group of elements, and the optional inclusion of other elements, of similar or different nature than the recited elements, which do not materially change the basic or novel properties of the specified dosage regimen, method, or composition. As a nonlimiting example, a binding compound which consists essentially of a recited amino acid sequence may also include one or more amino acids that do not materially affect the properties of the binding compound.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side affects (see, e.g., U.S. Pat. No. 5,888,530 issued to Netti, et al.). An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

"Exogenous" refers to substances that are produced outside an organism, cell, or human body, depending on the context. "Endogenous" refers to substances that are produced within a cell, organism, or human body, depending on the context.

"Homology" refers to sequence similarity between two polynucleotide sequences or between two polypeptide sequences. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous when the sequences are optimally aligned then the two sequences are 60% homologous. Generally, the comparison is made when two sequences are aligned to give maximum percent homology.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

"Inflammatory disorder" means a disorder or pathological condition where the pathology results, in whole or in part, from, e.g., a change in number, change in rate of migration, or change in activation, of cells of the immune system. Cells of the immune system include, e.g., T cells, B cells, monocytes or macrophages, antigen presenting cells (APCs), dendritic cells, microglia, NK cells, NKT cells, neutrophils, eosinophils, mast cells, or any other cell specifically associated with the immunology, for example, cytokine-producing endothelial or epithelial cells.

"Isolated binding compound" refers to the purification status of a binding compound and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific piece of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, the term "germline sequence" refers to a sequence of unrearranged immunoglobulin DNA sequences. Any suitable source of unrearranged immunoglobulin may be used.

"Inhibitors" and "antagonists," or "activators" and "agonists," refer to inhibitory or activating molecules, respectively, e.g., for the activation of, e.g., a ligand, receptor, cofactor, a gene, cell, tissue, or organ. A modulator of, e.g., a gene, a receptor, a ligand, or a cell, is a molecule that alters an activity of the gene, receptor, ligand, or cell, where activity can be activated, inhibited, or altered in its regulatory properties. The modulator may act alone, or it may use a cofactor, e.g., a protein, metal ion, or small molecule. Inhibitors are compounds that decrease, block, prevent, delay activation, inactivate, desensitize, or down regulate, e.g., a gene, protein, ligand, receptor, or cell. Activators are compounds that increase, activate, facilitate, enhance activation, sensitize, or up regulate, e.g., a gene, protein, ligand, receptor, or cell. An inhibitor may also be defined as a compound that reduces, blocks, or inactivates a constitutive activity. An "agonist" is a compound that interacts with a target to cause or promote an increase in the activation of the target. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist. By way of example, and not limitation, an agonist antibody is an antibody that can activate the inhibitory activity of the human inhibitory CD200R.

To examine the extent of inhibition, for example, samples or assays comprising a given, e.g., protein, gene, cell, or organism, are treated with a potential activator or inhibitor and are compared to control samples without the inhibitor. Control samples, i.e., samples not treated with antagonist, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 25-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme, et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001)*Glia* 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least ten times the control.

"Ligand" refers, e.g., to a small molecule, peptide, polypeptide, and membrane associated or membrane-bound molecule, or complex thereof, that can act as an agonist or antagonist of a receptor. "Ligand" also encompasses an agent that is not an agonist or antagonist, but that can bind to the receptor. Moreover, "ligand" includes a membrane-bound ligand that has been changed, e.g., by chemical or recombinant methods, to a soluble version of the membrane-bound ligand. By convention, where a ligand is membrane-bound on a first cell, the receptor usually occurs on a second cell. The second cell may have the same or a different identity as the first cell. A ligand or receptor may be entirely intracellular, that is, it may reside in the cytosol, nucleus, or some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

"Small molecule" is defined as a molecule with a molecular weight that is less than 10 kDa, typically less than 2 kDa, preferably less than 1 kDa, and most preferably less than about 500 Da. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins, have been described (see, e.g., Casset, et al. (2003) *Biochem. Biophys. Res. Commun.* 307:198-205; Muyldermans (2001) *J. Biotechnol.* 74:277-302; Li (2000) *Nat. Biotechnol.* 18:1251-1256; Apostolopoulos, et al. (2002) *Curr. Med. Chem.* 9:411-420; Monfardini, et al. (2002) *Curr. Pharm. Des.* 8:2185-2199; Domingues, et al. (1999) *Nat. Struct. Biol.* 6:652-656; Sato and Sone (2003) *Biochem. J.* 371:603-608; U.S. Pat. No. 6,326,482 issued to Stewart, et al).

"Specifically" or "selectively" binds, when referring to a ligand/receptor, antibody/antigen, or other binding pair, indicates a binding reaction that is determinative of the presence of the protein in a heterogeneous population of proteins and other biologics. Thus, under designated conditions, a specified ligand binds to a particular receptor and does not bind in a significant amount to other proteins present in the sample. By way of example, the antibody, or binding compound derived from the antigen-binding site of an antibody, of the contemplated method binds to its antigen, or a variant or mutein thereof, with an affinity that is at least two fold greater, preferably at least ten times greater, more preferably at least 20-times greater, and most preferably at least 100-times greater than the affinity with any other antigen. In a preferred embodiment the antibody will have an affinity that is greater than about $10^9$ $M^{-1}$, as determined, e.g., by Scatchard analysis (Munsen et al. (1980) *Analyt. Biochem.* 107:220-239). By way of example, and not limitation, designated conditions can encompass an assay in which the heterogenous population of proteins and other biologics are all derived from the same species. Also by way of example, and not limitation, the antibody or binding compound derived from the antigen-binding site of an antibody specifically or selectively binds the anti human inhibitory CD200R but does not specifically or selectively binds the CYS mutated human CD200RLa (see, e.g., FIG. 9 and Example 13) or a human CD200RLa fusion protein (extracellular domain of human CD200RLa fused to the Fc portion of human IgG1, see, e.g. Example 13).

As used herein, the term "immunomodulatory agent" refers to natural or synthetic agents that suppress or modulate an immune response. The immune response can be a humoral or cellular response. Immunomodulatory agents encompass immunosuppressive or anti-inflammatory agents.

"Immunosuppressive agents", "immunosuppressive drugs", or "immunosuppressants" as used herein are therapeutics that are used in immunosuppressive therapy to inhibit or prevent activity of the immune system. Clinically they are used to prevent the rejection of transplanted organs and tissues (e.g. bone marrow, heart, kidney, liver), and/or in the treatment of autoimmune diseases or diseases that are most likely of autoimmune origin (e.g. rheumatoid arthritis, myasthenia gravis, systemic lupus erythematosus, ulcerative colitis, multiple sclerosis). Immunosuppressive drugs can be classified as: glucocorticoids; cytostatics; antibodies (biological response modifiers); drugs acting on immunophilins; other drugs, including known chemotherpeutic agents used in the treatment of proliferative disorders. For multiple sclerosis, in particular, the antibodies of the present invention can be administered in conjunction with a new class of myelin binding protein-like therapeutics, known as copaxones.

"Anti-inflammatory agents" or "anti-inflammatory drugs" refer to both steroidal and non-steroidal therapeutics. Steroids, also known as corticosteroids, are drugs that closely resemble cortisol, a hormone produced naturally by adrenal glands. Steroids are used as the main treatment for certain inflammatory conditions, such as: systemic vasculitis (inflammation of blood vessels); and myositis (inflammation of muscle). Steroids might also be used selectively to treat inflammatory conditions such as: rheumatoid arthritis (chronic inflammatory arthritis occurring in joints on both sides of the body); systemic lupus erythematosus (a generalized disease caused by abnormal immune system function); Sjögren's syndrome (chronic disorder that causes dry eyes and a dry mouth).

Non-steroidal anti-inflammatory drugs, usually abbreviated to NSAIDs, are drugs with analgesic, antipyretic and anti-inflammatory effects—they reduce pain, fever and inflammation. The term "non-steroidal" is used to distinguish these drugs from steroids, which (amongst a broad range of other effects) have a similar eicosanoid-depressing, anti-inflammatory action. NSAIDs are generally indicated for the symptomatic relief of the following conditions: rheumatoid arthritis; osteoarthritis; inflammatory arthropathies (e.g. ankylosing spondylitis, psoriatic arthritis, Reiter's syndrome); acute gout; dysmenorrhoea; metastatic bone pain; headache and migraine; postoperative pain; mild-to-moderate pain due to inflammation and tissue injury; pyrexia; and renal colic. NSAIDs include salicylates, arlyalknoic acids, 2-arylpropionic acids (profens), N-arylanthranilic acids (fenamic acids), oxicams, coxibs, and sulphonanilides.

Disease-modifying anti-rheumatic drugs (DMARDs) may be administered, often in combination with NSAIDs. Commonly prescribed DMARDs include hydroxychloroquine/chloroquine, methotrexate, gold therapy, sulfasalazine, and azathioprine.

II. Antibodies Specific for Human Inhibitory CD200R

The present invention provides anti-human inhibitory CD200Rr antibodies and uses thereof to treat various inflammatory, immune and proliferative disorders, including rheumatoid arthritis (RA), osteoarthritis, rheumatoid arthritis osteoporosis, inflammatory fibrosis (e.g., scleroderma, lung fibrosis, and cirrhosis), inflammatory bowel disorders (e.g., Crohn's disease, ulcerative colitis and inflammatory bowel disease), asthma (including allergic asthma), allergies, COPD, multiple sclerosis, psoriasis, uveitis and cancer.

Any suitable method for generating monoclonal antibodies may be used to generate the anti-human inhibitory CD200R antibodies of the present invention. For example, a recipient animal may be immunized with a linked or unlinked (e.g. naturally occurring) form of the human inhibitory CD200R, or a fragment thereof. Any suitable method of immunization can be used. Such methods can include adjuvants, other immunostimulants, repeated booster immunizations, and the use of one or more immunization routes.

Any suitable form of the human inhibitory CD200R can be used as the immunogen (antigen) for the generation of the non-human antibody specific for human inhibitory CD200R, which antibody can be screened for biological activity. The eliciting immunogen may be full-length human inhibitory CD200R or peptides thereof encompassing single epitopes or multiple epitopes. The immunogen may be used alone or in combination with one or more immunogenicity enhancing agents known in the art. The immunogen may be purified from a natural source or produced in a genetically modified cell. DNA encoding the immunogen may be genomic or non-genomic (e.g., cDNA) in origin. Immunogen-encoding DNA may be expressed using suitable genetic vectors, including but not limited to adenoviral vectors, adenoassociated viral vectors, baculoviral vectors, plasmids, and non-viral vectors, such as cationic lipids. Sequences for human CD200R can be found, for example, in US2006/0084121, Wright G J et al (2003) 171(6):3034-3046 (herein incorporated by reference in their entirety) and FIG. 13. By way of example and not limitation, either the long or short form of the human inhibitory receptor can be used as the immunogen (antigen) Genbank Accession Numbers for the short form of the human inhibitory receptor and the long form of the human inhibitory receptor are AF283760 and AF283760 respectively. The short form of the human inhibitory CD200R is also provided in FIG. 13.

In an alternative embodiment, a non-human primate inhibitory CD200R, such as the cyno-inhibitory CD200R (see FIG. 13), can be used as an immunogen (antigen) for the generation of the non-human antibody specific for human inhibitory CD200R, which antibody can be screened for biological activity. The eliciting immunogen may be full-length cyno-inhibitory CD200R or peptides thereof encompassing single epitopes or multiple epitopes. The immunogen may be used alone or in combination with one or more immunogenicity enhancing agents known in the art. The immunogen may be purified from a natural source or produced in a genetically modified cell. DNA encoding the immunogen may be genomic or non-genomic (e.g., cDNA) in origin. Immunogen-encoding DNA may be expressed using suitable genetic vectors, including but not limited to adenoviral vectors, adenoassociated viral vectors, baculoviral vectors, plasmids, and non-viral vectors, such as cationic lipids.

Any suitable method can be used to elicit an antibody response with the desired biologic properties, e.g. to activate the inhibitory activity of the human inhibitory CD200R. In some embodiments, antibodies are raised in mammalian hosts such as mice, rodents, primates, humans, etc. Techniques for preparing monoclonal antibodies may be found in, e.g., Stites et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Thus, monoclonal antibodies may be obtained by a variety of techniques familiar to researchers skilled in the art. Typically, spleen cells from an animal immunized with a desired antigen are immortalized, commonly by fusion with a myeloma cell. See Kohler and Milstein (1976) Eur. J. Immunol. 6:511-519. Alternative methods of immortalization include transformation with Epstein Barr Virus, oncogenes, or retroviruses, or other methods known in the art. See, e.g., Doyle et al. (eds.) (1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen. The yield of monoclonal antibodies produced by such cells may be enhanced by various techniques, including injection into the peritoneal cavity of a vertebrate host.

Other suitable techniques involve selection of libraries of antibodies in phage or similar vectors. See, e.g., Huse et al., Science 246:1275-1281 (1989); and Ward et al., Nature 341: 544-546 (1989). The antibodies of the present invention may be used without modification, e.g. as the parental rodent antibody, or with modifications to facilitate their use as therapeutic agents in human subjects, such as chimeric or humanized antibodies. In some embodiments, the antibodies will be labeled, covalently or non-covalently, with a substance that provides a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly U.S. Pat. No. 4,816,567; and Queen et al. (1989) Proc. Nat'l Acad. Sci. USA 86:10029-10033; or made in transgenic mice, see Mendez et al. (1997) Nature Genetics 15:146-156; also see Abgenix and Medarex technologies.

Antibodies against predetermined fragments of human inhibitory CD200R can be raised by immunization of animals with conjugates of the predetermined fragment of human inhibitory CD200R with carrier proteins. Monoclonal antibodies are prepared from cells secreting the desired antibody. These antibodies can be screened for binding to normal or defective human inhibitory CD200R These monoclonal antibodies will usually bind with at least a $K_d$ of about 1 µM, more usually at least about 300, 30, 10, or 3 nM, preferably at least about 300, 100, 30, 10, 3, or 1 µM. Because of the inverse relationship of $K_a$ values and affinity, references to binding with a given $K_d$ "or less" refers to binding with an affinity that is at least as high as the recited numerical value, i.e. with a $K_d$ that is at least as low as the cited value. Binding affinities may be determined by ELISA, or by Biacore® surface plasmon resonance spectroscopy (see Example 4), KinExA (see Example 3), ECL methods. Suitable non-human antibodies may also be identified using the biological assays described in Example 5, infra.

An exemplary method of producing anti-human inhibitory CD200R antibodies of the present invention is described at Example 2.

III. Humanization of Human Inhibitory CD200R Specific Antibodies

Any suitable non-human antibody can be used as a source for the hypervariable region of an anti-human inhibitory CD200R antibody of the present invention. Sources for non-human antibodies include, but are not limited to, rodents (e.g. mouse, rat), Lagomorphs (including rabbits), cows, and non-human primates. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity and affinity. Furthermore, humanized antibodies may comprise residues that are not found in the recipient antibody or in the donor antibody, such as modifications made to further refine antibody performance of the desired biological activity. For further details, see Jones et al. (1986) Nature 321: 522-525; Reichmann et al. (1988) Nature 332: 323-329; and Presta (1992) Curr. Op. Struct. Biol. 2: 593-596.

Methods for recombinantly engineering and producing antibodies have been described, e.g., by Boss et al. (U.S. Pat. No. 4,816,397), Cabilly et al. (U.S. Pat. No. 4,816,567), Law et al. (European Patent Application Publication No. 438 310) and Winter (European Patent Application Publication No. 239 400).

Amino acid sequence variants of humanized anti-human inhibitory CD200R antibodies of the present invention may be prepared by introducing appropriate nucleotide changes into the humanized anti-human inhibitory CD200R DNA, or by peptide synthesis. Any combination of deletion, insertion, and substitution may be made to arrive at the final construct, provided that the final construct possesses the desired characteristics. The amino acid changes also may alter post-translational processing of the humanized anti-human inhibitory CD200R antibody, such as changing the number or position of glycosylation sites.

One useful method for identifying residues or regions of a humanized anti-human inhibitory CD200R antibody that are preferred locations for mutagenesis is called "alanine scanning mutagenesis." Cunningham and Wells (1989) *Science* 244: 1081-1085. A group of target residues is identified (e.g., charged residues such as Arg, Asp, H is, Lys, and Glu) and replaced by a neutral or negatively charged amino acid (most preferably alanine or polyalanine) to alter the interaction of the amino acids with human inhibitory CD200R. The residues showing functional sensitivity to alanine substitutions are then refined by introducing further amino acid substitutions. In one embodiment, the effect of mutations at a given target codon is determined by alanine scanning or random mutagenesis followed by activity and binding analysis of the resulting humanized anti-human inhibitory CD200R antibody variants.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include humanized anti-human inhibitory CD200R antibody with an N-terminal methionyl residue or the antibody fused to an epitope tag. Other variants include the fusion of an enzyme or a polypeptide that increases the serum half-life of an antibody to the N- or C-terminus.

Another type of variant is an amino acid substitution variant. These variants have at least one amino acid residue in the humanized anti-human inhibitory CD200R antibody molecule removed and a different residue inserted in its place. The sites of greatest interest for substitutional mutagenesis include the hypervariable loops, but FR alterations are also contemplated. Hypervariable region residues or FR residues involved in antigen binding are generally substituted in a relatively conservative manner.

Other amino acid variants of the antibody alter the original glycosylation pattern of the antibody, e.g. by eliminating one or more carbohydrate moieties and/or adding one or more glycosylation sites. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. O-linked glycosylation involves attachment of N-acetylgalactosamine, galactose, or xylose to a hydroxyamino acid, most commonly serine or threonine, although 5-hydroxyproline or 5-hydroxylysine may also be used.

Glycosylation sites can be added to the antibodies of the present invention by inserting one or more of the above-described tripeptide sequences (for N-linked glycosylation sites), or addition of one or more serine or threonine residues (for O-linked glycosylation sites).

Nucleic acid molecules encoding amino acid sequence variants of humanized human inhibitory CD200R specific antibody are prepared by a variety of methods known in the art. These methods include, but are not limited to, isolation from a natural source (in the case of naturally occurring amino acid sequence variants), or by oligonucleotide-mediated (or site-directed) mutagenesis, PCR mutagenesis, or cassette mutagenesis.

Ordinarily, amino acid sequence variants of the humanized anti-human inhibitory CD200R antibody will have an amino acid sequence having at least 50% amino acid sequence identity with the original humanized antibody amino acid sequences of either the heavy or the light chain, preferably at least 70%, 80%, 85%, 90%, and most preferably at least 95%. Identity or homology with respect to this sequence is defined herein as the percentage of amino acid residues in the candidate sequence that are identical with the humanized anti-human inhibitory CD200R residues when the sequences are optimally aligned (i.e. after aligning the sequences and introducing gaps, if necessary, to achieve the maximum percent sequence identity), and not considering any conservative substitutions as part of the sequence identity. None of N-terminal, C-terminal, or internal extensions, deletions, or insertions into the antibody sequence is considered to affect sequence identity or homology.

The humanized antibody can be selected from any class of immunoglobulins, including IgM, IgG, IgD, IgA, and IgE. In one embodiment, the antibody is an IgG antibody. Any isotype of IgG can be used, including $IgG_1$, $IgG_2$, $IgG_3$, and $IgG_4$. Variants of the IgG isotypes are also contemplated. The humanized antibody may comprise sequences from more than one class or isotype. Optimization of the necessary constant domain sequences to generate the desired biologic activity is readily achieved by screening the antibodies in the biological assays described below in the Examples.

Likewise, either class of light chain can be used in the compounds and methods herein. Specifically, kappa, lambda, or variants thereof are useful in the present compounds and methods.

Any suitable portion of the CDR sequences from the non-human antibody can be used to create the humanized antibodies of the present invention. The CDR sequences may be mutagenized by substitution, insertion or deletion, although such mutations would be minimal because of the need to maintain human inhibitory CD200R binding affinity and specificity. Typically, at least 75% of the humanized antibody CDR residues will correspond to those of the non-human CDR residues, more often 90%, and most preferably greater than 95%, and frequently 100%.

Any suitable portion of the FR sequences from the human antibody can be used. The FR sequences can be mutagenized by substitution, insertion or deletion of at least one residue such that the FR sequence is distinct from the human and non-human antibody sequence employed. It is contemplated that such mutations would be minimal. Typically, at least 75% of the humanized antibody residues will correspond to those of the human FR residues, more often 90%, and most preferably greater than 95%.

Also contemplated are chimeric antibodies or fragments thereof, so long as they exhibit the desired biological activity (U.S. Pat. No. 4,816,567; and Morrison et al. (1984) *Proc. Natl. Acad. Sci. USA* 81: 6851-6855). As noted above, typical chimeric antibodies comprise constant domain sequences from antibodies from one species linked to the variable domain of an antigen-specific antibody obtained from a different species.

The binding compounds of the invention may comprise bispecific antibodies. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art: For example, bispecific antibodies can be produced recombinantly using the co-expression of two immunoglobulin heavy chain/light chain pairs. See, e.g., Milstein et al. (1983) *Nature* 305: 537-39. Alternatively, bispecific antibodies can be prepared using chemical linkage. See, e.g., Brennan, et al. (1985) *Science* 229: 81. Bispecific antibodies include bispecific antibody fragments. See, e.g., Hollinger, et al. (1993) *Proc. Natl. Acad. Sci. U.S.A.* 90: 6444-48, Gruber, et al., *J. Immunol.* 152: 5368 (1994).

An exemplary method of humanizing anti-human human inhibitory CD200R antibodies of the present invention is described at Example 2.

IV. Characterization of Human Inhibitory CD200R Specific Antibodies

The methods described herein were used to generate monoclonal antibodies immunoreactive with human inhibitory CD200R, as described in greater detail in Example 1 and 2. FIGS. 1 and 2 show sequence alignments of the variable regions of the light and heavy chains, respectively, of various anti-human inhibitory CD200R antibodies of the present invention. CDR regions are indicated, and numbering is according to Kabat et al. (1991).

A plasmid containing the nucleic acid sequences encoding the humanized anti human inhibitory CD200R light and heavy chains was deposited pursuant to the Budapest Treaty on Dec. 6, 2006, with the ATCC (Manassas, Va., USA) under Accession Number PTA-8067. The nucleic acid sequences encoding the light and heavy chains and also encoding signal peptides are in a single plasmid operably linked to cytomegalovirus (CMV) promoter. The plasmids also contains a DHFR cDNA operably linked to a mouse mammary tumor virus long terminal repeat (MMTV-LTR) for plasmid amplification and a hygromycin B gene operably linked to the TK promoter for selection in mammalian cells. By way of example, the plasmid can be used to transfect a dhfr⁻ mammalian cell line for expression of a recombinant protein. Examples of dhfr⁻ mammalian cell lines, include, but are not limited to, CHO-DXB11 and DG44.). In one embodiment, the binding compound is the mature antibody produced from the expression vector having ATCC Accession No. PTA-8067 (huDX182 with signal sequence in pACD200RV1 plasmid) deposited Dec. 6, 2006 with the ATCC (Manassas, Va. USA).

In another embodiment, the binding compound has the same CDRs as the antibody produced from the hybridoma having ATCC Accession No. PTA-8838, deposited as strain HC809.14F12.6.DX248.3 on Dec. 13, 2007.

The light and heavy chain CDRs of the antibodies of the present invention are provided at Tables 2 and 3, respectively. By way of example and not limitation, the $V_L$ domain CDRs are selected from SEQ ID NOs: 1, 2 and 3 and the $V_H$ domain CDRs are selected from SEQ ID NOs: 19, 20 and 21. Also by way of example, and not limitation, the $V_L$ domain CDRs are selected from RASKNIRSYLA (SEQ ID No.: 55), SEQ ID NO: 2 and SEQ ID NO: 3 and the $V_H$ domain CDRs are selected from SEQ ID NOs: 19, 20 and 21. By way of example and not limitation, the $V_L$ domain CDRs are selected from SEQ ID NOs: 16, 17 and 18 and the $V_H$ domain CDRs are selected from SEQ ID NOs: 34, 35 and 35.

TABLE 2

Light Chain CDRs

| Antibody | CDRL1 | CDRL2 | CDRL3 |
|---|---|---|---|
| huDX182 | KASKNIRSYLA (SEQ ID No.: 1) | SGSTLHS (SEQ ID No.: 2) | QQHHEYPLT (SEQ ID No.: 3) |
| DX182 | KASKNIRSYLA (SEQ ID No.: 4) | SGSTLHS (SEQ ID No.: 5) | QQHHEYPLT (SEQ ID No.: 6) |
| DX185 | KAGKNINTNLA (SEQ ID No.: 7) | SGSTLQS (SEQ ID No.: 8) | QQHNEFPLT (SEQ ID No.: 9) |
| DX178 | KASKNISKYLA (SEQ ID No.: 10) | SGSTLQS (SEQ ID No.: 11) | QQHNEFPLT (SEQ ID No.: 12) |
| DX184 | KASQNVGSNVD (SEQ ID No.: 13) | KASNRYT (SEQ ID No.: 14) | MQSLSFPYT (SEQ ID No.: 15) |
| DX248 | QASQGTSINLN (SEQ ID No.: 16) | SANNLED (SEQ ID No.: 17) | LQITYLPWT (SEQ ID No.: 18) |

TABLE 3

Heavy Chain CDRs

| Antibody | CDRH1 | CDRH2 | CDRH3 |
|---|---|---|---|
| huDX182 | GYTITSGYDWS (SEQ ID No.: 19) | YINYGGSTNYKPSLGS (SEQ ID No.: 20) | YNEYKSYIYDWYFDF (SEQ ID No.: 21) |
| DX182 | GYTITSGYDWS (SEQ ID No.: 22) | YINYGGSTNYKPSLGS (SEQ ID No.: 23) | YNEYKSYIYDWYFDF (SEQ ID No.: 24) |
| DX185 | GYTITSGYDWS (SEQ ID No.: 25) | YINYSGSTVYNPSLRS (SEQ ID No. 26) | FEASNTYLYDWYFDF (SEQ ID No.: 27) |
| DX178 | GFTITSGYDWS (SEQ ID No.: 28) | YIGFSGSTVYNPSLNS (SEQ ID No.: 29) | SFVQNTFIYDWFFDF (SEQ ID No.: 30) |
| DX184 | GFSLTN-NGVS (SEQ ID No.: 31) | AISSGGGTFYNSALKS (SEQ ID No.: 32) | DGD-----WDWYFDF (SEQ ID No.: 33) |

TABLE 3-continued

Heavy Chain CDRs

| Antibody | CDRH1 | CDRH2 | CDRH3 |
|---|---|---|---|
| DX248 | GYTFTS-YWMH (SEQ ID No.: 34) | NIYPGSGSTNYDEKFKS (SEQ ID No.: 35) | GTG----------AY (SEQ ID No.: 36) |

Sequences are provided for humanized $V_L$ and $V_H$ regions and the humanized antibody, huDX182 (SEQ ID NOS: 42 and 48 respectively). These humanized variable domains may be used to create full-length chimeric or humanized antibodies by adding the appropriate constant domain sequences.

In one embodiment of the present invention, light and heavy chains of antibody huDX182 are created by appending human constant domains (human kappa light chain and human IgG1 constant domain, respectively) to the C-terminus of the humanized $V_L$ (SEQ ID NO: 42) and $V_H$ regions (SEQ ID NO: 48). Sequences of huDX182 light and heavy chains are provided at SEQ ID NOs: 49 and 50.

In another embodiment, full length humanized antibodies are created by substituting framework residues (i.e. those amino acid residues in the variable domain that are not part of a CDR) of the chimeric forms antibodies with human germline framework sequences, as described in more detail in Example 2. The resulting antibodies retain only the CDR sequences from the rat antibodies, with the constant domains and framework sequences replaced by human-derived sequences. Full-length mature light and heavy chains for humanized antibody huDX182, excluding signal sequences, are provided at SEQ ID NOs: 49 and 50 (FIGS. 3 and 4), respectively.

In a further embodiment, the full-length light and heavy chains of the humanized antibodies of the present invention are cloned to have a signal peptide at their N-terminus to facilitate secretion from cells when the antibody is produced. In one embodiment, a 19 amino acid signal sequence is added to both the light and heavy chains of the humanized DX182 antibody. DNA sequences of the full length light and heavy chains of humanized DX182, with signal sequence added, are provided at SEQ ID NOs: 52 and 54 (FIGS. 5A and 5B, FIGS. 6A, 6B and 6C). Such DNA sequences can be cloned and expressed in any suitable expression vector for production of the humanized antibodies of the present invention. In other embodiments, signal sequences are added that are different than the specific signal sequence provided, depending on the intended method of production of the antibodies. Such signal sequences may be obtained from the scientific literature, for example Choo et al.(2005) "SPdb—a signal peptide database," *BMC Bioinformatics* 6:249. Amino acid sequences of the full length light and heavy chains of humanized DX182, with signal sequence added, are provided at SEQ ID NOs: 51 and 53 (FIGS. 5A and 5B, FIGS. 6A, 6B and 6C).

In yet other embodiments, different constant domains may be appended to the humanized $V_L$ and $V_H$ regions provided herein. For example, if a particular intended use of an antibody (or fragment) of the present invention were to call for altered effector functions, a heavy chain constant domain other than IgG1 may be used. Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used.

V. Affinity and Biological Activity of Humanized Anti-CD200R

Antibodies having the characteristics identified herein as being desirable in a humanized anti-human inhibitory CD200R antibody can be screened for inhibitory biologic activity in vitro, in vivo, or by measuring binding affinity. To screen for antibodies that bind to the same epitope on human inhibitory CD200R bound by an antibody of interest (e.g., those which activate the inhibitory function of the inhibitory receptor), a routine cross-blocking assay can be performed such as that described in ANTIBODIES, A LABORATORY MANUAL, Cold Spring Harbor Laboratory, Ed Harlow and David Lane (1988). Alternatively, epitope mapping can be performed to determine whether the antibody binds an epitope of interest, e.g., as described in Champe et al. (1995) *J. Biol. Chem.* 270:1388-1394. Antibody affinities (e.g. for human CD200R) may be determined using standard methods, including, those described in Examples 3 and 4. Preferred humanized antibodies are those which bind human inhibitory CD200R with a $K_d$ value of no more than about 100 nM ($1 \times 10^{-7}$ M); preferably no more than about 10 nM; more preferably no more than about 1 nM. Even more preferred are embodiments in which the antibodies have $K_d$ values of no more than about 200 pM ($2 \times 10^{-10}$ M), 100 pM, 50 pM, 20 pM, 10 pM, 5 pM or even 2 pM.

The antibodies, and fragments thereof, useful in the present compounds and methods include, but are not limited to, biologically active antibodies and fragments. As used herein, the term "biologically active" refers to an antibody or antibody fragment that is capable of binding the desired antigenic epitope and directly or indirectly exerting a biologic effect (e.g., activating the inhibitory activity of the human inhibitory CD200R receptor). As used herein, the term "specific" refers to the selective binding of the antibody to the target antigen epitope. Antibodies can be tested for specificity of binding by comparing binding to human inhibitory CD200R to binding to irrelevant antigen or antigen mixture under a given set of conditions. As an example, an antibody is considered to be specific if it binds to a human inhibitory CD200R with an affinity at least 10-fold, and preferably 50-fold higher than its affinity for an irrelevant antigen or antigen mixture. For example, as used herein, an antibody that "specifically binds" to a fusion protein comprising the extracellular domain of the human inhibitory CD200R and the Fc portion of human IgG1, does not bind the Fc portion of the IgG1 alone or when it is fused to a protein other than human inhibitory CD200R. Also by way of example, and not limitation, the antibody or binding compound derived from the antigen-binding site of an antibody useful in the methods of the invention specifically or selectively binds the human inhibitory CD200R but does not specifically or selectively bind the CYS mutated human CD200RLa (see, e.g., FIG. 9 and Example 13) or a human CD200RLa fusion protein (extracellular domain of human CD200RLa fused to the Fc portion of human IgG1, see, e.g. Example 13).

V. Antibody Production

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence. In one embodiment, both the light and heavy chains of the humanized anti-human inhibitory antibody of the present invention are expressed from the same vector, e.g. a plasmid or an adenoviral vector.

Antibodies of the present invention may be produced by any method known in the art. In one embodiment, antibodies are expressed in mammalian or insect cells in culture, such as chinese hamster ovary (CHO) cells, human embryonic kidney (HEK) 293 cells, mouse myeloma NSO cells, baby hamster kidney (BHK) cells, Spodoptera frugiperda ovarian (Sf9) cells. In one embodiment, antibodies secreted from CHO cells are recovered and purified by standard chromatographic methods, such as protein A, cation exchange, anion exchange, hydrophobic interaction, and hydroxyapatite chromatography. Resulting antibodies are concentrated and stored in 20 mM sodium acetate, pH 5.5.

In another embodiment, the antibodies of the present invention are produced in yeast according to the methods described in WO2005/040395. Briefly, vectors encoding the individual light or heavy chains of an antibody of interest are introduced into different yeast haploid cells, e.g. different mating types of the yeast *Pichia pastoris*, which yeast haploid cells are optionally complementary auxotrophs. The transformed haploid yeast cells can then be mated or fused to give a diploid yeast cell capable of producing both the heavy and the light chains. The diploid strain is then able to secret the fully assembled and biologically active antibody. The relative expression levels of the two chains can be optimized, for example, by using vectors with different copy number, using transcriptional promoters of different strengths, or inducing expression from inducible promoters driving transcription of the genes encoding one or both chains.

In one embodiment, the respective heavy and light chains of a plurality of different anti-human inhibitory CD200R antibodies (the "original" antibodies) are introduced into yeast haploid cells to create a library of haploid yeast strains of one mating type expressing a plurality of light chains, and a library of haploid yeast strains of a different mating type expressing a plurality of heavy chains. These libraries of haploid strains can be mated (or fused as spheroplasts) to produce a series of diploid yeast cells expressing a combinatorial library of antibodies comprised of the various possible permutations of light and heavy chains. The combinatorial library of antibodies can then be screened to determine whether any of the antibodies has properties that are superior (e.g. higher affinity for anti human inhibitory CD200R) to those of the original antibodies. See. e.g., WO2005/040395.

In another embodiment, antibodies of the present invention are human domain antibodies in which portions of an antibody variable domain are linked in a polypeptide of molecular weight approximately 13 kDa. See, e.g., U.S. Pat. Publication No. 2004/0110941. Such single domain, low molecular weight agents provide numerous advantages in terms of ease of synthesis, stability, and route of administration.

VI. Pharmaceutical Compositions and Administration

To prepare pharmaceutical or sterile compositions of the anti-huCD200R antibodies of the present invention, the antibody is admixed with a pharmaceutically acceptable carrier or excipient. See, e.g., *Remington's Pharmaceutical Sciences and U.S. Pharmacopeia: National Formulary*, Mack Publishing Company, Easton, Pa. (1984).

Formulations of therapeutic and diagnostic agents may be prepared by mixing with physiologically acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.). In one embodiment, anti-human inhibitory CD200R antibodies of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). Antibodies exhibiting high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

The mode of administration is not particularly important. Suitable routes of administration include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration can be carried out in a variety of conventional ways, such as oral ingestion, inhalation, insufflation, topical application or cutaneous, transdermal, subcutaneous, intraperitoneal, parenteral, intra-arterial or intravenous injection. Intravenous administration to the patient is preferred.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing an inflammatory, autoimmune, or proliferative response to the reagent. In the case of human subjects, for example, chimeric, humanized and fully human antibodies are preferred.

Antibodies, antibody fragments, and cytokines can be provided by continuous infusion, or by doses administered, e.g., daily, 1-7 times per week, weekly, bi-weekly, monthly, bimonthly etc. Doses may be provided intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). Doses may also be provided to achieve a pre-determined target concentration of anti-human inhibitory CD200R antibody in the subject's serum, such as 0.1, 0.3, 1, 3, 10, 30, 100, 300 µg/ml or more. In other embodiments, a humanized anti-human inhibitory CD200R antibody of the present invention is administered subcutaneously or intravenously, on a weekly, biweekly or "every 4 weeks" basis at 10, 20, 50, 80, 100, 200, 500, 1000 or 2500 mg/subject.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of an human inhibitory CD200R binding compound of the invention that, when administered alone or in combination with an additional therapeutic agent to a cell, tissue, or subject, is effective to prevent or ameliorate one or more symptoms of a disease or condition or the progression of such disease or condition. A therapeutically effective dose further refers to that amount of the binding compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%.

Methods for co-administration with a second therapeutic agent, e.g., cytokine, another therapeutic antibody, steroid, chemotherapeutic agent, or antibiotic are well known in the art, see, e.g., Hardman, et al. (eds.) (2001) *Goodman and Gilman's The Pharmacological Basis of Therapeutics*, $10^{th}$ ed., McGraw-Hill, New York, N.Y.; Poole and Peterson (eds.) (2001) *Pharmacotherapeutics for Advanced Practice: A Practical Approach*, Lippincott, Williams & Wilkins, Phila., PA; Chabner and Longo (eds.) (2001) *Cancer Chemotherapy and Biotherapy*, Lippincott, Williams & Wilkins, Phila., PA. The pharmaceutical composition of the invention may also contain immunosuppressive or immunomodulating agents. Any suitable immunosuppressive agent can be employed, including but not limited to anti-inflammatory agents, corticosteroids, cyclosporine, tacrolimus (i.e., FK-506), sirolimus, interferons, soluble cytokine receptors (e.g., sTNRF and sIL-1R), agents that neutralize cytokine activity (e.g., inflixmab, etanercept), mycophenolate mofetil, 15-deoxyspergualin, thalidomide, glatiramer, azathioprine, leflunomide, cyclophosphamide, methotrexate, and the like. The pharmaceutical composition can also be employed with other therapeutic modalities such as phototherapy and radiation.

The human inhibitory CD200R binding compounds of the present invention can also be used in combination with one or more other therapeutic agents. By way of example and not limitation, the binding compounds of the present invention may be administered concurrently with cytokines or chemokines, as well as before or after antagonists (of other cytokines (e.g. antibodies), including but not limited to, IL-10, IL-23, M-1β, IL-6 and TGF-β. See, e.g., Veldhoen (2006) *Immunity* 24:179-189; Dong (2006) *Nat. Rev. Immunol.* 6(4):329-333

VII. Uses

The present invention provides methods for using engineered anti-human inhibitory CD200R antibodies for the treatment and diagnosis of inflammatory disorders and conditions, as well as autoimmune and proliferative disorders, including rheumatoid arthritis (RA), osteoarthritis, rheumatoid arthritis osteoporosis, inflammatory fibrosis (e.g., scleroderma, lung fibrosis, and cirrhosis), inflammatory bowel disorders (e.g., Crohn's disease, ulcerative colitis and inflammatory bowel disease), asthma (including allergic asthma), allergies, COPD, multiple sclerosis, psoriasis, uveitis and cancer.

Many modifications and variations of this invention can be made without departing from its spirit and scope, as will be apparent to those skilled in the art. The invention is defined by the terms of the appended claims, along with the full scope of equivalents to which such claims are entitled. The specific embodiments described herein, including the following examples, are offered by way of example only, and do not by their details limit the scope of the invention.

EXAMPLE 1

General Methods

Standard methods in molecular biology are described (Maniatis, et al. (1982) *Molecular Cloning, A Laboratory Manual*, Cold Spring Harbor Laboratory Press, Cold Spring Harbor, N.Y.; Sambrook and Russell (2001) *Molecular Cloning, 3rd* ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protcols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protcols in Immunology*, Vol. 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) *J. Biol. Chem.* 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17:397-399).

Single chain antibodies and diabodies are described (see, e.g., Malecki et al. (2002) *Proc. Natl. Acad. Sci. USA* 99:213-218; Conrath et al. (2001) *J. Biol. Chem.* 276:7346-7350; Desmyter et al. (2001) *J. Biol. Chem.* 276:26285-26290; Hudson and Kortt (1999) *J. Immunol. Methods* 231:177-189; and U.S. Pat. No. 4,946,778). Bifunctional antibodies are provided (see, e.g., Mack, et al. (1995) *Proc. Natl. Acad. Sci. USA* 92:7021-7025; Carter (2001) *J. Immunol. Methods* 248: 7-15; Volkel, et al. (2001) *Protein Engineering* 14:815-823; Segal, et al. (2001) *J. Immunol. Methods* 248:1-6; Brennan, et al. (1985) *Science* 229:81-83; Raso, et al. (1997)*J. Biol. Chem.* 272:27623; Morrison (1985) *Science* 229:1202-1207; Traunecker, et al. (1991) *EMBO* 1 10:3655-3659; and U.S. Pat. Nos. 5,932,448, 5,532,210, and 6,129,914).

Bispecific antibodies are also provided (see, e.g., Azzoni et al. (1998) *J. Immunol.* 161:3493; Kita et al. (1999) *J. Immunol.* 162:6901; Merchant et al. (2000) *J. Biol. Chem.* 74:9115; Pandey et al. (2000) *J. Biol. Chem.* 275:38633; Zheng et al. (2001) *J. Biol Chem.* 276:12999; Propst et al. (2000) *J. Immunol.* 165:2214; Long (1999) *Ann. Rev. Immunol.* 17:875).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies will usually bind with at least a $K_d$ of about $10^{-6}$ M, typically at least $10^{-7}$ M, more typically at least $10^{-8}$ M, preferably at least about $10^{-9}$ M, and more preferably at least $10^{-10}$ M, and most preferably at least $10^{-11}$ M (see, e.g., Presta et al. (2001) *Thromb. Haemost.* 85:379-389; Yang et al. (2001) *Crit. Rev. Oncol. Hematol.* 38:17-23; Carnahan et al. (2003) *Clin. Cancer Res.* (Suppl.) 9:3982s-3990s).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry, 2nd* ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

EXAMPLE 1

Rat Anti Human Inhibitory CD200R Monoclonal Antibodies

Monoclonal antibodies to human inhibitory CD200R were obtained as follows. Eight week old female Lewis rats (Harlan Sprague Dawley, Indianapolis, Ind., USA) were given a series of injections of an immunogenic fusion protein comprising the extracellular domain of the human inhibitory receptor CD200R fused to the Fc portion of human IgG1 (see, Wright et al (2003) *J. Immunol.* 171:3034-3046, herein incorporated by reference in its entirety). The extracellular residues were subcloned into the Xho 1 site of a modified pCDM8.1 g expression plasmid (E. E. Bates et al (1998) Mol. Immunol. 35:513). Protein was produced following transfection or infection of 293T or 293FT as described in Cherwinski et al (2005), J. Immunol. 174:1348). The injections were given at days 0, 14, 32, 46, and 83.

The day 0 injection was a subcutaneous (sc) injection of 50 µg CD200R-human IgG1 Fc fusion protein in Freund's Complete Adjuvant. On days 14, 32 and 46 rats were given ip injections of 25 µg CD200R human IgG1 Fc fusion protein in Freund's Incomplete Adjuvant. The day 83 injection was a combination of an ip injection of 20 µg CD200R-human IgG1 Fc fusion protein in Freund's Incomplete Adjuvant and an intravenous (iv) tail vein injection of CD200R-human IgG1 Fc fusion protein in saline.

A test bleed was performed at day 53. Fusion of rat splenocytes was performed on day 87, using $1.6 \times 10^8$ splenocytes and $1.8 \times 10^8$ myeloma cells divided into in thirty 96-well plates, giving a total of $1.13 \times 10^5$ total cells per well.

Primary screening of the resulting monoclonal antibodies (thousands) was performed by indirect ELISA on CD200R-human IgG1 Fc fusion protein.—Secondary screens on the resulting antibodies included specific staining of human CD200R expressing transfectants and human cultured human Mast cells. Subsequent experiments were performed to confirm that the candidate antibodies were able to bind to human CD200R expressing mast cells and that the antibodies were useful in various therapeutic, diagnostic and/or research purposes. Such screening may be done using binding assays (such as indirect ELISA or sandwich ELISA), by in vitro activity assay, or by in vivo activity assay, examples of which are provided herein.

DX176, DX177 and DX178 were generated in HC612 Dx182 and DX184 were generated in HC618.

An inhibitory cyno CD200R fusion protein (extracellular domain of the cyno inhibitory CD200R fused to the Fc portion of human IgG1) was used as the immunogen in female Balb/c mice to generate the mouse anti-cynoCD200R antibody DX248 utilizing the above method. Mouse anti-cyno CD200R (DX248) was generated in HC809. The hybridoma having ATCC Accession No. PTA-8838, deposited as strain HC809.14F12.6.DX248.3 on Dec. 13, 2007. the isotype of the antibody produced is mouse IgG1-Kappa.

EXAMPLE 2

Humanization of Rat Anti Human Inhibitory CD200R Antibodies

The humanization of rat anti human inhibitory CD200R monoclonal antibody huDX182 was performed essentially as described in WO 2005/047324 and WO 2005/047326, the disclosures of which are hereby incorporated by reference in their entireties. Briefly, human constant domains were used to replace the parental (rat) constant domains, and human germline sequences homologous to the rat variable domain sequences were selected and used to provide a human framework for the rat CDRs, as described in more detail below.

Procedure for Selection of Human Germline Framework Sequences

The following steps are used in selecting the appropriate germline framework sequences in humanizing the anti-human human inhibitory CD200R antibodies of the present invention.

1) Clone and sequence non-human $V_L$ and $V_H$ domains and determine amino acid sequence.

Heavy Chain

2) Compare the non-human $V_H$ sequence to a group of five human $V_H$ germline amino acid sequences; one representative from subgroups IGHV1 and IGHV4 and three representatives from subgroup IGHV3. The $V_H$ subgroups are listed in M. -P. Lefranc (2001) "Nomenclature of the Human Immunoglobulin Heavy (IGH) Genes", *Experimental and Clinical Immunogenetics*, 18:100-116. Comparison to the five germline sequences is performed as follows:

A) Assign the non-human $V_H$ sequence residue numbers according to Kabat et al. (1991).

B) Align the non-human $V_H$ sequence with each of the five human germline sequences. Since the V genes only comprise $V_H$ residues 1-94, only these residues are considered in the alignment.

C) Delineate the complementarity-determining (CDR) and framework (FR) regions in the sequence. CDR and FR are defined as a combination of the definitions provided in Kabat et al. (1991) (Id.) and Chothia and Lesk (1987) "Canonical Structures for the Hypervariable Regions of Immunoglobulins", *Journal of Molecular Biology*, 196: 901-917. The definition is thus: $V_H$ CDR1=26-35, CDR2=50-65, CDR3=95-102.

D) For each listed residue position below (Table 4), assign numerical score at each residue position for which the non-human and human sequences are IDENTICAL:

TABLE 4

| Residue # | Score | Reason |
|---|---|---|
| 2 | 4 | Affects CDR-H1, 3* |
| 4 | 3 | Affects CDR-H1, 3 |
| 24 | 3 | Affects CDR-H1 |
| 26 | 4 | Affects CDR-H1* |
| 27 | 4 | Affects CDR-H1, 3* |
| 29 | 4 | Affects CDR-H1* |
| 34 | 4 | Affects CDR-H1* |
| 35 | 2 | VH/VL interface |

TABLE 4-continued

| Residue # | Score | Reason |
|---|---|---|
| 37 | 2 | VH/VL interface |
| 39 | 2 | VH/VL interface |
| 44 | 2 | VH/VL interface |
| 45 | 2 | VH/VL interface |
| 47 | 4 | VH/VL interface, CDRL3 |
| 48 | 3 | Affects CDR-H2 |
| 49 | 3 | Affects CDR-H2 |
| 50 | 2 | VH/VL interface |
| 51 | 3 | Affects CDR-H2 |
| 58 | 2 | VH/VL interface |
| 59 | 3 | Affects CDR-H2 |
| 60 | 2 | VH/VL interface |
| 63 | 3 | Affects CDR-H2 |
| 67 | 3 | Affects CDR-H2 |
| 69 | 3 | Affects CDR-H2 |
| 71 | 4 | Affects CDR-H2* |
| 73 | 3 | Affects CDR-H1 |
| 76 | 3 | Affects CDR-H1 |
| 78 | 3 | Affects CDR-H1 |
| 91 | 2 | VH/VL interface |
| 93 | 3 | Affects CDR-H3 |
| 94 | 4 | Affects CDR-H3* |
|  | max 89 |  |

*Noted as affecting CDR conformation in C. Chothia et al. (1989) "Conformations of Immunoglobulin Hypervariable Regions", Nature 342: 877-883.

E) Add all residue position scores. Acceptor germline sequence is the one with the highest total score. In a case where two or more germline sequences have identical scores, then:
  1) Among the following residue positions add 1 to the total for each position where the non-human and human sequences are IDENTICAL: 1, 3, 5-23, 25, 36, 38, 40-43, 46, 66, 68, 70, 72, 74, 75, 77, 79-90, 92 (max 49).
  2) Acceptor germline sequence is the one with the highest total score. If two or more germline sequences still have identical scores, either one is acceptable as acceptor.

Light Chain

III) If the $V_L$ sequence is a member of the kappa subclass of $V_L$, compare non-human $V_L$ sequence to a group of four human $V_L$ kappa germline amino acid sequences. The group of four is comprised of one representative from each of four established human $V_L$ subgroups listed in Barbie and Lefranc (1998) "The Human Immunoglobulin Kappa Variable (IGKV) Genes and Joining (IGKJ) Segments", *Experimental and Clinical Immunogenetics*, 15:171-183, and M. -P. Lefranc (2001) "Nomenclature of the Human Immunoglobulin Kappa (IGK) Genes", *Experimental and Clinical Immunogenetics*, 18:161-174. The four subgroups also correspond to the four subgroups listed in Kabat et al. (1991) at pp. 103-130. Comparison to the four germline sequences is performed as follows:
  A) Assign the non-human $V_L$ sequence residue numbers according to Kabat et al. (1991).
  B) Align the non-human $V_L$ sequence with each of the four human germline sequences. Since the V genes only comprise $V_L$ residues 1-95, only these residues are considered in the alignment.
  C) Delineate the complementarity-determining (CDR) and framework (FR) regions in the sequence. CDR and FR are defined as a combination of the definitions provided in Kabat et al. (1991) and Chothia and Lesk (1987) "Canonical Structures for the Hypervariable Regions of Immunoglobulins", *Journal of Molecular Biology*, 196: 901-917. The definition is thus: $V_L$ CDR1=24-34, CDR2=50-56, CDR3=89-97.
  D) For each listed residue position below (Table 2), assign numerical score at each residue position for which the non-human and human sequences are IDENTICAL:

TABLE 5

| Residue # | Score | Reason |
|---|---|---|
| 2 | 4 | Affects CDR-L1, 3* |
| 4 | 3 | Affects CDR-L1, 3 |
| 25 | 4 | Affects CDR-L1* |
| 29 | 4 | Affects CDR-L1, 3* |
| 33 | 4 | Affects CDR-L1, 3* |
| 34 | 2 | VL/VH interface |
| 36 | 2 | VL/VH interface |
| 38 | 2 | VL/VH interface |
| 43 | 2 | VL/VH interface |
| 44 | 2 | VL/VH interface |
| 46 | 4 | VL/VH interface, CDR-H3 |
| 47 | 3 | Affects CDR-L2 |
| 48 | 4 | Affects CDR-L2* |
| 49 | 2 | VL/VH interface |
| 55 | 2 | VL/VH interface |
| 58 | 3 | Affects CDR-L2 |
| 62 | 3 | Affects CDR-L2 |
| 64 | 4 | Affects CDR-L2* |
| 71 | 4 | Affects CDR-L1* |
| 87 | 2 | VL/VH interface |
| 89 | 2 | VL/VH interface |
| 90 | 4 | Affects CDR-L3* |
| 91 | 2 | VL/VH interface |
| 94 | 2 | VL/VH interface |
| 95 | 4 | Affects CDR-L3* |

*Noted as affecting CDR conformation in C. Chothia et al. "Conformations of Immunoglobulin Hypervariable Regions", Nature 342: 877-883, 1989.

E) Add all residue position scores. Acceptor germline sequence is the one with the highest total score. In a case where two or more germline sequences have identical scores, then:
  1) Among the following residue positions add 1 to the total for each position where the non-human and human sequences are IDENTICAL: 1, 3, 5-23, 35, 37, 39-42, 57, 59-61, 63, 65-70, 72-86, 88.
  2) Acceptor germline sequence is the one with the highest total score. If two or more germline sequences still have identical scores, either one is acceptable as acceptor.

If the $V_L$ sequence is a member of the lambda subclass of $V_L$, an analogous procedure is performed using human $V_L$ lambda germline amino acid sequences from the literature sources cited above.

Humanization of Anti-human Inhibitory CD200R Antibodies

With regard to modification of the constant domains, the variable light and heavy domains of antibody huDX182 (rat anti-human inhibitory CD200R) were cloned and fused to a human kappa light chain (CL domain) and human IgG1 heavy chain (CH1-hinge-CH2-CH3), respectively. This combination of the rat variable domains and human constant domains comprises a chimeric version of antibody huDX182.

With regard to modification of the framework regions of the variable domains, the amino acid sequence of the $V_H$ domain of antibody DX182 was compared to a group of five human $V_H$ germline amino acid sequences; one representative from subgroups IGHV1 and IGHV4 and three representatives from subgroup IGHV3. The $V_H$ subgroups are listed in M. -P. Lefranc, "Nomenclature of the Human Immunoglobulin Heavy (IGH) Genes," *Experimental and Clinical Immunogenetics*, 18:100-116, 2001. Antibody 16C10 scored highest against human heavy chain germline DP-71 in subgroup IV.

The $V_L$ sequence of DX182 was of the kappa subclass. This sequence was compared to a group of four human $V_L$ kappa germline amino acid sequences. The group of four is comprised of one representative from each of four established human $V_L$ subgroups listed in V. Barbie & M. -P. Lefranc, "The Human Immunoglobulin Kappa Variable (IGKV) Genes and Joining (IGKJ) Segments", *Experimental and Clinical Immunogenetics*, 15:171-183, 1998 and M. -P. Lefranc, "Nomenclature of the Human Immunoglobulin Kappa (IGK) Genes", *Experimental and Clinical Immunogenetics*, 18:161-174, 2001. The four subgroups also correspond to the four subgroups listed in Kabat et al. (1991) at pp. 103-130. Antibody DX182 scored highest against human light chain germline Z-012 in subgroup II.

Once the desired germline framework sequences were determined, a plasmid encoding the full-length humanized variable heavy and light chains was generated. Substitution of human framework residues in place of the framework residues of the parental rat antibody DX182 can be viewed equivalently as the grafting of the rat DX182 CDRs onto the human framework sequences. The resulting antibody is referred to herein as "hu DX182 wt", with the "wt" designating the presence of the same CDRs as the parental rat DX182, as distinguished from the optimized CDRs Both the light and heavy chain variable domains were codon optimized, synthesized and inserted onto constant domains. to provide for potentially optimal expression. Codon optimization, which may improve expression of cloned antibodies, is purely optional.

The amino acid sequences of the light and heavy chains of humanized antibody DX182 are provided at FIGS. 3 and 4 respectively, and at SEQ ID NOs: 49 and 50. In the interest of clarity with regard to nomenclature, it is important to recognize that the Kabat numbering system includes non-numerical amino acid residue designations (e.g. $V_H$ residues 83a, 83b, 83c) to accommodate variations in the lengths of CDRs and framework regions among various antibodies. Although this numbering system is advantageous in allowing easy reference to corresponding amino acid residues among various antibodies with CDRs of different lengths, it can result in conflicting designations for specific amino acid residues when compared with strict sequential-numeric sequence numbering (e.g. sequence listings). Amino acid residue designations herein are made with reference to the relevant sequence listing unless otherwise noted, for example by reference to "Kabat numbering".

SEQ ID NOs: 50 and 49 do not include an N terminal signal peptide and represent the mature form of the protein. A mature form of the protein represents a protein without the signal sequence. SEQ ID NOs: 51 and 53 include an N terminal signal peptide.

FIG. 9 is an exemplary illustration of a humanized light and heavy domains for the DX248 antibody.

EXAMPLE 3

Determining the Equilibrium Dissociation Constant ($K_d$) for Rat Ant Human Inhibitory CD200R Antibodies using Kinexa Technology The equilibrium dissociation constants ($K_d$) for anti human inhibitory CD200R antibodies were determined using the KinExA 3000 instrument (Sapidyne Instruments Inc., Boise, Id., USA). KinExA uses the principle of the Kinetic Exclusion Assay method based on measuring the concentration of uncomplexed antibody in a mixture of antibody, antigen and antibody-antigen complex. See, e.g., Darling and Brault (2004) *Assay Drug Dev. Technol.* 2(6):647-57. The concentration of free antibody is measured by exposing the mixture to a solid-phase immobilized antigen for a very brief period of time. In practice, this is accomplished by flowing the solution phase antigen-antibody mixture past antigen-coated particles trapped in a flow cell. Data generated by the instrument are analyzed using custom software. Equilibrium constants are calculated using a mathematical theory based on the following assumptions:

1. The binding follows the reversible binding equation for equilibrium:

$$k_{on}[Ab][Ag] = k_{off}[AbAg], \text{ where } K_d = k_{off}/k_{on}$$

2. Antibody (Ab) and antigen (Ag) bind 1:1 and total antibody equals antigen-antibody complex (AbAg) plus free antibody.

3. Instrument signal is linearly related to free antibody concentration.

KinExA analysis was performed on several rat anti-human inhibitory CD200R antibodies., humanized variants thereof, and sequence variants of these humanized antibodies. A fusion protein consisting of the extracelleular domain of the human inhibitory receptor CD200R fused to the Fc portion of human IgG1 (see, Wright et al (2003) *J. Immunol.* 171:3034-3046, herein incorporated by reference in its entirety) was used in both the immobilized and solution phases for each KinExA determination. Poly(methyl-methacrylate) (PMMA) particles (98 micron) were coated with biotinylated human CD200R-Ig according to Sapidyne "Protocol for coating PMMA particles with biotinylated ligands having short or nonexistent linker arms." All experimental procedures were done according to the KinExA 3000 manual. All runs were done in duplicate.

The conditions for KinExA are provided at Table 6.

TABLE 6

| Kinexa Protocol | |
|---|---|
| Sample volume: | 2 ml |
| Sample flow rate: | 0.25 ml/min |
| Label volume: | 1 ml |
| Label flow rate: | 0.25 ml/min |
| Antibody conc.: | 0.05 nM |
| Highest antigen conc.: | 40 nM |
| Lowest antigen conc.: | 40 pM |

Two-fold serial dilutions of the antigen were prepared and mixed with the antibody at constant concentration. The mixture was incubated for 2 hours at 25° C. to equilibrate.

TABLE 7

| $K_d$ Values Determined by KinExA | |
|---|---|
| rat anti-human inhibitory CD200R mAb | Kd(pM) |
| DX182 | 56 |
| DX185 | 126 |
| DX178 | 628 |
| DX177 | 507 |
| DX184 | 26 |
| DX176 | 833.8 |

EXAMPLE 4

Determining the Equilibrium Dissociation Constant ($K_d$) for Rat Ant Human Inhibitory CD200R Antibodies using Biacore Technology The kinetic binding activities of anti human inhibitory CD200R antibodies against a fusion protein consisting of the extracellular domain of the human inhibitory receptor CD200R fused to the Fc portion of human IgG1 (see, Wright et al (2003) *J. Immunol.* 171:3034-3046, herein incorporated by reference in its entirety) was measured by surface plasmon resonance using a BIAcore 3000 system (BIAcore AB, Upsalla, Sweden). The assay format used the fusion protein captured by anti-human IgG Fcγ with a titration of anti-huCD200R antibody in the mobile phase. Approximately 5000 RUs of Affinipure F(ab')$_2$ Fragment goat anti-human IgG, Fcγ fragment specific (Jackson ImmunoResearch, Cat No. 109-006-098) were immobilized on a Sensor Chip CM5 (Research grade, BR-1000-14) via amine coupling chemistry. HBS-EP buffer (BR-1001-88) was used as the running buffer with a flow rate of 5 μL/min. Each analysis cycle was preceded by fresh loadings of the chip with huCD200R. Anti-huCD200R antibody at varying concentrations (133 and 13.3 nM) was injected over captured huCD200R surfaces at a flow rate of 5 μL/min. Following each injection cycle the CM5 chip surface was regenerated using a series of solutions (10 mM HCl and 10 mM Glycine pH 1.5) solution at a flow rate of 50 μL/min.

Background subtraction binding sensorgrams were used for analyzing the rate constant of association (ka) and dissociation (kd), and the equilibrium dissociation constant $K_D$. The resulting data sets were fitted with a bivalent analyte model using the BIAevaluation software (version 4.0.1).

TABLE 8

$K_d$ Values Determined by Biacore

| rat anti-human inhibitory CD200R mAb | Kd(pM) |
|---|---|
| DX182 | 24 |
| DX185 | 202 |
| DX178 | 1620 |
| DX177 | 1680 |
| DX184 | 1930 |
| DX176 | 7110 |

EXAMPLE 5

Mast Cell Degranulation Assay for Rat Anti-human Inhibitory CD200R Antibodies

The ability of the rat anti-human inhibitory CD200R antibodies to activate the human inhibitory CD200R was measured in a murine mast cell degranulation bioassay. A bone marrow derived murine mast cell line was transfected to express the human inhibitory CD200R and the ability of antibodies to inhibit mast cell degranulation assessed.

Materials and Methods

Mast Cell Line: The murine mast cell line was derived from the bone marrow of C57BL6 mice (Wright, G. J. et al., 2003, *J. Immunol.* 171:3034). cDNA encoding the full-length human CD200R was subcloned into the pMXneo retroviral expression vector (provided by T. Kitamura, University of Tokyo, Tokyo, Japan). Plasmid DNA was transfected into the Phoenix ecotropic virus packaging cell line (provided by Gary Nolan, Stanford University, Stanford, Calif.). and the viruses obtained were used to infect the murine mast cells, which were subsequently selected in media containing 1 mg/ml G418 (method in Onishi, M.et al., 1996, *Exp. Hematol.* 24:324). After 1-2 weeks in drug selection conditions, cells were analyzed by flow cytometry for expression of the receptor on the cell surface using receptor specific antibodies.

Degranulation Assay: Antibodies: DX176, DX177, DX178, DX184, DX185, DX182 and rat IgG2a (isotype control antibody, Phaminogen#553926). Stimulus: DX89 an anti-mouse CD200RLa (Murine activating CD200R)

Titrations of anti-CD200R antibodies or isotype control were made in a 96-well flat-bottom plate in 50 ul assay media (RPMI, 1% BSA, 25 mM Hepes). Murine mast cells expressing huCD200R (DT762) were spun down and resuspended at 4×10$^6$/ml, 50 ul/well was added to the antibody titrations and incubated for 20 min., room temperature. The stimulating antibody DX89 (anti-murine activating CD200R1a, Zhang, S et al (2004) J. Immunol. 173:6786) was then added in 50 ul/well so that the final concentration was 0.1 ug/ml. Cells were cultured at 37°, 5% $CO_2$ for 1 hr. At the end of the stimulation period, 20 ul was removed from each well and transfered to 60 ul 1.3 mg/ml Beta-hexosaminidase substrate (4-NitrophenyN-acetyl-b-D-glucosaminide, Sigma N9376). Supernatant/substrate reaction proceeded for 3.5 hr, 37° C. Reaction was stopped by the addition of 0.2M glycine, pH 10.7 and OD405-650 was measured using a microplate reader (Molecular Devices, Sunnyvale, Calif.) to assess the extent of degranulation. Results are provided in FIG. 7.

The IC50 for an anti-human inhibitory CD200R antibody of interest is the concentration of antibody required to inhibit the level of mast cell degranulation to about 50% of the level observed in the absence of any added anti-human inhibitory CD200R antibody.

EXAMPLE 6

Mast Cell Degranulation Assay for Humanized Rat Anti-human Inhibitory CD200R Antibody Mouse mast cells expressing human CD200R were used to assess the ability of humanized DX182 to inhibit degranulation. The humanized DX182 was also assessed for the ability to bind to cells as measured by flow cytometry.

Figure 8A:
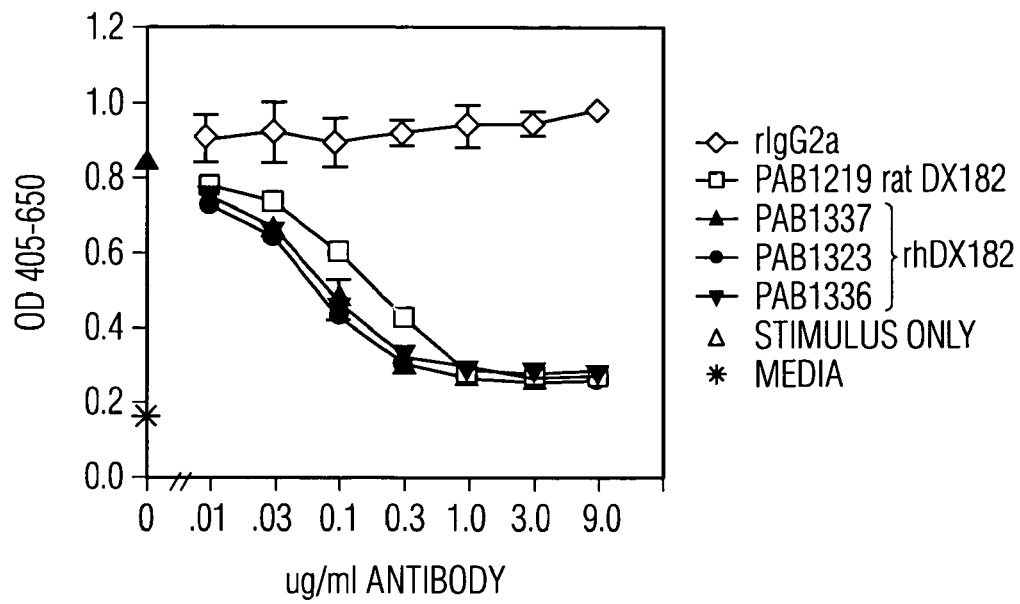
FIG. 8 shows the effects of the humanized anti-human CD200R antibody (huDX182) in a mast cell degranulation assay and the binding of huDX182.
Figure 8B:
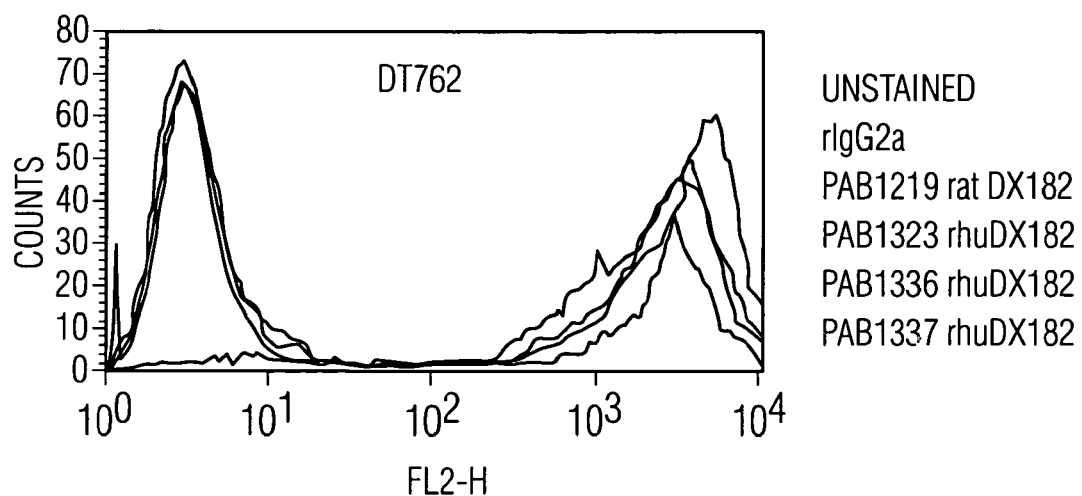

Materials and Methods:
  Cells: bone marrow derived murine mast cell line transfected to express human CD200R (DT762).
  Antibodies: PAB 1219, rat anti-human CD200R
    PAB 1337, recombinant human DX182
    PAB 1337, recombinant human DX182, bulk drug
    PAB 1336, (diluted PAB 1337)
    rat IgG2a, isotype control antibody, Pharmingen #553926
  Stimulus: DX89 anti-mouse CD200RLa (murine activating CD200R)
  Degranulation assay: The degranulation assay was done as described in Example 5. Titrations of anti-CD200R antibodies or isotype control were made in a 96-well flat-bottom plate in 50 ul assay media (RPMI, 1% BSA, 25 mM Hepes). Mouse mast cells expressing huCD200R (DT762) were spun down and resuspended at 4×10$^6$/ml, 50 ul/well was added to the antibody titrations and incubated for 20 min., room temperature. The stimulating antibody DX89 was then added in 50 ul/well so that the final concentration was 0.1 ug/ml. Cells were cultured at 37°, 5% $CO_2$ for 1 hr. At the end of the stimulation period, 20 ul was removed from each well and transferred to 60 ul 1.3 mg/ml Beta-hexosaminidase substrate (4-NitrophenyN-acetyl-b-D-glucosaminide, Sigma N9376). Supernatant/substrate reaction proceeded for 3.5 hr, 37° C. Reaction was stopped by the addition of 0.2M glycine, pH 10.7 and OD405-650 was measured to assess the extent of degranulation. The results are shown in FIG. 8.

Flow cytometry: Binding of anti-CD200R antibodies to cells expressing Cd200R was assessed by flow cytometry. DT762 cells were incubated with 10 ug/ml antibody, 5×10$^5$ cells in 100 ul assay media (D-PBS, 1% BSA, 0.05% NaN$_3$), 30 min., 4° C. Cells were washed and incubated with 10 ug/ml goat anti-rat PE (Caltag R40004-3) for rat DX182 or goat anti-human PE (Caltag H10104) for rhuDX182, 50 ul/sample, 20 min, 4° C. Cells were washed 2× post staining, resuspended in 250 ul, and analyzed using the FACSCaliber and accompanying software (B-D Biosciences). The results are shown in FIG. 8. as measured to assess the extent of degranulation. Results are provided in FIG. 7.

EXAMPLE 7

Mast Cell Degranulation Assay for mouse Anti-cyno Inhibitory CD200R Antibody (DX248)

Murine mast cells expressing human CD200R (DT762) were used to assess the ability of humanized DX182 to inhibit degranulation. The humanized DX182 was also assessed for the ability to bind to cells as measured by flow cytometry.

The degranulation assay was done as described in Example 5. Antibodies used (and lot numbers) were: rat anti-human CD200R, DX182, PAB 1219; recombinant human DX182, bulk drug, PAB 1337, SCH1372391; formulated SCH1372391 (diluted PAB 1337), PAB 1336; rat IgG2a, isotype control antibody, Pharmingen #553926.

Binding of anti-CD200R antibodies to DT762 cells was assessed by flow cytometry. DT762 cells were incubated with 10 ug/ml antibody, 5×10$^5$ cells in 100 ul assay media (D-PBS, 1% BSA, 0.05% NaN$_3$), 30 min., 4° C. Cells were washed and incubated with 10 ug/ml goat anti-rat PE (Caltag R40004-3) for rat DX182 or goat anti-human PE (Caltag H10104) for rhuDX182, 50 ul/sample, 20 min, 4° C. Cells were washed 2× post staining, resuspended in 250 ul, and analyzed using the FACSCaliber and accompanying software (BD Biosciences). Results are shown in FIG. 8. The unstained and isotype control cells are represented by the histograms on the left of the plot and the DX182 historgrams are shown on the far right of the plot.

Figure 10A:
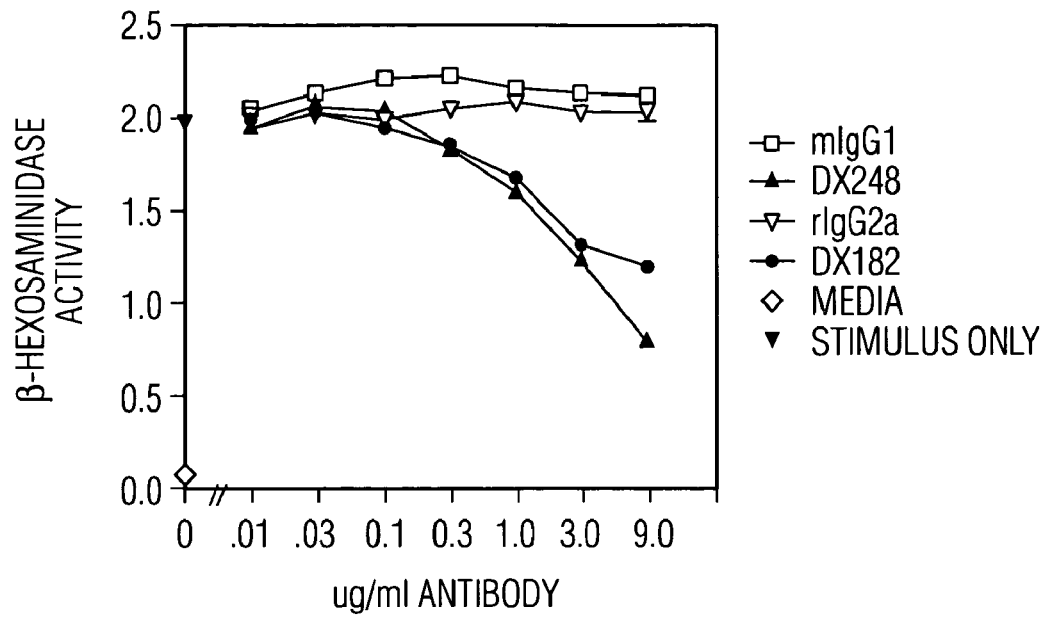
FIGS. 10A and 10B show the effects of mouse anti-cyno CD200R antibody DX248 and DX182 in a mast cell degranulation assay and the binding of mouse anti-cyno CD200R antibody and DX182.
Figure 10B:
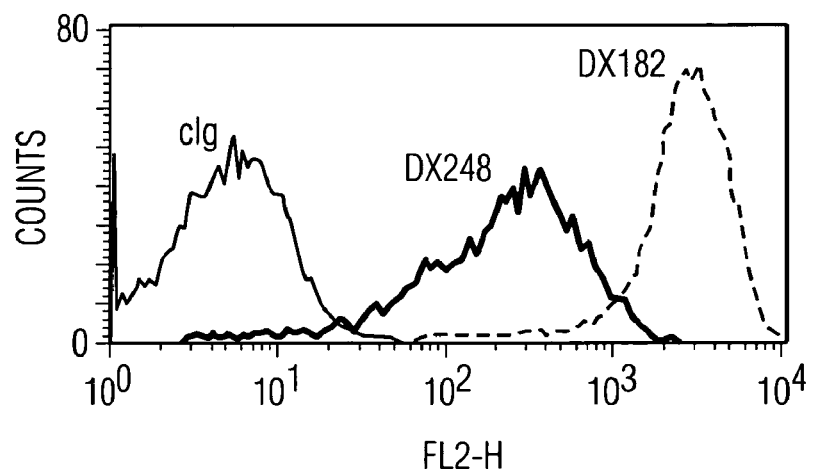

A human inhibitory CD200R fusion protein was used as the immunogen in female Balb/c mice to generate the mouse anti-cyno CD200R antibody DX248 using the same method as described in Example 1. The degranulation and flow cytometry methods were as described in Example 5. Antibodies (and lot numbers) used were: rat anti-human CD200R, DX182, PAB 1219; mouse anti-cynomolgus CD200R, DX248, PAB 766, rat IgG2a, isotype control antibody, Pharmingen #553926; mouse IgG1, isotype control antibody. DX248 bound to cells (FIG. 10B) and inhibited degranulation (FIG. 10A).

EXAMPLE 8

Determining the Equilibrium Dissociation Constant ($K_d$) for Rat Ant Human Inhibitory Cd200R Antibodies using Biacore Technology The kinetic binding activities of anti human inhibitory CD200R antibodies against a fusion protein consisting of the extracelleular domain of the human inhibitory receptor CD200R fused to the Fc portion of human IgG1 (see, Wright et al (2003) *J. Immunol* 171:3034-3046, herein incorporated by reference in its entirety) was measured by surface plasmon resonance using a BIAcore 3000 system (BIAcore AB, Upsalla, Sweden). The assay format used the fusion protein captured by anti-human IgG Fcγ with a titration of anti-huCD200R antibody in the mobile phase. Approximately 5000RUs of Affinipure F(ab')$_2$ Fragment goat anti-human IgG, Fcγ fragment specific (Jackson ImmunoResearch, Cat No. 109-006-098) were immobilized on a Sensor Chip CM5 (Research grade, BR-1000-14) via amine coupling chemistry. HBS-EP buffer (BR-1001-88) was used as the running buffer with a flow rate of 5 μL/min. Each analysis cycle was preceded by fresh loadings of the chip with huCD200R. Anti-huCD200R antibody at varying concentrations ranging from 0.82 to 600 nM (7 dilution points) was injected over captured huCD200R surfaces at a flow rate of 30 μL/min. Following each injection cycle the CM5 chip surface was regenerated using a series of solutions (10 mM Glycine pH 1.5 and 25 mM NaOH) solution at a flow rate of 75 μL/min.

Background subtraction binding sensorgrams were used for analyzing the rate constant of association (ka) and dissociation (kd), and the equilibrium dissociation constant $K_D$. The resulting data sets were fitted with a bivalent analyte model using the BIAevaluation software (version 4.0.1).

TABLE 9

| $K_d$ Values Determined by Biacore | |
|---|---|
| rat anti-human inhibitory CD200R mAb | Kd(pM) |
| DX182 | 760 |
| DX248 | 6 |

EXAMPLE 9

DX182 Recognizes Cynomolgus CD200R

Materials and methods: Cynomolgus mast cells were cultured from peripheral blood mononuclear cells in the presence of human stem cell factor and human IL-6. After three months of incubation, these cultures were 95% mast cells expressing CD117 and FceRI. The mast cells were cultured an additional 2 weeks in human IL-4 and human IgE to load and prime the FceRI expressed on the cell surface of these cells.

Figure 11:
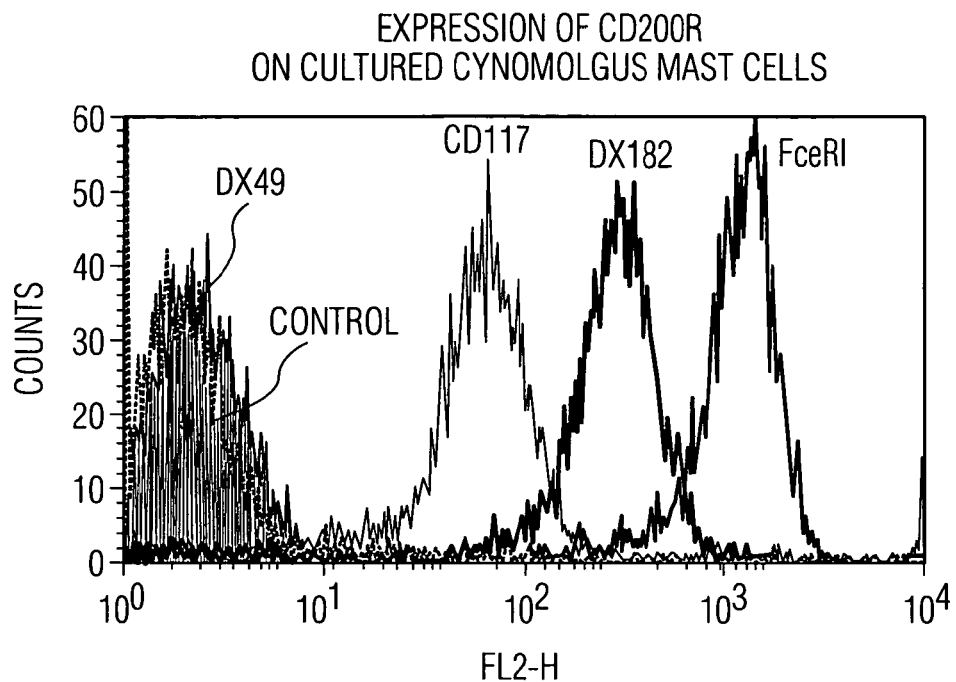
FIG. 11 shows expression of CD200R on cultured cynomolgus mast cells using DX182 (anti-huCD200R). Cultured peripheral blood derived cynomolgus mast cells were stained with control antibody, DX49 (isotype control for in vivo study), CD117 (stem cell factor receptor), DX182 (anti-huCD200R) and DX80 (FcεRI).

Flow cytometry: Cynomolgus mast cells were incubated with 10 ug/ml antibody, 5×10$^5$ cells in 100 ul assay media (D-PBS, 1% BSA, 0.05% NaN$_3$), 30 min., 4° C. Cells were washed and incubated with 10 ug/ml goat anti-rat PE (Caltag R40004-3) for rat DX182, rat DX49 or goat anti-mouse PE (Caltag M30004) for anti-CD117 and FceRI, 50 ul/sample, 20 min, 4° C. Cells were washed 2× post staining, resuspended in 250 ul, and analyzed using the FACSCaliber and accompanying software (B-D Biosciences). The results are shown in FIG. 11

Figure 12:
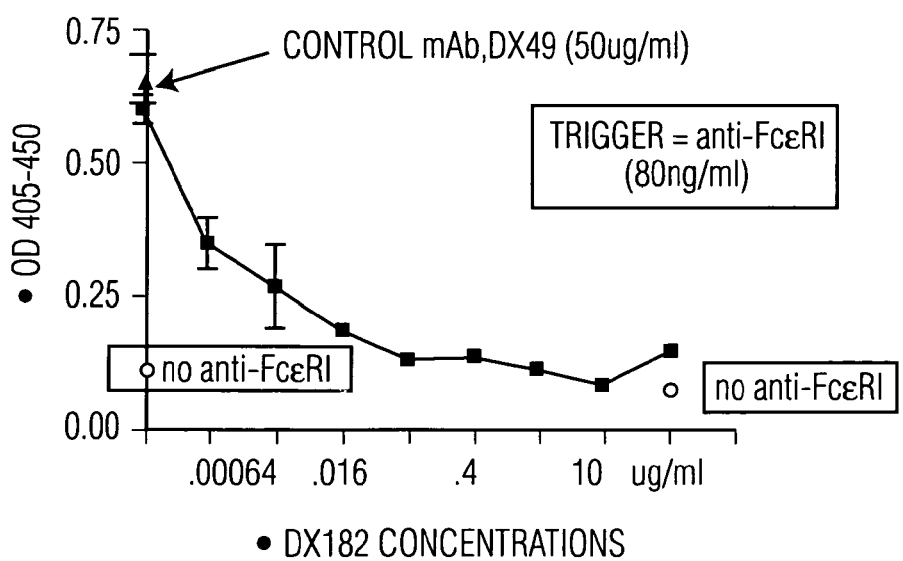
FIG. 12 shows DX182 inhibits cultured cynomolgus mast cell FcεR1 induced degranulation. Cultured cynomolgus mast cells were incubated with isotype control antibody, DX49 or anti-huCD200R antibody, DX182 and then triggered with an anti-FcεR1 antibody to induce degranulation. In a dose dependent fashion, DX182 inhibited the mast cell degranulation induced by triggering the FcεR1 receptor.

Degranulation assay: Titrations of anti-CD200R (DX182) antibody were made in a 96-well flat-bottom plate in 50 ul assay media (RPMI, 1% BSA, 25 mM Hepes). Cynomolgus mast cells expressing CD200R were spun down and resuspended at 4×10$^6$/ml, 50 ul/well was added to the antibody titrations and incubated for 20 min., room temperature. The cells were then washed in the plates two times and crosslinked with goat anti-rat (10 ug/ml). The stimulating antibody, anti- FceRI, was then added in 50 ul/well so that the final concentration was 80 ng/ml. Isotype control antibody was used at the maximum concentration of 50 ug/ml. Cells were cultured at 37°, 5% $CO_2$ for 1 hr. At the end of the stimulation period, 50 ul was removed from each well and degranulation was quantified by measuring the release of mast cell specific tryptase into the supernatants as previously published (Journal of Immunology, 2005, 174: 1348-1356). The results are shown in FIG. 12.

EXAMPLE 10

Ascaris-Allergic Cynomolgus Experiment

The following summarizes an experiment involving the treatment of two *Ascaris*-challenged Cynomolgus monkeys with the rat anti human inhibitory DX182. Subsequent to *Ascaris* challenge the two allergic monkeys treated with the rat anti-human CD200R antibody showed a rapid pronounced augmentation in airway resistance and a fall in blood pressure and increased heart rate.

Cynomolgus monkeys display a natural allergic hypersensitivity to *Ascaris* antigen inhalation. Inhalation of *Ascaris* antigen produces immediate mast cell-dependent bronchoconstriction that can be measured within 10-20 minutes after aerosol antigen exposure.

In in vitro experiments, DX182 and hu DX182 bound Cynomolgus CD200R and inhibited Cynomolgus monkey mast cell degranulation responses mediated via the FcξRI.

The pharmacokinetics (PK) and toxicity of DX182 antibody at a concentration of 8 mg/kg i.v. was evaluated in a small cohort of allergic and non-allergic Cynomolgus monkeys (2 allergic, 2 non-allergic) prior to *Ascaris* antigen inhalation. The PK of DX182 showed a half-life of 1.3 days. DX182 (8 mg/kg i.v.) was well tolerated and showed no overt adverse indications of systemic or cardiovascular toxicity in monkeys not challenged with antigen.

The effect the DX182 antibody on bronchoconstriction was evaluated in allergic Cynomolgus monkeys. *Ascaris*-allergic monkeys received either Dx182 (10 monkeys) or isotype control antibody (10 monkeys) at 8 mg/kg i.v. 48 hours prior to exposure to aerosol antigen exposure, and were subsequently monitored for increased airway resistance due to allergic bronchoconstriction. At the start of the antigen exposure phase, the study was terminated because upon inhalation exposure to antigen two monkeys treated with DX182 showed a rapid pronounced augmentation in airway resistance and a fall in blood pressure with increased heart rate. The monkeys receiving the isotype control antibody showed no unexpected physiological responses.

EXAMPLE 11

CD200R and CD200RLA Genes in Human and Cyno

Expression of a CD200RLa gene in Cynomolgus monkeys: Sequence alignment analysis of human and non-human primate CD200RLa genes demonstrated that the CD200RLa genes of Cynomolgus and Rhesus monkeys have maintained the two critical cysteines that are absent in the human and Chimpanzee CD200RLa genes. The inclusion of these cysteines in the sequence of Cynomolgus CD200RLa suggested that this gene could generate a functional cell surface protein capable of pairing with Dap12 and transmitting a potent activation signal if appropriately triggered. The sequence alignments are shown in FIG. 13.

Provided below is a human CD200R nucleic acid coding sequence and protein sequence and a human CD200RLa nucleic acid and protein sequence.

```
*HUMAN CD200R
ATGCTCTGCCCTTGGAGAACTGCTAACCTAGGGCTACTGTTGATTTTGAC

TATCTTCTTAGTGGCCGCTTCAAGCAGTTTATGTATGGATGAAAAACAGA

TTACACAGAACTACTCGAAAGTACTCGCAGAAGTTAACACTTCATGGCCT

GTAAAGATGGCTACAAATGCTGTGCTTTGTTGCCCTCCTATCGCATTAAG

AAATTTGATCATAATAACATGGGAAATAATCCTGAGAGGCCAGCCTTCCT

GCACAAAAGCCTACAGGAAAGAAACAAATGAGACCAAGGAAACCAACTGT

ACTGATGAGAGAATAACCTGGGTCTCCAGACCTGATCAGAATTCGGACCT

TCAGATTCGTCCAGTGGCCATCACTCATGACGGGTATTACAGATGCATAA

TGGTAACACCTGATGGGAATTTCCATCGTGGATATCACCTCCAAGTGTTA

GTTACACCTGAAGTGACCCTGTTTCAAAACAGGAATAGAACTGCAGTATG

CAAGGCAGTTGCAGGGAAGCCAGCTGCGCAGATCTCCTGGATCCCAGAGG

GCGATTGTGCCACTAAGCAAGAATACTGGAGCAATGGCACAGTGACTGTT

AAGAGTACATGCCACTGGGAGGTCCACAATGTGTCTACCGTGACCTGCCA

CGTCTCCCATTTGACTGGCAACAAGAGTCTGTACATAGAGCTACTTCCTG

TTCCAGGTGCCAAAAAATCAGCAAAATTATATATTCCATATATCATCCTT

ACTATTATTATTTTGACCATCGTGGGATTCATTTGGTTGTTGAAAGTCAA

TGGCTGCAGAAAATATAAATTGAATAAAACAGAATCTACTCCAGTTGTTG

AGGAGGATGAAATGCAGCCCTATGCCAGCTACACAGAGAAGAACAATCCT

CTCTATGATACTACAAACAAGGTGAAGGCATCTCAGGCATTACAAAGTGA

AGTTGACACAGACCTCCATACTTTATAA

*Human CD200R
MLCPWRTANLGLLLILTIFLVAASSSLCMDEKQITQNYSKVLAEVNTSWP

VKMATNAVLCCPPIALRNLIIITWEIILRGQPSCTKAYRKETNETKETNC

TDERITWVSRPDQNSDLQIRPVAITHDGYYRCIMVTPDGNFHRGYHLQVL

VTPEVTLFQNRNRTAVCKAVAGKPAAQISWIPEGDCATKQEYWSNGTVTV

KSTCHWEVHNVSTVTCHVSHLTGNKSLYIELLPVPGAKKSAKLYIPYIIL

TIIILTIVGFIWLLKVNGCRKYKLNKTESTPVVEEDEMQPYASYTEKNNP

LYDTTNKVKASEALQSEVDTDLHTL

*Human CD200RLa
ATGTCAGCTCCAAGATTACTGATTTCCATCATTATCATGGTGTCTGCTTC

AAGTAGTTCATGCATGGGTGGAAAGCAGATGACACAGAACTATTCAACAA

TTTTTGCAGAAGGTAACATTTCACAGCCTGTACTGATGGATATAAATGCT

GTGCTTTGTTGCCCTCCTATCGCATTAAGAAATTTGATCATAATAACATG

GGAAATAATCCTGAGAGGCCAGCCTTCCTGCACAAAAGCCTACAAGAAAG

AAACAAATGAGACCAAGGAAACCAACTGTACTGTTGAGAGAATAACCTGG

GTCTCTAGACCTGATCAGAATTCGGACCTTCAGATTCTTCCGGTGGACAC

CACTCATGACGGGTATTACAGAGGCATAGTGGTAACACCTGATGGGAATT

TCCATCGTGGATATCACCTCCAAGTGTTAGTTACACCCGAAGTGAACCTA

TTTCAAAGCAGGAATATAACTGCAGTATGCAAGGCAGTTACAGGGAAGCC
```

-continued

AGCTGCCCAGATCTCCTGGATCCCAGAGGGATCTATTCTTGCCACTAAGC

AAGAATACTGGGGCAATGGCACAGTGACGGTTAAGAGTACATGCCCCTGG

GAGGGCCACAAGTCTACTGTGACCTGCCATGTCTCCCATTTGACTGGCAA

CAAGAGTCTGTCCGTAAAGTTGAATTCAGGTCTCAGAACCTCAGGATCTC

CAGCGTTGTCCTTACTGATCATTCTTTATGTGAAACTCTCTCTTTTTGTG

GTCATTCTGGTCACCACAGGATTTGTTTTCTTCCAGAGGATAAATCATGT

CAGAAAAGTTCTTTAA

*Human CD200RLa
MSAPRLLISIIIMVSASSSSCMGGKQMTQNYSTIFAEGNISQPVLMDINA

VLCCPPIALRNLIIITWEIILRGQPSCTKAYKKETNETKETNCTVERITW

VSRPDQNSDLQILPVDTTHDGYYRGIVVTPDGNFHRGYHLQVLVTPEVNL

FQSRNITAVCKAVTGKPAAQISWIPEGSILATKQEYWGNGTVTVKSTCPW

EGHKSTVTCHVSHLTGNKSLSVKLNSGLRTSGSPALSLLIILYVKLSLFV

VILVTTGFVFFQRINHVRKVL

Provided below is a nucleic acid coding sequence for the human CYS mutated CD200RLa and a protein sequence for the Human CYS mutated CD200RLa. CYS Mutated CD200RLa was obtained by cite directed mutagenesis of human CD200RLa. Primers utilized in the site directed mutagenesis are as follows:

```
ACGGGTATTACAGATGCATAGTGGTAACAC;
GTGTTACCACTATGCATCTGTAATACCCGT;
CAGAGGGATCTATTTGTGCCACTAAGCAAG;
CTTGCTTAGTGGCACAAATAGATCCCTCTG.
```

*Human CD200RLa-Cys-mut
ATGTCAGCTCCAAGATTACTGATTTCCATCATTATCATGGTGTCTGCTTC

AAGTAGTTCATGCATGGGTGGAAAGCAGATGACACAGAACTATTCAACAA

TTTTTGCAGAAGGTAACATTTCACAGCCTGTACTGATGGATATAAATGCT

GTGCTTTGTTCCCCTCCTATCGCATTAAGAAATTTGATCATAATAACATG

GGAAATAATCCTGAGAGGCCAGCCTTCCTGCACAAAAGCCTACAAGAAAG

AAACAAATGAGACCAAGGAAACCAACTGTACTGTTGAGAGAATAACCTGG

GTCTCTAGACCTGATCAGAATTCGGACCTTCAGATTCTTCCGGTGGACAC

CACTCATGACGGGTATTACAGATGCATAGTGGTAACACCTGATGGGAATT

TCCATCGTGGATATCACCTCCAAGTGTTAGTTACACCCGAAGTGAACCTA

TTTCAAAGCAGGAATATAACTGCAGTATGCAAGGCAGTTACAGGGAAGCC

AGCTGCCCAGATCTCCTGGATCCCAGAGGGATCTATTTGTGCCACTAAGC

AAGAATACTGGGGCAATGGCACAGTCACGGTTAAGAGTACATGCCCCTGG

GAGGGCCACAAGTCTACTGTGACCTGCCATGTCTCCCATTTGACTGGCAA

CAAGAGTCTGTCCGTAAAGTTGAATTCAGGTCTCAGAACCTCAGGATCTC

CAGCGTTGTCCTTACTGATCATTCTTTATGTGAAACTCTCTCTTTTTGTG

GTCATTCTGGTCACCACAGGATTTGTTTTCTTCCAGAGGATAAATCATGT

CAGAAAAGTTCTTTAA

*Human CD200RLa-Cys-mut
MSAPRLLISIIIMVSASSSSCMGGKQMTQNYSTIFAEGNISQPVLMDINA

VLCCPPIALRNLIIITWEIILRGQPSCTKAYKKETNETKETNCTVERITW

VSRPDQNSDLQILPVDTTHDGYYRCIVVTPDGNFHRGYHLQVLVTPEVNL

FQSRNITAVCKAVTGKPAAQISWIPEGSICATKQEYWGNGTVTVKSTCPW

EGHKSTVTCHVSHLTGNKSLSVKLNSGLRTSGSPALSLLIILYVKLSLFV

VILVTTGFVFFQRINHVRKVL

The following primers were used to obtain the cynoCD200RLa from a cyno mast cell cDNA library: CAAATGCACACTTTAGGAAAGATG and CTTCCTCTT-TAAAGAGATTTTCTG. The following primers were used to obtain the cyno inhibitory CD200R cDNA from a cyno lung cDNA library: ATGCTCTGCCCTTGGAGAAC and AGAGTCCAACAACTTATAAAGT.

*cynoCD200RLa
ATGTCAGCTTCAAGATTACTGATCTCCATCATTATCATGGTGTCTGCTTC

AAGTAGTTCATGTATGGATGGAAAGCAGATGACACAGAATTATTCAAAAA

TGTCTGCAGAAGGTAACATTTCACAGCCTGTACTGATGGATACAAATGCT

ATGCTTTGTTGCCCTCCTATTGAGTTCAGAAATTTGATCGTAATAGTATG

GGAAATAATCATAAGAGGCCAGCCTTCCTGCACAAAAGCCTACAGGAAAG

AAACAAATGAGACCAAGGAAACCAACTGTACTGATAAGAGAATAACCTGG

GTCTCCACACCTGATCAGAATTCGGACCTTCAGATTCACCCAGTGGCCAT

CACTCATGACGGATATTACAGATGCATAATGGCAACTCCTGATGGGAATT

TCCATCGTGGCTATCACCTCCAAGTGTTAGTTACACCTGAAGTGACCCTG

TTTCAAAGCAGGAATAGAACTGCAGTATGCAAGGCAGTTGCAGGGAAGCC

AGCTGCTCAGATCTCCTGGATCCCAGCGGGGATTGTGCCCCTACTGAGC

ATGAGTACTGGGGCAATGGCACAGTGACTGTTGAGAGTATGTGCCACTGG

GGGGACCACAATGCGTCTACCGTGACCTGCCATGTCTCCCATTTGACTGG

CAACAAGAGTCTGTACATAAAGTTGAATTCAGGTCTCAGAACCTCAGGAT

CTCCAGCGTTGGACTTACTGATCATTCTTTATGTGAAACTCTCTCTTTTT

GTGGTCATTCTGGTCACCACAGGATTTGTTTTCTTCCAGAGGATAAATTA

TGTCAGAAAATCTCTTTAA

*cynoCD200RLa
MSASRLLISIIIMVSASSSSCMDGKQMTQNYSKMSAEGNISQPVLMDTNA

NLCCPPIEFRNLIVIVWEIIRGQPSCTKAYRKETNETKETNCTDKRITW

VSTPDQNSDLQIHPVAITHDGYYRCIMATPDGNFHRGYHLQVLVTPEVTL

FQSRNRTAVCKAVAGKPAAQISWIPAGDCAPTEHEYWGNGTVTVESMCHW

GDHNASTVTCHVSHLTGNKSLYIKLNSGLRTSGSPALDLLIILYVKLSLF

VVILVTTGFVFFQRINYVRKSL

*cynoCD200R
ATGCTCTGCCCTTGGAGAACTGCTAATCTAGGGCTACTGTTGATTTTGGC

TGTCTTCTTAGTGGCTGCTTCAAACAGTTTATGTATGGATGAAAAACAGA

-continued

```
TTACACAGAACCACTCAAAAGTACTCGCAGAAGTTAACATTTCATGGCCT

GTACAGATGGCTAGAAATGCTGTGCTTTGTTGCCCTCCTATTGAGTTCAG

AAATTTGATCGTAATAACATGGGAAATAATCCTAAGAGGCCAGCCTTCCT

GCACAAAAACCTACAGGAAAGACACAAATGAGACCAAGGAAACCAACTGT

ACTGATGAGAGAATAACCTGGGTCTCCACACCTGATCAGAATTCAGACCT

TCAGATTCACCCAGTGGCCATCACTCATGACGGGTATTACAGATGCATAA

TGGCAACTCCTGATGGGAATTTCCATCGTGGATATCACCTCCAAGTGCTA

GTTACACCTGAAGTGACCCTGTTTGAAAGCAGGAATAGAACTGCAGTATG

CAAGGCAGTTGCAGGGAAGCCAGCTGCGCAGATCTCCTGGATCCCAGCGG

GGGATTGTGCCCCTACTGAGCAAGAGTACTGGGGCAATGGCACAGTGACT

GTTAAGAGTACATGCCACTGGGAAGGCCACAATGTGTCTACCGTGACCTG

CCATGTCTCCCATTTGACTGGCAACAAGAGTCTGTACATAGAGCTACTTC

CTGTTCCAGGTGCCAAAAAATCAGCAAAATTATATATGCCATATGTCATC

CTTACTATTATTATTTTGACCATCGTGGGATTCATTTGGTTATTGAAAAT

CAGTGGCTGCAGAAAATATAATTTGAATAAAACAGAATCTACTTCAGTTG

TTGAGGAGGATGAAATGCAGCCCTATGCCAGCTACACAGAGAAAAACAAT

CCTCTCTATGATACTACAAACAAGGTGAAAGCGTCTCAGGCATTACAAAG

TGAAGTTGGCACAGACCTCCATACTTTATAA

*cynoCD200R
MLCPWRTANLGLLLILAVFLVAASNSLCMDEKQITQNHSKVLAEVNISWP

VQMARNAVLCCPPIEFRNLIVITWEIILRGQPSCTKTYRKDTNETKETNC

TDERITWVSTPDQNSDLQIHPVAITHDGYYRCIMATPDGNFHRGYHLQVL

VTPEVTLFESRNRTAVCKAVAGKPAAQISWIPAGDCAPTEQEYWGNGTVT

VKSTCHWEGHNVSTVTCHVSHLTGNKSLYIELLPVPGAKKSAKLYMPYVI

LTIIILTIVGFIWLLKISGCRKYNLNKTESTSVVEEDEMQPYASYTEKNN

PLYDTTNKVKASQALQSEVGTDLHTL
```

Transfection of Mouse Mast Cells with the Cynomolgus CD200RLa: The ability of the rat anti-human CD200R antibody DX182 to bind to the cynomolgus activating CD200RLa was assessed by flow cytometry. A murine mast cell line or the pre-B cell line Ba/F3 (provided by T. Kitamura, University of Tokyo, Tokyo, Japan) were transfected to express the cyno CD200RLa using methods described in Example 5. For expression of the CD200RLa protein in BaF/3, it was necessary to co-express the signaling molecule DAP12 (Lanier, L. L et al, 1998, *Nature* 391:703) containing a FLAG epitope at the N terminus to permit detection using an anti-FLAG antibody. In the absence of a pairing partner, FLAG-tagged DAP12 remains within the cytoplasm of Ba/F3. However, if DAP12 associating receptors are present they can pair with DAP12 through the interactions of oppositely charged residues in the transmembrane domains, resulting in the FLAG epitope appearing on the cell surface. Mouse mast cells express endogenous DAP12 which can associate with CD200RLa proteins from different species. Introduction of the cyno CD200RLa gene into mouse mast cells and Ba/F3-DAP12 cells confirmed that this protein could be expressed on the cell surface of cells and that it was recognized by the anti-human CD200R antibody DX182. Results are shown in FIG. 14.

Figure 15:
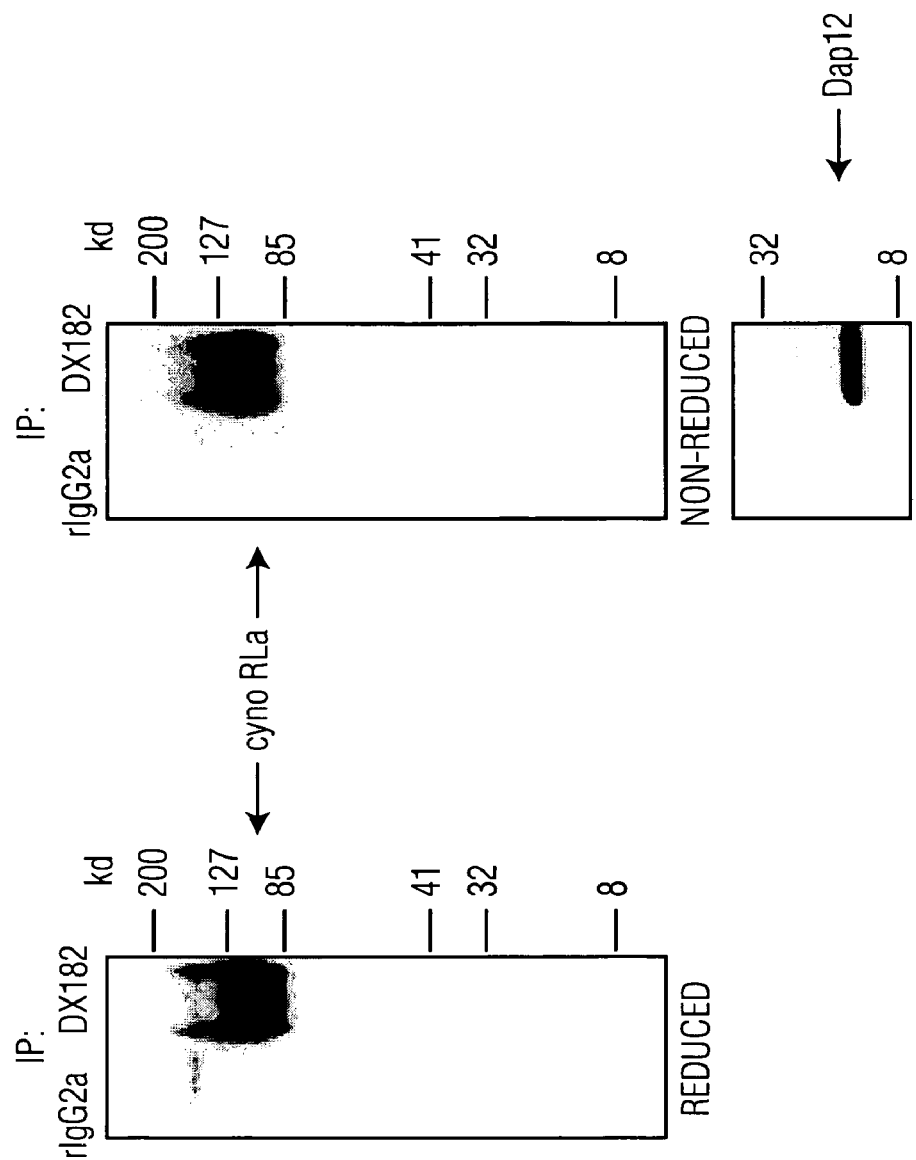
FIG. 15 shows cynoCD200RLa is a single polypeptide chain that pairs with Dap 12. Mouse mast cells transfected with cynomolgus CD200RLa were immunoprecipitated with control antibody or DX182. DX182 immunoprecipitated cynomolgus CD200RLa from these transfectants. Western blotting for Dap12 shows that cynomolgus CD200RLa is associated with this signal adaptor protein.

The association of the cyno CD200RLa cell surface expressed receptor with the signaling adapter molecule DAP12 was confirmed by biochemistry. The cell surface of mast cells expressing the cyno CD200RLa was labeled with biotin using EZ-link sulfo-N-hydroxy-succinimide-biotin (Pierce). Cells were washed with D-PBS then lysed in 1% digitonin (Cabiochem), 0.12% triton X-100, 150 mM NaCl, 20 mM triethanolamine, containing protease inhibitors (complete protease inhibitor mixture; Roche Molecular Biochemicals). Lysates were spun 12,000×g for 20 minutes at 4° C. Immunoprecipitations were done by incubating precleared lysates with 1-2 μg of anti-CD200R DX182 or isotype control (rat IgG2a, BD Pharmingen, #553926) and protein A and protein G sepharose beads. Beads were washed, and eluted proteins were resolved on 4-20% Tris-glycine gels (Invitrogen/Novex) and transferred to Immobilon-P (Millipore). Membranes were blocked in 5% BSA, 0.1% Tween-20 in TBS (10 mM Tris, pH 8.0, 150 mM NaCl) then blotted with strepavidin-HRP (Amersham Biosciences), washed in TBS, 0.1% Tween-20, visualized after incubating the membrane in Super Signal West dura chemiluminescent substrate (Pierce) and then exposing to film. DAP12 does not cell surface label with biotin due to its short extracellular domain, therefore the membrane was probed with a rabbit anti-mouse DAP12 antibody followed by protein A-HRP (Amersham Biosciences), and visualized as described above. DAP12 was found in the DX182 immunoprecipitations confirming the association with the cyno activating CD200RLa. Results are shown in FIG. 15.

Figure 16:
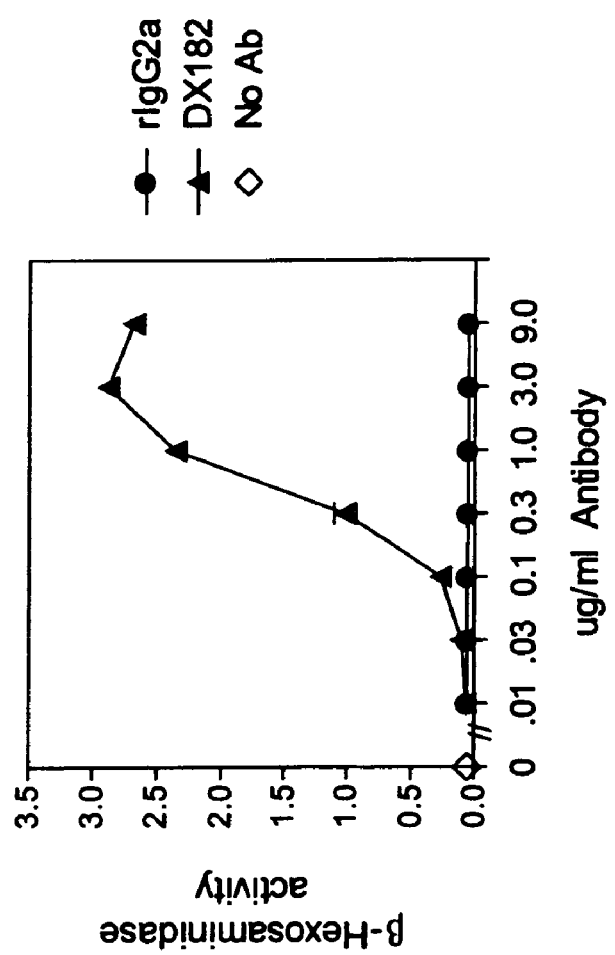
FIG. 16 shows DX182 induces degranulation of mouse mast cells expressing Cynomolgus CD200RLa. Mouse mast cells transfected with cynomolgus CD200RLa were incubated with DX182 and assayed for mast cell degranulation. DX182 induced a potent mast cell degranulation.

DX182 was shown to be an activator of cynomolgus CD200RLa expressed in murine mast cells by inducing a mast cell degranulation response. The degranulation assay was done as described in Example 5 using the murine mast cells expressing cyno CD200RLa described in Example 11. Results are shown in FIG. 16.

Lack of Expression of CD200RLa on Human Macrophage and Myeloid Cells. The human genome has only two CD200R family members: CD200R and CD200RLa (Wright, G. J. et al (2003) *J. Immunol.* 171:3034-3046). Similar to the mouse CD200RLa gene, human CD200RLa contains a charged residue in the transmembrane sequence suggesting the potential to interact with DAP12 and transmit an activation signal. While the mouse CD200RLa genes are readily expressed in most macrophage/myeloid cells and easily transfectable in mouse cell lines containing Dap12, human CD200RLa demonstrated extremely low transcription levels in human macrophage/myeloid cells and was incapable of cell surface expression in transfectable cell lines containing Dap12.

As shown in FIG. 13, human and chimp CD200RLa lack two cysteine residues conserved in all other members of the CD200R family. Without being bound by theory, it is believed that the inability of the human CD200R1a to form a functional receptor was due to the mutation of two the cysteines residues in the extracellular domain to glycine or isoleucine residues. Mutation of the huCD200RLa gene to encode the two cysteines that were lacking in the genomic sequence enabled the expression of the human CD200RLa receptor at the cell surface in association with Dap12.

The determination of whether anti-CD200R antibodies bind to the human CD200RLa, cyno CD200R and cyno CD200RLa proteins was done by ELISA or flow cytometry. Fusion proteins consisting of the human CD200RLa extracellular domain fused to the Fc region of human IgG1 were made in which two residues (glycine and isoleucine) were mutated to cysteines to make the protein more similar to cynomolgus and rhesus CD200RLa and the human and cyno CD200R proteins (see FIG. 13). The proteins were expressed as described in Example 5. The wild-type form of the protein was also made but expression was considerably reduced compared to the CYS mutated protein.

Similarly, the full length human CD200RLa cDNA containing the wild type or CYS-mutated residues was generated. The cDNAs were cloned into the pMXpie retroviral vector and introduced into Ba/F3 cells expressing human DAP12 as described in Example 11. The pMXpie vector is similar to the pMXneo vector (see Example 5) but has additional IRES-GFP sequences inserted 3' of the coding sequence enabling detection of the vector encoded proteins by fluorescence. The neomycin resistance gene is replaced with the puromycin resistance gene and cells are drug selected using 1 ug/ml puromycin (Sigma-Aldrich).

The CYS mutated form of the receptor was expressed on the cell surface as detected by FACS staining using the anti-FLAG epitope antibody M2 (Sigma-Aldrich). The wild-type receptor was not detected at the cell surface.

DX182 did not bind to the wild-type or CYS mutated human CD200RLa when expressed as a fusion protein using a standard indirect ELISA protocol. DX182 also failed to bind to Ba/F3 cells expressing CYS mutated human CD200RLa at the cell surface.

In a preferred embodiment of the invention, the anti human inhibitory antibody of the invention specifically binds the human inhibitory CD200R receptor but does not specifically bind the CYS mutated human CD200RLa or a human CD200RLa fusion protein (extracellular domain of human CD200RLa fused to the Fc portion of human IgG1, see, e.g. Example 13).

Methods of expressing CD200R and CD200RLa (CYS mutated form) are described herein above. By way of example, and not limitation specificity of binding of an anti CD200R antibody may be assessed by the assay described above. Results for DX182, DX248, DX185, Dx178, DX184 and DX176 are shown in the table below.

| Antibody | Binding to huCD200RLa | Binding to cynoCD200R | Binding to cynoCD200RLa | Blocks Ligand Binding |
|---|---|---|---|---|
| DX182 | No | Yes | Yes | Yes |
| DX248 | No | Yes | No | Not done |
| DX185 | No | Yes | Yes | Yes |
| DX178 | No | No | No | Yes |
| DX184 | No | Yes | Yes | Yes |
| DX176 | No | No | No | Yes |

Citation of the above publications or documents is not intended as an admission that any of the foregoing is pertinent prior art, nor does it constitute any admission as to the contents or date of these publications or documents. All references cited herein are incorporated by reference to the same extent as if each individual publication, patent application, or patent, was specifically and individually indicated to be incorporated by reference.

What is claimed is:

1. An isolated binding compound that binds to a human inhibitory CD200R, comprising:
    at least one antibody light chain variable region; and
    at least one antibody heavy chain variable region,
    wherein the light chain variable region comprises the CDR sequences of SEQ ID NOs: 1, 2 and 3 and wherein the heavy chain variable region comprises the CDR sequences of SEQ ID NOs: 19, 20 and 21.

2. The binding compound of claim 1, wherein the binding compound is an antibody comprising:
    a light chain variable region that comprises SEQ ID NO: 42; and
    a heavy chain variable region that comprises SEQ ID NO: 48.

3. The binding compound of claim 1, wherein the light chain consists essentially of SEQ ID NO: 49 having up to ten conservative substitutions and the heavy chain consists essentially of SEQ ID NO: 50 having up to ten conservative substitutions.

4. An isolated anti-human inhibitory CD200R antibody, wherein the mature antibody sequence is encoded by the expression vector having ATCC Accession No. PTA-8067 deposited Dec. 6, 2006.

5. An isolated antibody that is able to cross-block binding of the binding compound of claim 4 to human inhibitory CD200R in a cross-blocking assay.

6. The binding compound of claim 1, wherein the binding compound is a humanized monoclonal antibody.

7. The binding compound of claim 1, wherein the binding compound is a fully-human monoclonal antibody.

8. The binding compound of claim 7, wherein the binding compound is an agonist humanized monoclonal antibody.

9. A composition comprising:
    a binding compound that binds to human inhibitory CD200R and activates the human inhibitory receptor, wherein the binding compound comprises an antibody light chain variable region and an antibody heavy chain variable regions, wherein the light chain variable region comprises SEQ ID NO: 42 and the heavy chain variable region comprises SEQ ID NO: 48; and a pharmaceutically acceptable carrier or diluent.

10. The composition of claim 9, further comprising another immunosuppressive or anti-inflammatory agent.

11. The binding compound of claim 1, further comprising a heavy chain constant region, wherein the heavy chain constant region comprises a γ1, γ2, γ3, or γ4 human heavy chain constant region or a variant thereof.

12. The binding compound of claim 11, comprising a γ1 human heavy chain constant region or a variant thereof.

13. The binding compound of claim 1, further comprising a light chain constant region, wherein the light chain constant region comprises a kappa human light chain constant region.

14. The binding compound of claim 1, wherein the binding compound is an antibody fragment selected from the group consisting of Fab, Fab', Fab'-SH, Fv, scFv, F(ab')$_2$, and a diabody.

15. The binding compound of claim 1, wherein the binding compound activates the human inhibitory CD200R.

* * * * *

SEQUENCE LISTING

<160> NUMBER OF SEQ ID NOS: 63

<210> SEQ ID NO 1
<211> LENGTH: 11
<212> TYPE: PRT
<213> ORGANISM: Rattus norvegicus

<400> SEQUENCE: 1

Lys Ala Ser Lys Asn Ile Arg Ser Tyr Leu Ala
1               5                   10

<210> SEQ ID NO 2
<211> LENGTH: 7
<212> TYPE: PRT
<213> ORGANISM: Rattus norvegicus

<400> SEQUENCE: 2

Ser Gly Ser Thr Leu His Ser
1               5

<210> SEQ ID NO 3
<211> LENGTH: 9
<212> TYPE: PRT
<213> ORGANISM: Rattus norvegicus

<400> SEQUENCE: 3

Gln Gln His His Glu Tyr Pro Leu Thr
1               5

<210> SEQ ID NO 4
<211> LENGTH: 11
<212> TYPE: PRT
<213> ORGANISM: Rattus norvegicus -continued

```
<400> SEQUENCE: 4

Lys Ala Ser Lys Asn Ile Arg Ser Tyr Leu Ala
1               5                   10

<210> SEQ ID NO 5
<211> LENGTH: 7
<212> TYPE: PRT
<213> ORGANISM: Rattus norvegicus

<400> SEQUENCE: 5

Ser Gly Ser Thr Leu His Ser
1               5

<210> SEQ ID NO 6
<211> LENGTH: 9
<212> TYPE: PRT
<213> ORGANISM: Rattus norvegicus

<400> SEQUENCE: 6

Gln Gln His His Glu Tyr Pro Leu Thr
1               5

<210> SEQ ID NO 7
<211> LENGTH: 11
<212> TYPE: PRT
<213> ORGANISM: Rattus norvegicus

<400> SEQUENCE: 7

Lys Ala Gly Lys Asn Ile Asn Thr Asn Leu Ala
1               5                   10

<210> SEQ ID NO 8
<211> LENGTH: 7
<212> TYPE: PRT
<213> ORGANISM: Rattus norvegicus

<400> SEQUENCE: 8

Ser Gly Ser Thr Leu Gln Ser
1               5

<210> SEQ ID NO 9
<211> LENGTH: 9
<212> TYPE: PRT
<213> ORGANISM: Rattus norvegicus

<400> SEQUENCE: 9

Gln Gln His Asn Glu Phe Pro Leu Thr
1               5

<210> SEQ ID NO 10
<211> LENGTH: 11
<212> TYPE: PRT
<213> ORGANISM: Rattus norvegicus

<400> SEQUENCE: 10

Lys Ala Ser Lys Asn Ile Ser Lys Tyr Leu Ala
1               5                   10

<210> SEQ ID NO 11
<211> LENGTH: 7
<212> TYPE: PRT
<213> ORGANISM: Rattus norvegicus

<400> SEQUENCE: 11

Ser Gly Ser Thr Leu Gln Ser
```

-continued

```
1               5

<210> SEQ ID NO 12
<211> LENGTH: 9
<212> TYPE: PRT
<213> ORGANISM: Rattus norvegicus

<400> SEQUENCE: 12

Gln Gln His Asn Glu Phe Pro Leu Thr
1               5

<210> SEQ ID NO 13
<211> LENGTH: 11
<212> TYPE: PRT
<213> ORGANISM: Rattus norvegicus

<400> SEQUENCE: 13

Lys Ala Ser Gln Asn Val Gly Ser Asn Val Asp
1               5                   10

<210> SEQ ID NO 14
<211> LENGTH: 7
<212> TYPE: PRT
<213> ORGANISM: Rattus norvegicus

<400> SEQUENCE: 14

Lys Ala Ser Asn Arg Tyr Thr
1               5

<210> SEQ ID NO 15
<211> LENGTH: 9
<212> TYPE: PRT
<213> ORGANISM: Rattus norvegicus

<400> SEQUENCE: 15

Met Gln Ser Leu Ser Phe Pro Tyr Thr
1               5

<210> SEQ ID NO 16
<211> LENGTH: 11
<212> TYPE: PRT
<213> ORGANISM: Mouse

<400> SEQUENCE: 16

Gln Ala Ser Gln Gly Thr Ser Ile Asn Leu Asn
1               5                   10

<210> SEQ ID NO 17
<211> LENGTH: 7
<212> TYPE: PRT
<213> ORGANISM: Mouse

<400> SEQUENCE: 17

Ser Ala Asn Asn Leu Glu Asp
1               5

<210> SEQ ID NO 18
<211> LENGTH: 9
<212> TYPE: PRT
<213> ORGANISM: Mouse

<400> SEQUENCE: 18

Leu Gln Ile Thr Tyr Leu Pro Trp Thr
1               5
```

```
<210> SEQ ID NO 19
<211> LENGTH: 11
<212> TYPE: PRT
<213> ORGANISM: Rattus norvegicus

<400> SEQUENCE: 19

Gly Tyr Thr Ile Thr Ser Gly Tyr Asp Trp Ser
1               5                   10

<210> SEQ ID NO 20
<211> LENGTH: 16
<212> TYPE: PRT
<213> ORGANISM: Rattus norvegicus

<400> SEQUENCE: 20

Tyr Ile Asn Tyr Gly Gly Ser Thr Asn Tyr Lys Pro Ser Leu Gly Ser
1               5                   10                  15

<210> SEQ ID NO 21
<211> LENGTH: 15
<212> TYPE: PRT
<213> ORGANISM: Rattus norvegicus

<400> SEQUENCE: 21

Tyr Asn Glu Tyr Lys Ser Tyr Ile Tyr Asp Trp Tyr Phe Asp Phe
1               5                   10                  15

<210> SEQ ID NO 22
<211> LENGTH: 11
<212> TYPE: PRT
<213> ORGANISM: Rattus norvegicus

<400> SEQUENCE: 22

Gly Tyr Thr Ile Thr Ser Gly Tyr Asp Trp Ser
1               5                   10

<210> SEQ ID NO 23
<211> LENGTH: 16
<212> TYPE: PRT
<213> ORGANISM: Rattus norvegicus

<400> SEQUENCE: 23

Tyr Ile Asn Tyr Gly Gly Ser Thr Asn Tyr Lys Pro Ser Leu Gly Ser
1               5                   10                  15

<210> SEQ ID NO 24
<211> LENGTH: 15
<212> TYPE: PRT
<213> ORGANISM: Rattus norvegicus

<400> SEQUENCE: 24

Tyr Asn Glu Tyr Lys Ser Tyr Ile Tyr Asp Trp Tyr Phe Asp Phe
1               5                   10                  15

<210> SEQ ID NO 25
<211> LENGTH: 11
<212> TYPE: PRT
<213> ORGANISM: Rattus norvegicus

<400> SEQUENCE: 25

Gly Tyr Thr Ile Thr Ser Gly Tyr Asp Trp Ser
1               5                   10

<210> SEQ ID NO 26
<211> LENGTH: 16
<212> TYPE: PRT
```

-continued

<213> ORGANISM: Rattus norvegicus

<400> SEQUENCE: 26

Tyr Ile Asn Tyr Ser Gly Ser Thr Val Tyr Asn Pro Ser Leu Arg Ser
1               5                   10                  15

<210> SEQ ID NO 27
<211> LENGTH: 15
<212> TYPE: PRT
<213> ORGANISM: Rattus norvegicus

<400> SEQUENCE: 27

Phe Glu Ala Ser Asn Thr Tyr Leu Tyr Asp Trp Tyr Phe Asp Phe
1               5                   10                  15

<210> SEQ ID NO 28
<211> LENGTH: 11
<212> TYPE: PRT
<213> ORGANISM: Rattus norvegicus

<400> SEQUENCE: 28

Gly Phe Thr Ile Thr Ser Gly Tyr Asp Trp Ser
1               5                   10

<210> SEQ ID NO 29
<211> LENGTH: 16
<212> TYPE: PRT
<213> ORGANISM: Rattus norvegicus

<400> SEQUENCE: 29

Tyr Ile Gly Phe Ser Gly Ser Thr Val Tyr Asn Pro Ser Leu Asn Ser
1               5                   10                  15

<210> SEQ ID NO 30
<211> LENGTH: 15
<212> TYPE: PRT
<213> ORGANISM: Rattus norvegicus

<400> SEQUENCE: 30

Ser Phe Val Gln Asn Thr Phe Ile Tyr Asp Trp Phe Phe Asp Phe
1               5                   10                  15

<210> SEQ ID NO 31
<211> LENGTH: 10
<212> TYPE: PRT
<213> ORGANISM: Rattus norvegicus

<400> SEQUENCE: 31

Gly Phe Ser Leu Thr Asn Asn Gly Val Ser
1               5                   10

<210> SEQ ID NO 32
<211> LENGTH: 16
<212> TYPE: PRT
<213> ORGANISM: Rattus norvegicus

<400> SEQUENCE: 32

Ala Ile Ser Ser Gly Gly Gly Thr Phe Tyr Asn Ser Ala Leu Lys Ser
1               5                   10                  15

<210> SEQ ID NO 33
<211> LENGTH: 10
<212> TYPE: PRT
<213> ORGANISM: Rattus norvegicus

<400> SEQUENCE: 33

```
Asp Gly Asp Trp Asp Trp Tyr Phe Asp Phe
1               5                   10
```

<210> SEQ ID NO 34
<211> LENGTH: 10
<212> TYPE: PRT
<213> ORGANISM: Mouse

<400> SEQUENCE: 34

```
Gly Tyr Thr Phe Thr Ser Tyr Trp Met His
1               5                   10
```

<210> SEQ ID NO 35
<211> LENGTH: 17
<212> TYPE: PRT
<213> ORGANISM: Mouse

<400> SEQUENCE: 35

```
Asn Ile Tyr Pro Gly Ser Gly Ser Thr Asn Tyr Asp Glu Lys Phe Lys
1               5                   10                  15

Ser
```

<210> SEQ ID NO 36
<211> LENGTH: 5
<212> TYPE: PRT
<213> ORGANISM: Mouse

<400> SEQUENCE: 36

```
Gly Thr Gly Ala Tyr
1               5
```

<210> SEQ ID NO 37
<211> LENGTH: 108
<212> TYPE: PRT
<213> ORGANISM: Rattus norvegicus

<400> SEQUENCE: 37

```
Glu Val Gln Met Thr Gln Ser Pro Ser Thr Leu Thr Ala Ser Pro Gly
1               5                   10                  15

Glu Ser Val Ser Ile Asn Cys Lys Ala Ser Lys Asn Ile Arg Ser Tyr
            20                  25                  30

Leu Ala Trp Tyr Gln Gln Lys Pro Gly Lys Pro Asn Lys Leu Leu Ile
        35                  40                  45

Tyr Ser Gly Ser Thr Leu His Ser Gly Thr Pro Ser Arg Phe Ser Gly
    50                  55                  60

Ser Gly Phe Gly Thr Asp Phe Thr Leu Thr Ile Arg Asn Leu Glu Pro
65                  70                  75                  80

Glu Asp Phe Gly Leu Tyr Tyr Cys Gln Gln His His Glu Tyr Pro Leu
                85                  90                  95

Thr Phe Gly Ser Gly Thr Lys Leu Glu Ile Lys Arg
            100                 105
```

<210> SEQ ID NO 38
<211> LENGTH: 108
<212> TYPE: PRT
<213> ORGANISM: Rattus norvegicus

<400> SEQUENCE: 38

```
Asp Val Gln Met Thr Gln Ser Pro Ser Tyr Leu Ala Ala Ser Pro Gly
1               5                   10                  15

Glu Ser Val Ser Ile Ser Cys Lys Ala Gly Lys Asn Ile Asn Thr Asn
```

```
                    20                  25                  30
Leu Ala Trp Tyr Gln Ala Lys Pro Gly Lys Thr Asn Lys Val Leu Ile
            35                  40                  45

His Ser Gly Ser Thr Leu Gln Ser Gly Thr Pro Ser Arg Phe Ser Gly
    50                  55                  60

Ser Gly Phe Gly Thr Asp Phe Thr Leu Thr Ile Arg Ser Leu Glu Pro
65                  70                  75                  80

Glu Asp Phe Ala Val Tyr Tyr Cys Gln Gln His Asn Glu Phe Pro Leu
                85                  90                  95

Thr Phe Gly Ser Gly Thr Lys Leu Glu Ile Lys Arg
            100                 105
```

<210> SEQ ID NO 39
<211> LENGTH: 108
<212> TYPE: PRT
<213> ORGANISM: Rattus norvegicus

<400> SEQUENCE: 39

```
Asp Val Arg Met Thr Gln Ser Pro Ser Asn Leu Ala Ala Ser Pro Gly
1               5                   10                  15

Glu Ser Val Ser Ile Asn Cys Lys Ala Ser Lys Asn Ile Ser Lys Tyr
                20                  25                  30

Leu Ala Trp Tyr Gln Gln Lys Pro Gly Lys Ala Asn Arg Leu Leu Ile
            35                  40                  45

Cys Ser Gly Ser Thr Leu Gln Ser Gly Thr Pro Ser Arg Phe Ser Gly
    50                  55                  60

Ser Gly Phe Gly Thr Asp Phe Thr Leu Thr Ile Arg Asn Leu Glu Pro
65                  70                  75                  80

Glu Asp Phe Gly Leu Tyr Tyr Cys Gln Gln His Asn Glu Phe Pro Leu
                85                  90                  95

Thr Phe Gly Ser Gly Thr Lys Leu Glu Ile Lys Arg
            100                 105
```

<210> SEQ ID NO 40
<211> LENGTH: 102
<212> TYPE: PRT
<213> ORGANISM: Rattus norvegicus

<400> SEQUENCE: 40

```
Asp Ile Val Met Thr Gln Ser Pro Thr Phe Met Ser Ile Ser Val Gly
1               5                   10                  15

Asp Arg Val Thr Met Ser Cys Lys Ala Ser Gln Asn Val Gly Ser Asn
                20                  25                  30

Val Asp Trp Tyr Gln Gln Lys Thr Gly Gln Ser Pro Lys Leu Leu Ile
            35                  40                  45

Tyr Lys Ala Ser Asn Arg Tyr Thr Gly Val Pro Asp Arg Phe Thr Gly
    50                  55                  60

Ser Gly Ser Gly Thr Gly Phe Thr Phe Thr Ile Thr Asn Leu Gln Ala
65                  70                  75                  80

Glu Asp Leu Ala Val Tyr Tyr Cys Met Gln Ser Leu Ser Phe Pro Tyr
                85                  90                  95

Thr Ser Gly Ala Gly Thr
            100
```

<210> SEQ ID NO 41
<211> LENGTH: 90
<212> TYPE: PRT
<213> ORGANISM: Mouse

<400> SEQUENCE: 41

Asp Val Gln Met Ile Gln Ser Pro Ser Ser Leu Ser Ala Ser Leu Gly
1               5                   10                  15

Asp Ile Val Thr Met Thr Cys Gln Ala Ser Gln Gly Thr Ser Ile Asn
            20                  25                  30

Leu Asn Trp Phe Gln Gln Lys Pro Gly Lys Ala Pro Lys Leu Leu Ile
        35                  40                  45

Tyr Ser Ala Asn Asn Leu Glu Asp Gly Val Pro Ser Arg Phe Ser Gly
50                  55                  60

Ser Gly Phe Gly Thr Asp Phe Thr Leu Thr Ile Ser Ser Leu Glu Asp
65                  70                  75                  80

Glu Asp Met Ala Thr Tyr Phe Cys Leu Gln
                85                  90

<210> SEQ ID NO 42
<211> LENGTH: 109
<212> TYPE: PRT
<213> ORGANISM: Artificial
<220> FEATURE:
<223> OTHER INFORMATION: humanized DX182 variable light chain region

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Lys Ala Ser Lys Asn Ile Arg Ser Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His His Glu Tyr Pro Leu
                85                  90                  95

Thr Phe Gly Gln Gly Thr Lys Val Glu Ile Lys Arg Thr
            100                 105

<210> SEQ ID NO 43
<211> LENGTH: 124
<212> TYPE: PRT
<213> ORGANISM: Rattus norvegicus

<400> SEQUENCE: 43

Glu Ile Gln Leu Gln Glu Ser Gly Pro Gly Leu Val Lys Pro Ser Gln
1               5                   10                  15

Ser Leu Ser Leu Thr Cys Ser Val Thr Gly Tyr Thr Ile Thr Ser Gly
            20                  25                  30

Tyr Asp Trp Ser Trp Ile Arg Lys Phe Pro Gly Asn Lys Met Glu Trp
        35                  40                  45

Met Gly Tyr Ile Asn Tyr Gly Ser Thr Asn Tyr Lys Pro Ser Leu
50                  55                  60

Gly Ser Arg Ile Ser Ile Thr Arg Asp Thr Ser Lys Asn Gln Phe Phe
65                  70                  75                  80

Leu Gln Leu Asn Ser Val Ser Pro Glu Asp Thr Ala Thr Tyr Tyr Cys
                85                  90                  95

Ala Lys Tyr Asn Glu Tyr Lys Ser Tyr Ile Tyr Asp Trp Tyr Phe Asp
            100                 105                 110

```
Phe Trp Gly Pro Gly Thr Met Val Thr Val Ser Ser
        115                 120

<210> SEQ ID NO 44
<211> LENGTH: 124
<212> TYPE: PRT
<213> ORGANISM: Rattus norvegicus

<400> SEQUENCE: 44

Glu Ile Gln Leu Gln Glu Ser Gly Pro Gly Leu Val Lys Pro Ser Gln
1               5                   10                  15

Ser Phe Ser Leu Thr Cys Ser Val Thr Gly Tyr Thr Ile Thr Ser Gly
            20                  25                  30

Tyr Asp Trp Ser Trp Ile Arg Lys Phe Pro Gly Asn Arg Met Glu Trp
        35                  40                  45

Met Gly Tyr Ile Asn Tyr Ser Gly Ser Thr Val Tyr Asn Pro Ser Leu
    50                  55                  60

Arg Ser Arg Phe Ser Ile Thr Arg Asp Thr Ser Lys Asn Gln Phe Phe
65                  70                  75                  80

Leu Gln Leu Asn Ser Val Ala Ser Glu Asp Thr Ala Thr Tyr Tyr Cys
                85                  90                  95

Ala Lys Phe Glu Ala Ser Asn Thr Tyr Leu Tyr Asp Trp Tyr Phe Asp
            100                 105                 110

Phe Trp Gly Pro Gly Thr Met Val Thr Val Ser Ser
        115                 120

<210> SEQ ID NO 45
<211> LENGTH: 124
<212> TYPE: PRT
<213> ORGANISM: Rattus norvegicus

<400> SEQUENCE: 45

Glu Ile Gln Leu Gln Glu Ser Gly Pro Gly Leu Val Lys Pro Ser Gln
1               5                   10                  15

Ser Leu Ser Leu Thr Cys Ser Val Thr Gly Phe Thr Ile Thr Ser Gly
            20                  25                  30

Tyr Asp Trp Ser Trp Ile Arg Lys Phe Pro Gly Asn Lys Met Glu Trp
        35                  40                  45

Met Gly Tyr Ile Gly Phe Ser Gly Ser Thr Val Tyr Asn Pro Ser Leu
    50                  55                  60

Asn Ser Arg Ile Ser Ile Thr Arg Asp Thr Ala Lys Asn Gln Phe Phe
65                  70                  75                  80

Leu Gln Leu Asn Ser Val Thr Thr Glu Asp Thr Ala Thr Tyr His Cys
                85                  90                  95

Ala Lys Ser Phe Val Gln Asn Thr Phe Ile Tyr Asp Trp Phe Phe Asp
            100                 105                 110

Phe Trp Gly Pro Gly Thr Met Val Thr Val Ser Ser
        115                 120

<210> SEQ ID NO 46
<211> LENGTH: 118
<212> TYPE: PRT
<213> ORGANISM: Rattus norvegicus

<400> SEQUENCE: 46

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Asn Asn
```

Gly Val Ser Trp Val Arg Gln Pro Gly Lys Gly Leu Glu Trp Ile
            35                  40                  45

Ala Ala Ile Ser Ser Gly Gly Thr Phe Tyr Asn Ser Ala Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Ile Tyr Phe Cys Ala
                    85                  90                  95

Arg Asp Gly Asp Trp Asp Trp Tyr Phe Asp Phe Trp Gly Pro Gly Thr
                100                 105                 110

Met Val Thr Val Ser Ser
            115

<210> SEQ ID NO 47
<211> LENGTH: 114
<212> TYPE: PRT
<213> ORGANISM: Mouse

<400> SEQUENCE: 47

Gln Val Gln Leu Gln Gln Pro Gly Ser Glu Leu Val Arg Pro Gly Val
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg His Gly Gln Gly Leu Glu Trp Ile
            35                  40                  45

Gly Asn Ile Tyr Pro Gly Ser Gly Ser Thr Asn Tyr Asp Glu Lys Phe
    50                  55                  60

Lys Ser Lys Gly Thr Leu Thr Val Asp Thr Ser Ser Ser Thr Ala Tyr
65                  70                  75                  80

Met His Leu Ser Ser Leu Thr Ser Glu Asp Ser Ala Val Tyr Tyr Cys
                85                  90                  95

Thr Thr Gly Thr Gly Ala Tyr Trp Gly Gln Gly Thr Leu Val Thr Val
                100                 105                 110

Ser Ala

<210> SEQ ID NO 48
<211> LENGTH: 124
<212> TYPE: PRT
<213> ORGANISM: Artificial
<220> FEATURE:
<223> OTHER INFORMATION: Humanized DX182 variable heavy chain region

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Thr Ile Thr Ser Gly
                20                  25                  30

Tyr Asp Trp Ser Trp Ile Arg Gln Pro Pro Gly Lys Gly Leu Glu Trp
            35                  40                  45

Ile Gly Tyr Ile Asn Tyr Gly Gly Ser Thr Asn Tyr Lys Pro Ser Leu
    50                  55                  60

Gly Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Asn Glu Tyr Lys Ser Tyr Ile Tyr Asp Trp Tyr Phe Asp

```
                     100                 105                 110
Phe Trp Gly Gln Gly Thr Leu Val Thr Val Ser Ser
            115                 120

<210> SEQ ID NO 49
<211> LENGTH: 214
<212> TYPE: PRT
<213> ORGANISM: Artificial
<220> FEATURE:
<223> OTHER INFORMATION: Humanized DX182 Light Chain

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Lys Ala Ser Lys Asn Ile Arg Ser Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His His Glu Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 50
<211> LENGTH: 454
<212> TYPE: PRT
<213> ORGANISM: Artificial
<220> FEATURE:
<223> OTHER INFORMATION: Humanized DX182 Heavy Chain

<400> SEQUENCE: 50

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Thr Ile Thr Ser Gly
            20                  25                  30

Tyr Asp Trp Ser Trp Ile Arg Gln Pro Pro Gly Lys Gly Leu Glu Trp
        35                  40                  45

Ile Gly Tyr Ile Asn Tyr Gly Gly Ser Thr Asn Tyr Lys Pro Ser Leu
50                  55                  60

Gly Ser Arg Val Thr Ile Ser Val Asp Thr Ser Lys Asn Gln Phe Ser
```

```
                65                  70                  75                  80
Leu Lys Leu Ser Ser Val Thr Ala Ala Asp Thr Ala Val Tyr Tyr Cys
                    85                  90                  95
Ala Arg Tyr Asn Glu Tyr Lys Ser Tyr Ile Tyr Asp Trp Tyr Phe Asp
                100                 105                 110
Phe Trp Gly Gln Gly Thr Leu Val Thr Val Ser Ser Ala Ser Thr Lys
                115                 120                 125
Gly Pro Ser Val Phe Pro Leu Ala Pro Ser Ser Lys Ser Thr Ser Gly
            130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
                180                 185                 190
Val Thr Val Pro Ser Ser Leu Gly Thr Gln Thr Tyr Ile Cys Asn
                195                 200                 205
Val Asn His Lys Pro Ser Asn Thr Lys Val Asp Lys Lys Val Glu Pro
            210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
                260                 265                 270
Val Ser His Glu Asp Pro Glu Val Lys Phe Asn Trp Tyr Val Asp Gly
            275                 280                 285
Val Glu Val His Asn Ala Lys Thr Lys Pro Arg Glu Glu Gln Tyr Asn
        290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Asp Glu Leu Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Lys
    450

<210> SEQ ID NO 51
<211> LENGTH: 233
<212> TYPE: PRT
<213> ORGANISM: Artificial
<220> FEATURE:
```

<223> OTHER INFORMATION: Humanized DX182 Light Chain with signal peptide

<400> SEQUENCE: 51

Met Ala Pro Val Gln Leu Leu Gly Leu Leu Val Leu Phe Leu Pro Ala
1               5                   10                  15
Met Arg Cys Asp Ile Gln Met Thr Gln Ser Pro Ser Ser Leu Ser Ala
            20                  25                  30
Ser Val Gly Asp Arg Val Thr Ile Thr Cys Lys Ala Ser Lys Asn Ile
        35                  40                  45
Arg Ser Tyr Leu Ala Trp Tyr Gln Gln Lys Pro Gly Lys Ala Pro Lys
    50                  55                  60
Leu Leu Ile Tyr Ser Gly Ser Thr Leu His Ser Gly Val Pro Ser Arg
65                  70                  75                  80
Phe Ser Gly Ser Gly Ser Gly Thr Asp Phe Thr Leu Thr Ile Ser Ser
                85                  90                  95
Leu Gln Pro Glu Asp Phe Ala Thr Tyr Tyr Cys Gln Gln His His Glu
            100                 105                 110
Tyr Pro Leu Thr Phe Gly Gln Gly Thr Lys Val Glu Ile Lys Arg Thr
        115                 120                 125
Val Ala Ala Pro Ser Val Phe Ile Phe Pro Pro Ser Asp Glu Gln Leu
    130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
        195                 200                 205
Lys Val Tyr Ala Cys Glu Val Thr His Gln Gly Leu Ser Ser Pro Val
    210                 215                 220
Thr Lys Ser Phe Asn Arg Gly Glu Cys
225                 230

<210> SEQ ID NO 52
<211> LENGTH: 702
<212> TYPE: DNA
<213> ORGANISM: Artificial
<220> FEATURE:
<223> OTHER INFORMATION: Humanized DX182 Light Chain with signal peptide

<400> SEQUENCE: 52
atggctccag tgcagctgct ggggctgctg gtgctgttcc tgccagccat gagatgtgat      60
atccagatga cccagtctcc atcctccctg tctgcctctg tgggcgacag agtgaccatc     120
acctgcaagg ccagcaagaa catccggagc tacctggcct ggtatcagca gaagccaggg     180
aaggccccta agctgctgat ctattctggc tccaccctgc actctggggt gccatccagg     240
ttcagcggca gcggctctgg gacagacttc accctgacca tcagcagcct gcagcctgag     300
gacttcgcca cctactactg tcagcagcac acgagtatc cactgacctt cggccagggc      360
accaaggtgg agatcaagcg tacggtggct gcaccatctg tcttcatctt ccctccatct     420
gatgagcagc tgaagtctgg aactgcctcc gtggtgtgcc tgctgaataa cttctatccc     480
agagaggcca aggtgcagtg gaaggtggat aacgccctcc agagcggcaa ctcccaggag     540
agcgtgacag agcaggacag caaggacagc acctacagcc tgagcagcac cctgaccctg     600
agcaaagcag actacgagaa acacaaggtg tacgcctgcg aggtgaccca tcagggcctg     660 agcagcccccg tgacaaagag cttcaacagg ggagagtgtt aa          702

<210> SEQ ID NO 53
<211> LENGTH: 473
<212> TYPE: PRT
<213> ORGANISM: Artificial
<220> FEATURE:
<223> OTHER INFORMATION: Humanized DX182 heavy Chain with signal peptide

<400> SEQUENCE: 53

```
Met Ala Val Leu Gly Leu Leu Phe Cys Leu Val Thr Phe Pro Ser Cys
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Tyr Thr Ile
        35                  40                  45

Thr Ser Gly Tyr Asp Trp Ser Trp Ile Arg Gln Pro Pro Gly Lys Gly
    50                  55                  60

Leu Glu Trp Ile Gly Tyr Ile Asn Tyr Gly Gly Ser Thr Asn Tyr Lys
65                  70                  75                  80

Pro Ser Leu Gly Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Tyr Asn Glu Tyr Lys Ser Tyr Ile Tyr Asp Trp
        115                 120                 125

Tyr Phe Asp Phe Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
```

```
                355                 360                 365
Pro Arg Glu Pro Gln Val Tyr Thr Leu Pro Pro Ser Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
        450                 455                 460

Lys Ser Leu Ser Leu Ser Pro Gly Lys
465                 470

<210> SEQ ID NO 54
<211> LENGTH: 1422
<212> TYPE: DNA
<213> ORGANISM: Artificial
<220> FEATURE:
<223> OTHER INFORMATION: Humanized DX182 heavy Chain with signal peptide

<400> SEQUENCE: 54
atggctgtgc tgggctgct gttctgcctg gtgacattcc caagctgtgt gctgtcccag      60
gtgcagctgc aggaatctgg acccggactg gtgaagcctt ccgaaacact gagcctgaca     120
tgtacagtgt ctggctacac aatcaccagc ggctacgact ggagctggat cagacagcca     180
cctggcaagg gctggagtg atcggctat atcaactacg cggatccac caactacaag       240 ccttccctgg cagcagagt caccatctcc gtggacacat ccaagaacca gtttagcctg      300
aagctgagca gcgtgacagc cgctgacacc gccgtgtatt actgtgccag atacaacgag    360
tacaagagct acatctacga ctggtacttc gacttctggg gccagggcac cctggtgacc    420
gtgtccagcg ctagcaccaa gggcccatcg gtcttccccc tggcaccctc ctccaagagc    480
acctctgggg gcacagcggc cctgggctgc ctggtcaagg actacttccc cgaaccggtg    540
acggtgtcgt ggaactcagg cgccctgacc agcggcgtgc acaccttccc ggctgtccta    600
cagtcctcag gactctactc cctcagcagc gtggtgaccg tgccctccag cagcttgggc    660
acccagacct acatctgcaa cgtgaatcac aagcccagca caccaaggt ggacaagaaa     720 gttgagccca atcttgtga caaaactcac acatgcccac cgtgcccagc acctgaactc    780
ctggggggac cgtcagtctt cctcttcccc ccaaaaccca aggacaccct catgatctcc    840
cggacccctg aggtcacatg cgtggtggtg gacgtgagcc acgaagaccc tgaggtcaag    900
ttcaactggt acgtggacgg cgtggaggtg cataatgcca agacaaagcc gcggaggag    960 cagtacaaca gcacgtaccg tgtggtcagc gtcctcaccg tcctgcacca ggactggctg   1020
aatggcaagg agtacaagtg caaggtctcc aacaaagccc tcccagcccc catcgagaaa   1080
accatctcca aagccaaagg gcagcccga gaaccacagg tgtacaccct gcccccatcc    1140
cgggatgagc tgaccaagaa ccaggtcagc ctgacctgcc tggtcaaagg cttctatccc   1200
agcgacatcg ccgtggagtg ggagagcaat gggcagccgg agaacaacta caagaccacg   1260
cctcccgtgc tggactccga cggctccttc ttcctctaca gcaagctcac cgtggacaag   1320
agcaggtggc agcaggggaa cgtcttctca tgctccgtga tgcatgaggc tctgcacaac   1380
cactacacgc agaagagcct ctccctgtct ccgggtaaat ga                       1422
```

<210> SEQ ID NO 55
<211> LENGTH: 11
<212> TYPE: PRT
<213> ORGANISM: Rattus norvegicus

<400> SEQUENCE: 55

Arg Ala Ser Lys Asn Ile Arg Ser Tyr Leu Ala
1               5                   10

<210> SEQ ID NO 56
<211> LENGTH: 109
<212> TYPE: PRT
<213> ORGANISM: Artificial
<220> FEATURE:
<223> OTHER INFORMATION: huDX248 light variable chain domain

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Thr Ser Ile Asn
            20                  25                  30

Leu Asn Trp Tyr Gln Gln Lys Pro Gly Lys Ala Pro Lys Leu Leu Ile
        35                  40                  45

Tyr Ser Ala Asn Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ile Thr Tyr Leu Pro Trp
                85                  90                  95

Thr Phe Gly Gln Gly Thr Lys Val Glu Ile Lys Arg Thr
            100                 105

<210> SEQ ID NO 57
<211> LENGTH: 114
<212> TYPE: PRT
<213> ORGANISM: Artificial
<220> FEATURE:
<223> OTHER INFORMATION: huDX248 heavy variable chain domain

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Asn Ile Tyr Pro Gly Ser Gly Ser Thr Asn Tyr Asp Glu Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Thr Gly Ala Tyr Trp Gly Gln Gly Thr Leu Val Thr Val
            100                 105                 110

Ser Ser

<210> SEQ ID NO 58
<211> LENGTH: 271
<212> TYPE: PRT

-continued

<213> ORGANISM: Homo sapiens

<400> SEQUENCE: 58

Met Ser Ala Pro Arg Leu Leu Ile Ser Ile Ile Met Val Ser Ala
1               5                   10                  15

Ser Ser Ser Ser Cys Met Gly Gly Lys Gln Met Thr Gln Asn Tyr Ser
            20                  25                  30

Thr Ile Phe Ala Glu Gly Asn Ile Ser Gln Pro Val Leu Met Asp Ile
        35                  40                  45

Asn Ala Val Leu Cys Cys Pro Pro Ile Ala Leu Arg Asn Leu Ile Ile
50                  55                  60

Ile Thr Trp Glu Ile Ile Leu Arg Gly Gln Pro Ser Cys Thr Lys Ala
65                  70                  75                  80

Tyr Lys Lys Glu Thr Asn Glu Thr Lys Glu Thr Asn Cys Thr Val Glu
                85                  90                  95

Arg Ile Thr Trp Val Ser Arg Pro Asp Gln Asn Ser Asp Leu Gln Ile
            100                 105                 110

Leu Pro Val Asp Thr Thr His Asp Gly Tyr Tyr Arg Gly Ile Val Val
        115                 120                 125

Thr Pro Asp Gly Asn Phe His Arg Gly Tyr His Leu Gln Val Leu Val
130                 135                 140

Thr Pro Glu Val Asn Leu Phe Gln Ser Arg Asn Ile Thr Ala Val Cys
145                 150                 155                 160

Lys Ala Val Thr Gly Lys Pro Ala Ala Gln Ile Ser Trp Ile Pro Glu
                165                 170                 175

Gly Ser Ile Leu Ala Thr Lys Gln Glu Tyr Trp Gly Asn Gly Thr Val
            180                 185                 190

Thr Val Lys Ser Thr Cys Pro Trp Glu Gly His Lys Ser Thr Val Thr
        195                 200                 205

Cys His Val Ser His Leu Thr Gly Asn Lys Ser Leu Ser Val Lys Leu
210                 215                 220

Asn Ser Gly Leu Arg Thr Ser Gly Ser Pro Ala Leu Ser Leu Leu Ile
225                 230                 235                 240

Ile Leu Tyr Val Lys Leu Ser Leu Phe Val Val Ile Leu Val Thr Thr
                245                 250                 255

Gly Phe Val Phe Phe Gln Arg Ile Asn His Val Arg Lys Val Leu
            260                 265                 270

<210> SEQ ID NO 59
<211> LENGTH: 271
<212> TYPE: PRT
<213> ORGANISM: Chimpanzee

<400> SEQUENCE: 59

Met Ser Ala Pro Arg Leu Leu Ile Ser Ile Ile Met Val Pro Ala
1               5                   10                  15

Ser Ser Ser Ser Cys Met Gly Gly Lys Gln Met Thr Gln Asn Tyr Ser
            20                  25                  30

Thr Ile Phe Ala Glu Gly Asn Ile Ser Gln Pro Val Leu Met Asp Thr
        35                  40                  45

Asn Ala Val Leu Cys Cys Thr Pro Ile Ala Leu Arg Asn Leu Ile Ile
50                  55                  60

Ile Thr Trp Glu Ile Ile Leu Arg Gly Gln Pro Ser Cys Thr Lys Ala
65                  70                  75                  80

Tyr Lys Lys Glu Thr Asn Glu Thr Lys Glu Thr Asn Cys Thr Ala Glu
                85                  90                  95

-continued

```
Arg Ile Thr Trp Val Ser Arg Pro Asp Gln Asn Ser Asp Leu Gln Ile
            100                 105                 110

Arg Pro Val Asp Thr Thr His Asp Gly Tyr Tyr Arg Gly Ile Val Val
            115                 120                 125

Thr Pro Asp Gly Asn Phe His Arg Gly Tyr His Leu Gln Val Leu Val
        130                 135                 140

Thr Pro Glu Val Thr Leu Phe Gln Ser Trp Asn Arg Thr Ala Val Cys
145                 150                 155                 160

Lys Ala Val Thr Gly Lys Pro Ala Ala Gln Ile Ser Trp Ile Pro Glu
                165                 170                 175

Gly Ser Ile Leu Ala Thr Lys Gln Glu Tyr Trp Gly Asn Gly Thr Val
            180                 185                 190

Thr Val Lys Ser Thr Cys Pro Trp Glu Gly His Lys Ser Thr Val Thr
        195                 200                 205

Cys His Val Ser His Leu Thr Gly Asn Lys Ser Leu Ser Val Lys Val
    210                 215                 220

Asn Ser Gly Leu Arg Thr Ser Gly Ser Pro Ala Leu Ser Leu Leu Ile
225                 230                 235                 240

Ile Leu Tyr Val Lys Leu Ser Leu Phe Val Ile Leu Val Thr Thr
                245                 250                 255

Gly Phe Val Phe Phe Gln Arg Ile Asn His Val Arg Lys Val Leu
            260                 265                 270

<210> SEQ ID NO 60
<211> LENGTH: 272
<212> TYPE: PRT
<213> ORGANISM: Rhesus

<400> SEQUENCE: 60

Met Ser Ala Ser Arg Leu Leu Ile Ser Ile Ile Met Val Ser Ala
1               5                   10                  15

Ser Ser Ser Ser Cys Met Asp Gly Lys Gln Met Thr Gln Asn Tyr Ser
            20                  25                  30

Lys Met Ser Ala Glu Gly Asn Ile Ser Gln Pro Val Leu Met Asp Thr
        35                  40                  45

Asn Ala Met Leu Cys Cys Pro Pro Ile Glu Phe Arg Asn Leu Ile Leu
    50                  55                  60

Ile Val Trp Glu Ile Ile Ile Arg Gly Gln Pro Ser Cys Thr Lys Ala
65                  70                  75                  80

Tyr Arg Lys Glu Thr Asn Glu Thr Lys Glu Thr Asn Cys Thr Asp Lys
                85                  90                  95

Arg Ile Thr Trp Val Ser Thr Pro Asp Gln Asn Ser Asp Leu Gln Ile
            100                 105                 110

His Pro Val Ala Ile Thr His Asp Gly Tyr Tyr Arg Cys Ile Met Ala
            115                 120                 125

Thr Pro Asp Gly Asn Phe His His Gly Tyr His Leu Gln Val Leu Val
        130                 135                 140

Thr Pro Glu Val Thr Leu Phe Gln Ser Arg Asn Arg Thr Ala Val Cys
145                 150                 155                 160

Lys Ala Val Ala Gly Lys Pro Ala Ala Gln Ile Ser Trp Ile Pro Ala
                165                 170                 175

Gly Asn Cys Ala Pro Thr Glu His Glu Tyr Trp Gly Asn Gly Thr Val
            180                 185                 190

Thr Val Glu Ser Met Cys His Trp Gly Asp His Asn Ala Ser Thr Val
        195                 200                 205
```

Thr Cys His Val Ser His Leu Thr Gly Asn Lys Ser Leu Tyr Ile Lys
    210                 215                 220

Leu Asn Ser Gly Leu Arg Thr Ser Gly Ser Pro Ala Leu Asp Leu Leu
225                 230                 235                 240

Ile Ile Leu Tyr Val Lys Leu Ser Leu Phe Val Val Ile Leu Val Thr
                245                 250                 255

Thr Gly Phe Val Phe Gln Arg Ile Asn Tyr Val Arg Lys Ser Leu
        260                 265                 270

<210> SEQ ID NO 61
<211> LENGTH: 272
<212> TYPE: PRT
<213> ORGANISM: Cynomolgus monkey

<400> SEQUENCE: 61

Met Ser Ala Ser Arg Leu Leu Ile Ser Ile Ile Met Val Ser Ala
1               5                   10                  15

Ser Ser Ser Ser Cys Met Asp Gly Lys Gln Met Thr Gln Asn Tyr Ser
                20                  25                  30

Lys Met Ser Ala Glu Gly Asn Ile Ser Gln Pro Val Leu Met Asp Thr
            35                  40                  45

Asn Ala Met Leu Cys Cys Pro Pro Ile Glu Phe Arg Asn Leu Ile Val
50                  55                  60

Ile Val Trp Glu Ile Ile Ile Arg Gly Gln Pro Ser Cys Thr Lys Ala
65                  70                  75                  80

Tyr Arg Lys Glu Thr Asn Glu Thr Lys Glu Thr Asn Cys Thr Asp Lys
                85                  90                  95

Arg Ile Thr Trp Val Ser Thr Pro Asp Gln Asn Ser Asp Leu Gln Ile
            100                 105                 110

His Pro Val Ala Ile Thr His Asp Gly Tyr Tyr Arg Cys Ile Met Ala
        115                 120                 125

Thr Pro Asp Gly Asn Phe His Arg Gly Tyr His Leu Gln Val Leu Val
130                 135                 140

Thr Pro Glu Val Thr Leu Phe Gln Ser Arg Asn Arg Thr Ala Val Cys
145                 150                 155                 160

Lys Ala Val Ala Gly Lys Pro Ala Ala Gln Ile Ser Trp Ile Pro Ala
                165                 170                 175

Gly Asp Cys Ala Pro Thr Glu His Glu Tyr Trp Gly Asn Gly Thr Val
            180                 185                 190

Thr Val Glu Ser Met Cys His Trp Gly Asp His Asn Ala Ser Thr Val
        195                 200                 205

Thr Cys His Val Ser His Leu Thr Gly Asn Lys Ser Leu Tyr Ile Lys
    210                 215                 220

Leu Asn Ser Gly Leu Arg Thr Ser Gly Ser Pro Ala Leu Asp Leu Leu
225                 230                 235                 240

Ile Ile Leu Tyr Val Lys Leu Ser Leu Phe Val Val Ile Leu Val Thr
                245                 250                 255

Thr Gly Phe Val Phe Gln Arg Ile Asn Tyr Val Arg Lys Ser Leu
        260                 265                 270

<210> SEQ ID NO 62
<211> LENGTH: 326
<212> TYPE: PRT
<213> ORGANISM: Cynomolgus monkey

<400> SEQUENCE: 62

```
Met Leu Cys Pro Trp Arg Thr Ala Asn Leu Gly Leu Leu Leu Ile Leu
1               5                   10                  15

Ala Val Phe Leu Val Ala Ala Ser Asn Ser Leu Cys Met Asp Glu Lys
            20                  25                  30

Gln Ile Thr Gln Asn His Ser Lys Val Leu Ala Glu Val Asn Ile Ser
                35                  40                  45

Trp Pro Val Gln Met Ala Arg Asn Ala Val Leu Cys Cys Pro Pro Ile
    50                  55                  60

Glu Phe Arg Asn Leu Ile Val Ile Thr Trp Glu Ile Ile Leu Arg Gly
65                  70                  75                  80

Gln Pro Ser Cys Thr Lys Thr Tyr Arg Lys Asp Thr Asn Glu Thr Lys
                85                  90                  95

Glu Thr Asn Cys Thr Asp Glu Arg Ile Thr Trp Val Ser Thr Pro Asp
                100                 105                 110

Gln Asn Ser Asp Leu Gln Ile His Pro Val Ala Ile Thr His Asp Gly
                115                 120                 125

Tyr Tyr Arg Cys Ile Met Ala Thr Pro Asp Gly Asn Phe His Arg Gly
    130                 135                 140

Tyr His Leu Gln Val Leu Val Thr Pro Glu Val Thr Leu Phe Glu Ser
145                 150                 155                 160

Arg Asn Arg Thr Ala Val Cys Lys Ala Val Ala Gly Lys Pro Ala Ala
                165                 170                 175

Gln Ile Ser Trp Ile Pro Ala Gly Asp Cys Ala Pro Thr Glu Gln Glu
                180                 185                 190

Tyr Trp Gly Asn Gly Thr Val Thr Val Lys Ser Thr Cys His Trp Glu
    195                 200                 205

Gly His Asn Val Ser Thr Val Thr Cys His Val Ser His Leu Thr Gly
210                 215                 220

Asn Lys Ser Leu Tyr Ile Glu Leu Leu Pro Val Pro Gly Ala Lys Lys
225                 230                 235                 240

Ser Ala Lys Leu Tyr Met Pro Tyr Val Ile Leu Thr Ile Ile Ile Leu
                245                 250                 255

Thr Ile Val Gly Phe Ile Trp Leu Leu Lys Ile Ser Gly Cys Arg Lys
                260                 265                 270

Tyr Asn Leu Asn Lys Thr Glu Ser Thr Ser Val Val Glu Glu Asp Glu
                275                 280                 285

Met Gln Pro Tyr Ala Ser Tyr Thr Glu Lys Asn Asn Pro Leu Tyr Asp
    290                 295                 300

Thr Thr Asn Lys Val Lys Ala Ser Gln Ala Leu Gln Ser Glu Val Gly
305                 310                 315                 320

Thr Asp Leu His Thr Leu
                325
```

<210> SEQ ID NO 63
<211> LENGTH: 325
<212> TYPE: PRT
<213> ORGANISM: Homo sapiens

<400> SEQUENCE: 63

```
Met Leu Cys Pro Trp Arg Thr Ala Asn Leu Gly Leu Leu Leu Ile Leu
1               5                   10                  15

Thr Ile Phe Leu Val Ala Ala Ser Ser Leu Cys Met Asp Glu Lys
            20                  25                  30

Gln Ile Thr Gln Asn Tyr Ser Lys Val Leu Ala Glu Val Asn Thr Ser
                35                  40                  45
```

-continued

```
Trp Pro Val Lys Met Ala Thr Asn Ala Val Leu Cys Cys Pro Pro Ile
    50                  55                  60
Ala Leu Arg Asn Leu Ile Ile Ile Thr Trp Glu Ile Ile Leu Arg Gly
65                  70                  75                  80
Gln Pro Ser Cys Thr Lys Ala Tyr Lys Lys Glu Thr Asn Glu Thr Lys
                85                  90                  95
Glu Thr Asn Cys Thr Asp Glu Arg Ile Thr Trp Val Ser Arg Pro Asp
            100                 105                 110
Gln Asn Ser Asp Leu Gln Ile Arg Thr Val Ala Ile Thr His Asp Gly
            115                 120                 125
Tyr Tyr Arg Cys Ile Met Val Thr Pro Asp Gly Asn Phe His Arg Gly
    130                 135                 140
Tyr His Leu Gln Val Leu Val Thr Pro Glu Val Thr Leu Phe Gln Asn
145                 150                 155                 160
Arg Asn Arg Thr Ala Val Cys Lys Ala Val Ala Gly Lys Pro Ala Ala
                165                 170                 175
His Ile Ser Trp Ile Pro Glu Gly Asp Cys Ala Thr Lys Gln Glu Tyr
            180                 185                 190
Trp Ser Asn Gly Thr Val Thr Val Lys Ser Thr Cys His Trp Glu Val
            195                 200                 205
His Asn Val Ser Thr Val Thr Cys His Val Ser His Leu Thr Gly Asn
    210                 215                 220
Lys Ser Leu Tyr Ile Glu Leu Leu Pro Val Pro Gly Ala Lys Lys Ser
225                 230                 235                 240
Ala Lys Leu Tyr Ile Pro Tyr Ile Ile Leu Thr Ile Ile Ile Leu Thr
                245                 250                 255
Ile Val Gly Phe Ile Trp Leu Leu Lys Val Asn Gly Cys Arg Lys Tyr
                260                 265                 270
Lys Leu Asn Lys Thr Glu Ser Thr Pro Val Val Glu Glu Asp Glu Met
            275                 280                 285
Gln Pro Tyr Ala Ser Tyr Thr Glu Lys Asn Asn Pro Leu Tyr Asp Thr
    290                 295                 300
Thr Asn Lys Val Lys Ala Ser Glu Ala Leu Gln Ser Glu Val Asp Thr
305                 310                 315                 320
Asp Leu His Thr Leu
                325
```